United States Patent
Liu et al.

(10) Patent No.: US 12,410,260 B2
(45) Date of Patent: Sep. 9, 2025

(54) HIGHLY MODULAR BIEPITOPIC AND BISPECIFIC CAR-T CELLS FOR CANCER IMMUNOTHERAPY

(71) Applicant: THE UNIVERSITY OF NORTH CAROLINA AT CHAPEL HILL, Chapel Hill, NC (US)

(72) Inventors: Rihe Liu, Chapel Hill, NC (US); Gianpietro Dotti, Chapel Hill, NC (US); JingJing Li, Chapel Hill, NC (US); Jiyoung Ahn Morrison, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 1066 days.

(21) Appl. No.: 17/420,251

(22) PCT Filed: Jan. 10, 2020

(86) PCT No.: PCT/US2020/013039
§ 371 (c)(1),
(2) Date: Jul. 1, 2021

(87) PCT Pub. No.: WO2020/146706
PCT Pub. Date: Jul. 16, 2020

(65) Prior Publication Data
US 2022/0064326 A1 Mar. 3, 2022

Related U.S. Application Data

(60) Provisional application No. 62/791,424, filed on Jan. 11, 2019.

(51) Int. Cl.
| | |
|---|---|
| C07K 19/00 | (2006.01) |
| A61K 38/00 | (2006.01) |
| A61K 40/11 | (2025.01) |
| A61K 40/31 | (2025.01) |
| A61K 40/42 | (2025.01) |
| A61P 35/00 | (2006.01) |
| C07K 14/705 | (2006.01) |
| C07K 14/725 | (2006.01) |
| C07K 16/28 | (2006.01) |
| C07K 16/32 | (2006.01) |

(52) U.S. Cl.
CPC .............. *C07K 16/32* (2013.01); *A61K 40/11* (2025.01); *A61K 40/31* (2025.01); *A61K 40/4204* (2025.01); *A61K 40/4205* (2025.01); *A61P 35/00* (2018.01); *C07K 14/7051* (2013.01); *C07K 14/70517* (2013.01); *C07K 14/70521* (2013.01); *C07K 16/2863* (2013.01); *A61K 2239/29* (2023.05); *A61K 2239/31* (2023.05); *A61K 2239/38* (2023.05); *A61K 2239/54* (2023.05); *C07K 2317/31* (2013.01); *C07K 2317/569* (2013.01); *C07K 2319/02* (2013.01); *C07K 2319/03* (2013.01)

(58) Field of Classification Search
None
See application file for complete search history.

(56) References Cited

U.S. PATENT DOCUMENTS 6,673,901 B2   1/2004  Koide

FOREIGN PATENT DOCUMENTS

| WO | WO/2008/031098 | 3/2008 |
| WO | WO/2012/016245 | 2/2012 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser: Boston, pp. 491-495.*
Skolnick et al. (2000). Trends in Biotech. 18(1):34-39.*

* cited by examiner

*Primary Examiner* — Christine J Saoud
*Assistant Examiner* — Jon M Lockard
(74) *Attorney, Agent, or Firm* — Lisa Mueller; Casimir Jones SC

(57) ABSTRACT

Provided herein are biepitopic or bispecific chimeric antigen receptors. The chimeric antigen receptors comprise a combination of single domain antibody mimics. The single domain antibody mimics may be monobodies, affibodies, or DARPins. The disclosed chimeric antigen receptors may recognize two different epitopes of the same tumor antigen. For example, the chimeric antigen receptor may recognize two different epitopes of HER-2 or EGFR. The disclosed chimeric antigen receptors may recognize two epitopes of two different tumor antigens. For example, the chimeric antigen receptor may recognize HER-2 and EGFR. The disclosed chimeric antigen receptors may be expressed in immune cells for use in cancer immunotherapy.

4 Claims, 39 Drawing Sheets
Specification includes a Sequence Listing.

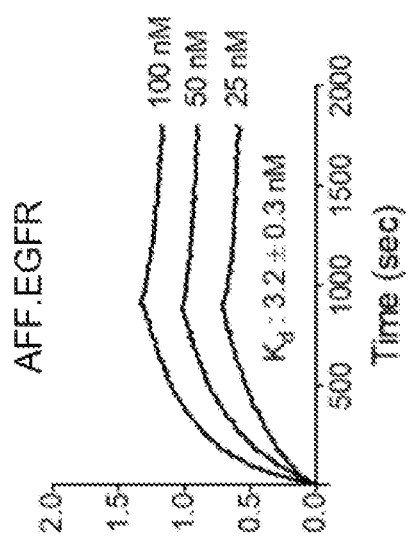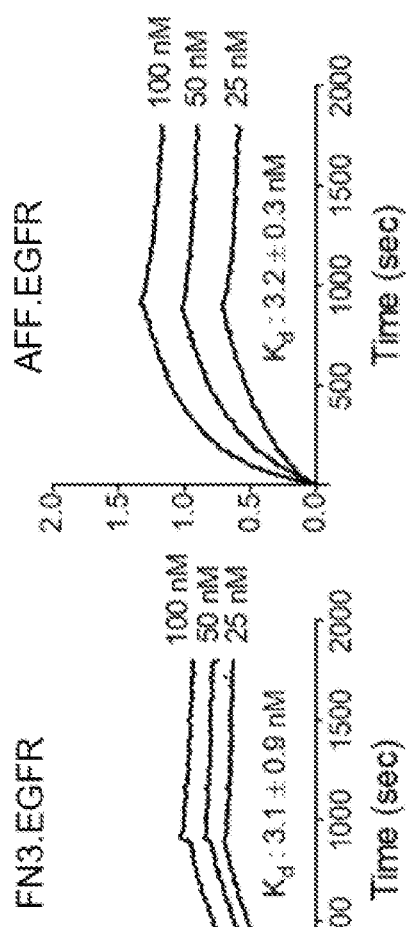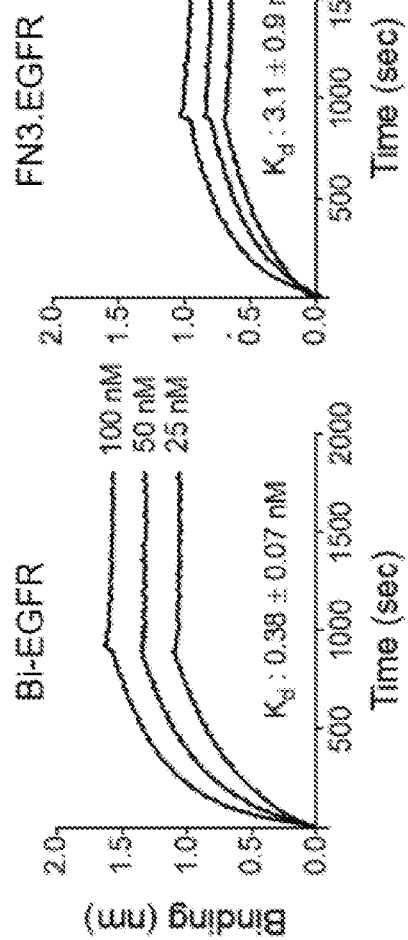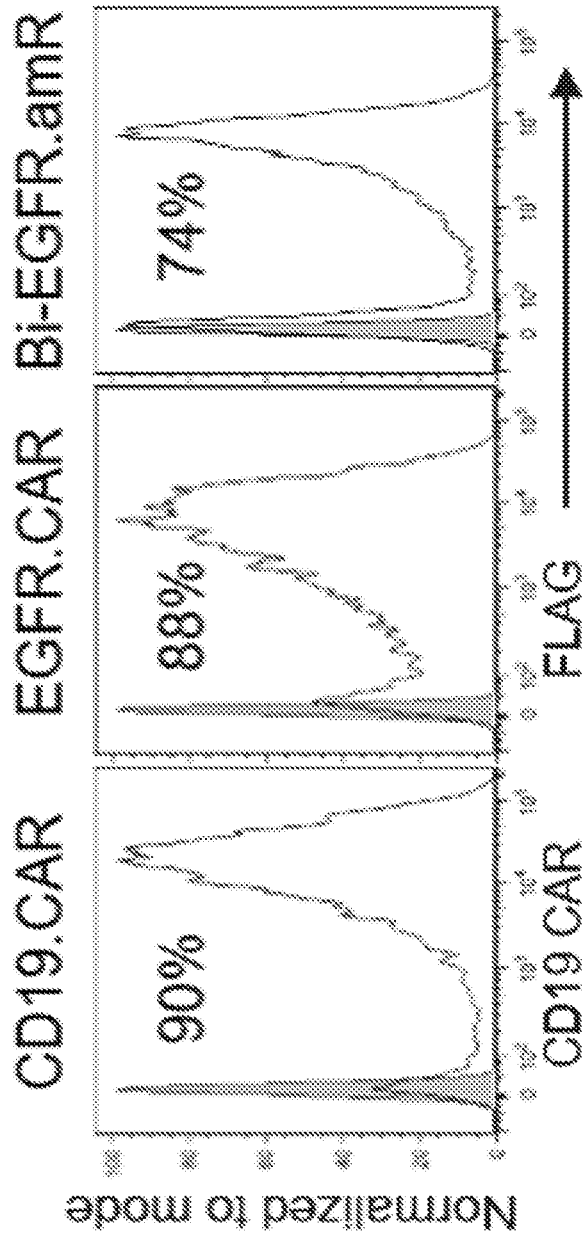

FIG. 4F
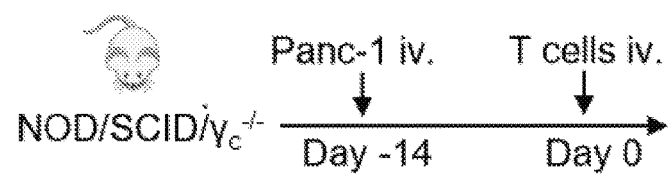
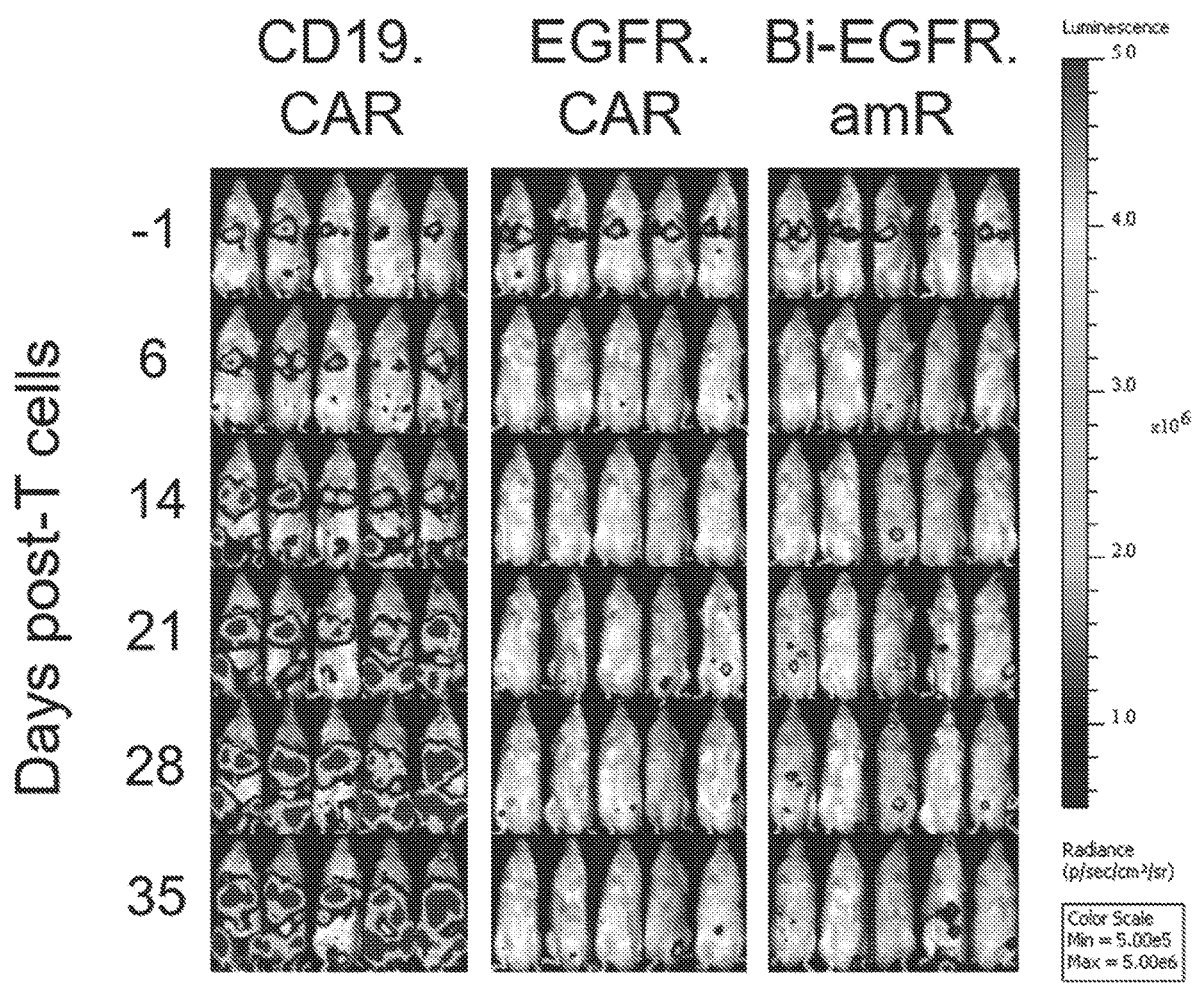
FIG. 4G

HIGHLY MODULAR BIEPITOPIC AND BISPECIFIC CAR-T CELLS FOR CANCER IMMUNOTHERAPY

STATEMENT REGARDING FEDERALLY SPONSORED RESEARCH OR DEVELOPMENT

This invention was made with government support under grant number CA157738 awarded by the National Institutes of Health (NIH). The government has certain rights in the invention.

RELATED APPLICATION

This application claims priority to U.S. Provisional Application No. 62/791,424, filed Jan. 11, 2019, the entire contents of which are incorporated herein by reference.

FIELD

Provided herein are chimeric antigen receptors. In particular, provided herein are chimeric antigen receptors comprising a combination of single domain antibody mimics. The disclosed chimeric antigen receptors may be used for T-cell therapy.

BACKGROUND

Chimeric antigen receptors (CARs) are synthetic receptors that combine the single chain variable fragment (scFv) obtained from a monoclonal antibody with the 5-chain signaling domain from the T cell receptor complex and costimulatory endodomains. Gene transfer of CARs into T cells redirects T cell antigen specificity through the scFv and promotes T cell activation and proliferation through costimulatory signals. The infusion of CAR-T cells (CAR-Ts) in patients with lymphoid malignancies has led to durable complete remission. However, up to 20% of patients with acute lymphoblastic leukemia receiving CD19-specific CAR-Ts relapse due to the emergence of leukemic clones that have lost the targeted epitope. Furthermore, the heterogeneity of tumor-associated antigen (TAA) expression in solid tumors leads to CAR-T treatment failure when a single TAA is targeted. Accordingly, the generation of multi-redirected CAR-Ts, namely by recognition of two non-overlapping epitopes of a TAA or two different TAAs, may be necessary to effectively eradicate tumor cells.

One major challenge in using a scFv-based antigen receptor is the need for multiple VH and VL domains to appropriately pair and stabilize in complex structures. In addition to the complexity and costs of manufacturing multiple T cell products, reduced expression of simultaneously expressed CARs, and compromised protein folding when several scFvs are linearly assembled in one single CAR format remain challenges to current methods of achieving multi redirected CAR-Ts.

SUMMARY

Provided herein are chimeric antigen receptors comprising a combination of single domain antibody mimics. The single domain antibody mimics may be monobodies, affibodies, or DARPins. The disclosed chimeric antigen receptors may recognize two different epitopes of the same tumor antigen. For example, the chimeric antigen receptor may recognize two different epitopes of HER-2 or EGFR. The disclosed chimeric antigen receptors may be recognize two epitopes of two different tumor antigens. For example, the chimeric antigen receptor may recognize HER-2 and EGFR. The disclosed chimeric antigen receptors may be expressed in immune cells for use in cancer immunotherapy.

BRIEF DESCRIPTION OF THE DRAWINGS

FIGS. 1A-1J show that Bi-EGFR.amR-Ts and conventional EGFR.CAR-Ts demonstrate comparable activity. (FIG. 1A-1C) Bio-layer Interferometry (BLI) was used to measure the affinity of the monomeric or heterodimeric single domain antibody mimics binding to recombinant Fc-EGFR on the FortéBio Octet system. 100 nM biotinylated antibody mimics were immobilized onto a streptavidin biosensor. Binding kinetics were measured against various concentrations of EGFR (0, 25, 50, 100 nM). The Kd was calculated based on kinetic fitting. FIG. 1D shows representative expression of the Bi-EGFR.amR, EGFR.CAR or CD19.CAR in T cells as assessed by flow cytometry. Activated T cells were transduced with retroviral vectors encoding the Bi-EGFR.amR, EGFR.CAR or CD19.CAR. With the exception of the CD19.CAR, all constructs were detected using an aFLAG Ab. The CD19.CAR was detected using an anti-idiotype Ab. Shaded and unshaded histograms indicate non-transduced and specific mAb, respectively. FIG. 1E shows a summary of amR or CAR expression (n=4). FIG. 1F shows expansion kinetics of Bi-EGFR.amR-Ts, EGFR.CAR-Ts or CD19.CAR-Ts NT (n=4). FIG. 1G shows phenotypic composition of Bi-EGFR.amR-Ts, EGFR.CAR-Ts or CD19.CAR-Ts 10 days post-transduction (n=4). FIG. 1H shows reducing and FIG. 1I shows non-reducing immunoblots of Bi-EGFR.amR-T and EGFR.CAR-T cell lysates. Immunoblots were probed with an α-CD3ξ. Ab. Upper panel and lower panels represent detection of the receptors and endogenous ξ chain, respectively. (FIG. 1J) EGFR. CAR-Ts and Bi-EGFR.amR-Ts incubated at the indicated time points with the α-FLAG Ab and cross-linked with a secondary Ab to induce the aggregation of the receptors. Cell lysates were immunoblotted to detect proximal (CD3ξp-Y142) and distal (Akt p-S473 and ERK p-T202/204) phosphorylation events following receptor cross-linking. Total CAR.CD3 ξ or amR. CD3 ξ and endogenous CD3 ξ were used as loading controls. Data are representative of 4 experiments.

(FIG. 3A) Expression of EGFR on BV173-WT and BV173-EGFR tumor cells following retroviral gene transfer with a retroviral vector encoding the full-length EGFR. Dotted and solid lines indicate isotype and α-EGFR Ab, respectively. (FIG. 3B) Bi-EGFR.amR-Ts or EGFR. CAR-Ts were co-cultured with BV173-WTor BV173-EGFRcells at 1:5 E: T for 3 days. CD19.CAR-T cells were used as a positive control. Cells were collected and T cells (CD3+) and tumor cells (CD19+) were quantified by flow cytometry. Representative flow plots are illustrated. (FIG. 3C) Quantification of BV173-WT or BV173-EGFR cells remaining after 3 days of co-culture (n=4), p<0.01 when comparing remaining BV173-WT and BV173-EGFR cells in EGFR.CAR-Ts and Bi-EGFR.amR-Ts. (FIG. 3D) Expression of EGFR on human pancreatic adenocarcinoma cell lines: AsPC-1, BxPC-3, HPAF-II and Panc-1 as detected by flow cytometry. Dotted and solid lines indicate isotype and α-EGFR Ab, respectively. The breast cancer tumor cell line MCF-7 was used as a negative control for EGFR expression.

FIGS. 4A-4H show that Bi-EGFR.amR-Ts demonstrate activity against EGFR-expressing tumor cells in vitro and in vivo. (FIG. 4A) Control T (NTs or CD19.CAR-Ts), Bi-EGFR.amR-Ts and EGFR.CAR-Ts were co-cultured with MCF-7 cells (EGFR negative) or EGFR-expressing pancreatic adenocarcinoma cell lines (AsPC-1, BxPC-3, HPAF-II and Panc-1) at 1:5 E: T. Cells were collected and quantified by flow cytometry on day 5. The frequency of residual tumor cells was identified as CD4-CD8-live cells (n=3-4), p<0.01 when Bi-EGFR.amR-Ts or EGFR.CAR-Ts are compared with control T cells. FIG. 4B shows IFN-γ and FIG. 4C shows IL-2 released in the co-culture supernatant by Bi-EGFR.amR-Ts, EGFR.CAR-Ts and control T cells after 24 hours of co-culture with tumor cells as assessed by ELISA (n=3-4), p<0.01 when Bi-EGFR.amR-Ts or EGFR.CAR-Ts are compared with control T cells. (FIG. 4D) bi-EGFR.amR-Ts, EGFR.CAR-Ts or control T cells were labeled with CFSE and stimulated with irradiated EGFR-expressing AsPC-1 cells at 4:1 E: T. Representative CFSE dilution on day 5. FIG. 4E shows proliferation index as assessed by CFSE dilution (n=4), p<0.01 when Bi-EGFR.amR-Ts or EGFR.CAR-Ts are compared with control T cells. FIG. 4F shows a schematic representation of a metastatic pancreatic cancer model in NSG mice using the FFLuc-labeled human Panc-1 cell line. Representative images of tumor bioluminescence (BLI) are shown in FIG. 4G and kinetics of tumor growth as assessed by BLI measurements are shown in FIG. 4H. Data are representative of two independent experiments with 5 mice per group; p<0.01 when Bi-EGFR.amR-T or EGFR.CAR-T cells are compared with control T cells.

(FIG. 5A) Representative expression of the AFF.EGFR.amR, FN3.EGFR.amR, EGFR.CAR or CD19.CAR on T cells as assessed by flow cytometry. With the exception of the CD19.CAR, all constructs were detected using α-FLAG Ab. The CD19.CAR was detected using an anti-idiotype Ab. Shaded and unshaded histograms indicate non-transduced and specific mAb, respectively. (FIG. 5B) AFF.EGFR.amR-Ts, FN3.EGFR.amR-Ts or EGFR.CAR-Ts were co-cultured with BV173-WT or BV173-EGFRcells at 1:5 E: T for 3 days. CD19.CAR-T cells were used as a positive control. Cells were collected and T cells (CD3+) and tumor cells (CD19+) were quantified by flow cytometry. Representative flow plots are illustrated. (FIG. 5C) Quantification of BV173-WT or BV173-EGFR cells remaining after 3 days of co-culture (n=4), p<0.01 when comparing remaining BV173-WT and BV173-EGFR in AFF.EGFR.amR-Ts, FN3.EGFR.amR-Ts and EGFR.CAR-Ts. (FIG. 5D) AFF.EGFR.amR-Ts, FN3.EGFR.amR-Ts or EGFR.CAR-Ts were co-cultured with EGFR-MCF-7 cells or EGFR+ pancreatic adenocarcinoma cell lines (AsPC-1, BxPC-3, HPAF-II and Panc-1) at 1:5 E: T. Cells were collected and quantified by flow cytometry on day 5. The frequency of residual tumor cells was identified as CD4-CD8-live cells (n=3-4), p<0.01 when AFF.EGFR.amR-Ts, FN3.EGFR.amR-Ts or EGFR.CAR-Ts are compared with control T cells. (FIG. 5E) IFN-γ and (FIG. 5F) IL-2 released in the co-culture supernatant by AFF.EGFR.amR-Ts, FN3.EGFR.amR-Ts or EGFR.CAR-Ts after 24 hours of co-culture with tumor cells as assessed by ELISA (n=3-4), p<0.01 when AFF.EGFR.amR-Ts, FN3.EGFR.amR-Ts or EGFR.CAR-Ts are compared with control T cells. (FIG. 5G) AFF.EGFR.amR-Ts, FN3.EGFR.amR-Ts or EGFR.CAR-Ts were labeled with CFSE and stimulated with irradiated EGFR+ AsPC-1 cells at 4:1 E: T. Representative CFSE dilution on day 5. (FIG. 5H) Proliferation index as assessed by CFSE dilution (n=4), p<0.01 when AFF.EGFR.amR-Ts, FN3.EGFR.amR-Ts or EGFR.CAR-Ts are comparedwith controlTcells.

(FIG. 6A) AFF.EGFR binding to rEGFRvIII. 100 nM FN3.EGFR and AFF.EGFR were applied to a streptavidin sensor immobilized with or without 100 nMrEGFRvIIIon anOctet QK. 0-60 sec: Baseline 1; 60660 sec: Loading; 660-840 sec: Baseline 2; 840-1440 sec: Association; 1440-2040 sec: Dissociation. The background was subtracted from the resulting binding curve. (FIG. 6B) Alanine substitutions were made to the alpha helices of the AFF scaffold to generate a mutated AFF.EGFR.amR (mAFF.EGFR.amR) and a BiEGFR.amR with a mutated AFF binding moiety (mBi-EGFR.amR). Representative expression of mAFF.EGFR.amR and mBi-EGFR.amR in T cells upon retroviral gene transfer. Dotted and solid lines indicate non-transduced and specific mAb, respectively. (FIG. 6C) Summary of CD69 expression on total live T cells (n=4), p<0.01 when comparing mBi-EGFR.amR-Ts seeded in EGFR WT and EGFRvIII-coated wells. (FIG. 6D) IFN-γ released in the supernatant by NT, mAFF.EGFR.amR-Ts and mBi-EGFR.amR-T cells as assessed by ELISA (n-4), p<0.01 when comparing mBi-EGFR.amR-Ts seeded in EGFRWTand EGFRvIIIcoatedwells.

FIG. 7A shows the representative expression of CD69 on NTs, AFF.EGFR.amR-Ts, FN3.EGFR.amR-Ts and Bi-EGFR.amR-Ts 6 hours post-stimulation with plate-bound rEGFR or rEGFRvIII protein as assessed by flow cytometry. Shaded and dashed histograms indicate media and PMA/Iono controls, respectively. Solid and dashed lines indicate rEGFR and rEGFRvIII protein stimulation, respectively. FIG. 7B shows a summary of CD69 expression on total live T cells (n=4), p<0.01 when comparing FN3.EGFR.amR-Ts seeded in rEGFR and rEGFRvIII-coated wells. FIG. 7C shows IFN-γ released in the supernatant by AFF.EGFR.amR-Ts, FN3.EGFR.amR-Ts and Bi-EGFR.amR-Ts as assessed by ELISA (n=3), p<0.01 when comparing FN3.EGFR.amR-Ts seeded in rEGFR and rEGFRvIII coated wells. FIG. 7D shows mAFF.EGFR.amR-Ts or mBi-EGFR.amR-Ts were co-cultured with BV173-WT or BV173-EGFR cells at 1:5 E: T for 3 days. CD19.CAR-T cells were used as a positive control. Cells were collected and T cells (CD3+) and tumor cells (CD19+) were quantified by flow cytometry. Representative flow plots are illustrated. FIG. 7E shows quantification of BV173-WT or BV173 EGFR cells remaining after 3 days of co-culture. FIG. 7F shows IFN-γ released in the supernatant by NT, CD19.CAR-T, mAFF.EGFR.amR-T and mBi-EGFR.amR-T cells as assessed by ELISA (n=2-4), p<0.01 when comparing the percentage of residual BV173-WT and BV173-EGFR cells remaining in the mBi-EGFR. amR-T wells.

FIG. 8A, FIG. 8B, and FIG. 8C show bio-layer Interferometry (BLI) used to measure the affinity of the monomeric or heterodimeric single domain antibody mimics binding to recombinant Fc HER2 using the FortéBio Octet system. 100 nM biotinylated antibody mimics were immobilized onto a streptavidin biosensor. Binding kinetics was measured against various concentrations of HER2 (0, 25, 50, 100 nM). The Kd was calculated based on kinetic fitting. (FIG. 8D) Control T (NT), Bi-HER2.amR-T and EGFR. CAR-T cells co-cultured with Panc-1 cells (HER negative) or HER2-expressing pancreatic adenocarcinoma cell lines (AsPC-1 and HPAF-II) at 1:5 E: T. Cells were collected and quantified by flow cytometry on day 5. The frequency of residual tumor cells was identified as CD4-CD8-live cells (n=3-6), p<0.01 when comparing Bi-HER2.amR-Ts or EGFR.CAR-Ts with NTs. FIG. 8E shows IFN-γ and FIG. 8F shows IL-2 released in the co-culture supernatant by NTs, Bi-HER2.amR-Ts or EGFR.CAR-Ts after 24 hours of co-culture with tumor cells as assessed by ELISA (n=3-6), p<0.01 when comparing Bi-HER2.amR-Ts or EGFR.CAR-Ts with NTs. FIG. 8G shows a schematic representation of a metastatic pancreatic cancer model in NSG mice using the using the FFLuc-labeled human HPAF-II cell line. Representative images of tumor bioluminescence (BLI) are shown in FIG. 8H and kinetics of tumor growth as assessed by BLI measurements are shown in FIG. 8I. Data are representative of two independent experiments with 5 mice per group; p<0.01 when Bi-HER2.amR-Ts or EGFR.CAR-Ts are compared with NTs.

FIG. 9A shows a schematic diagram of Bi-HER2.amR. Single domain antibody mimics (DARPin and AFF) identified to bind to HER2 were adapted to generate amRs that redirect T cell specificity for bi-epitopic recognition of HER2. Bi-HER2.amR was constructed with the CD8a hinge (H) and transmembrane domain (TM), the CD28 endodomain (28) and CD3ζ chain and cloned into the SFG retroviral vector. A 25-residue PQPQ linker (solid line) was included to separate the antigen-binding domains. A FLAG-tag was included after the 25-residue GGGGS linker (dashed line) to detect the expression of the amR on the cell surface of T cells by flow cytometry. (FIG. 9B) Activated T cells were transduced with a retroviral vector encoding the Bi-HER2.amR or EGFR. CAR. Expansion kinetics of T cells expressing the Bi-HER2.amR or EGFR.CAR (n=5). (FIG. 9C) Phenotypic composition of Bi-HER2.amR-Ts or EGFR.CAR-Ts 10 days post-transduction (n=5). (FIG. 9D) Expression of HER2 in human pancreatic adenocarcinoma cell lines. Panc-1 tumor cell line (Panc-1-WT) was modified to express HER2 by retroviral gene transfer (Panc-1-HER2). Dotted and solid lines indicate isotype and α-HER2 Ab, respectively. (FIG. 9E) Bi-HER2.amR-Ts or EGFR.CAR-Ts were co-cultured with Panc1-WT or Panc-1-HER2 cells at 1:5 E: T. On day 5, cells were collected and the frequency of residual tumor cells was identified by flow cytometry as CD4-CD8-live cells. Representative flow plots are illustrated.

FIG. 10A is a schematic diagram of bi-specific EGFR-HER2.amR. Single domain antibody mimics identified to bind to EGFR (FN3) and HER2 (DARPin) were adapted to generate amRs that redirect T cells for bi-specific recognition. Activated T cells were transduced with retroviral vectors encoding EGFR.amR, HER2.amR, EGFRHER2.amR or CD19.CAR. FIG. 10B shows representative expression of the EGFR.amR, HER2.amR, EGFRHER2.amR or CD19.CAR in T cells as assessed by flow cytometry. All constructs were detected using an α-FLAG Ab, while the CD19.CAR was detected using a specific anti-idiotype antibody. Shaded and unshaded histograms indicate non-transduced and specific mAb, respectively. FIG. 10C is a summary of receptor expression (n=3). FIG. 10D shows expansion kinetics of T cells expressing the EGFR.amR, HER2.amR or EGFRHER2.amR (n=3). FIG. 10E shows the phenotypic composition of T cells expressing the EGFR.amR, HER2.amR or EGFRHER2.amR 10 days post-transduction (n=3). FIG. 10F is a summary of CD69 expression on total live T cells (n=1-3), p<0.01 when comparing EGFR.amR-Ts and HER2.amR-Ts seeded in rHER2 and rEGFR-coated wells, respectively. FIG. 10G shows IFN-γ released in the supernatant by EGFR.amR-Ts, HER2.amR-Ts and EGFRHER2.amR-T cells as assessed by ELISA (n=1-3), p<0.01 when comparing EGFR.amR-Ts and HER2.amR-Tsseeded in rHER2 andrEGFR-coated wells, respectively. FIG. 10H shows expression of EGFR and HER2 in BV173-WT, BV173-EGFR and BV173-HER2 tumor cells. BV173-EGFR and BV173-HER2 cells were obtained upon retroviral gene transfer of thefull length EGFR or atruncated form of HER2 to be devoid of a cytoplasmic domain,respectively. Dottedand solid lines indicate isotype andspecificAbs, respectively.

FIGS. 11A-11I show EGFR-HER2.amR-Ts show dual specificity. Co-culture experiment in which T cells were plated with its respective BV173 target cells, and 3 days later T cells were collected and re-plated with the same BV173 tumor cell line or BV173 cells expressing the non-specific target. FIG. 11A shows schema of the repetitive co-culture experiments with control (CD19.CAR-Ts), monospecific FN3.EGFR.amR-Ts, DARPin.HER2.amR-Ts and bispecific EGFR-HER2.amR-Ts all plated at 1:2 E: T. FIG. 11B shows representative flow plots of the repetitive co-culture experiments on the second round. Cells were collected and quantified by flow cytometry on day 3. The frequency of residual tumor cells was identified as CD3-CD19+ live cells. FIG. 11C shows quantification of tumor cells remaining after the second co-culture (n=2-3), p<0.01 when comparing FN3.EGFR.amR-Ts and DARPin.HER2.amR-Ts and their respective targets against WT tumor cells. FIG. 11D shows IFN-γ released in the co-culture supernatant by CD19.CAR-Ts, FN3.EGFR.amR-Ts, DARPin. HER2-amR-Ts or EGFR-HER2.CAR-Ts after 24 hours of co-culture with tumor cells as assessed by ELISA (n=23), p<0.01 when comparing FN3.EGFR.amR-Ts and DARPin.HER2.amR-Ts and their respective targets against WT cells. FIG. 11E shows schematic representation of the re-challenge tumor model in NSG mice using the EGFR+ HER2-human Panc-1 cell line labeled with the FF-Luc and the EGFR-HER2 human BV173-HER2 cell line. Representative images of the Pan-1 tumor BLI are shown in FIG. 11F and BLI kinetics of tumor growth are shown in FIG. 11G. FIG. 11I shows the survival curve of NSG mice after re-challenge with the BV173-

Figure 1E:
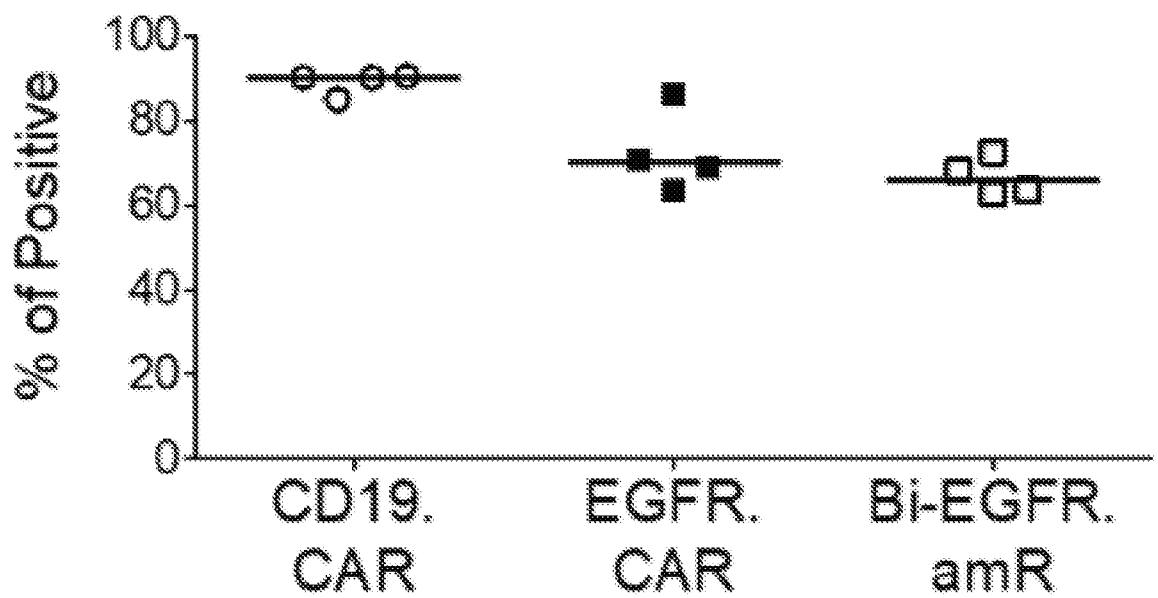

HER2 cell line; p<0.01 when EGFR.amR-Ts treated mice are compared with EGFR-HER2.amR-Ts treated mice.

DETAILED DESCRIPTION

Disclosed herein are chimeric antigen receptors and methods of their use. Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. Many embodiments herein are described using open "comprising" language. Such embodiments encompass multiple closed "consisting of" and/or "consisting essentially of" embodiments, which may alternatively be claimed or described using such language. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "antibody mimic" or "antibody mimetic" as used interchangeably herein refers to compounds that specifically bind antigens, but that are not structurally related to antibodies. Antibody mimetics are generally artificial peptides or proteins with a molar mass of between 3 kDa and 30 kDa.

The term "Chimeric Antigen Receptor" or alternatively a "CAR" refers to a recombinant polypeptide construct comprising at least an extracellular antigen binding moiety, a transmembrane domain and a cytoplasmic signaling domain (also referred to herein as "an intracellular signaling domain").

The term "monobody" refers to an antibody mimetic that comprises a fibronectin type III domain (FN3) as a molecular scaffold. Monobodies are produced from combinatorial libraries in which portions of the FN3 scaffold are diversified using highly tailored mixtures of amino acids by utilizing phage display and yeast surface display techniques. These techniques have successfully generated a large number of monobodies that have high affinity and high specificity to their respective targets. Monobodies and methods of generating monobodies are further described in, for example, PCT/US2007/078039, U.S. Pat. No. 6,673,901, and PCT/US2011/046160, which are incorporated by reference.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

"Sample," "test sample," "specimen," "sample from a subject," and "patient sample" as used herein may be used interchangeable and may be a sample of blood, such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Sequence identity" refers to the degree two polymer sequences (e.g., peptide, polypeptide, nucleic acid, amino acid, etc.) have the same sequential composition of monomer subunits. The term "sequence similarity" refers to the degree with which two polymer sequences (e.g., peptide, polypeptide, nucleic acid, amino acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

The term "signaling domain" refers to the functional portion of a protein which acts by transmitting information within the cell to regulate cellular activity via defined signaling pathways by generating second messengers or functioning as effectors by responding to such messengers.

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Substantially" as used herein means that the recited characteristic, parameter, and/or value need not be achieved exactly, but that deviations or variations, including for example, tolerances, measurement error, measurement accuracy limitations and other factors known to skill in the art, may occur in amounts that do not preclude the effect the characteristic was intended to provide. A characteristic or feature that is substantially absent (e.g., substantially non-luminescent) may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic (e.g., luminescent intensity of a bioluminescent protein or bioluminescent complex).

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid (e.g., replacing an amino acid with a different amino acid of similar properties, such as hydrophilicity, degree, and distribution of charged regions) is recognized in the art as typically involving a minor change. These minor changes can be identified, in part, by considering the hydropathic index of amino acids, as understood in the art. The hydropathic index of an amino acid is based on a consideration of its hydrophobicity and charge. It is known in the art that amino acids of similar hydropathic indexes can be substituted and still retain protein function. In one aspect, amino acids having hydropathic indexes of +2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions may be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Chimeric Antigen Receptors

The present disclosure provides chimeric antigen receptors. The chimeric antigen receptors comprise an extracellular tumor antigen binding moiety comprising a first binding domain and a second binding domain; a hinge, a transmembrane domain, and an intracellular cytoplasmic domain.

In some embodiments, the chimeric antigen receptor is a biepitopic chimeric antigen receptor that binds to two separate epitopes of a single tumor antigen. For example, the first binding domain may bind to a first epitope of a first tumor antigen and the second binding domain may bind to a second epitope of the first tumor antigen. The first tumor antigen may be any desired tumor antigen. Suitable tumor antigens include, for example, EGFR, EGFRvIII, HER2, HER3, HER4, c-MET, CAIX, EpCAM, FOLR1, GD2, HGFR, VEGFR, PDGFR, ROR1, IL13RA2, insulin-like growth factor receptor, prostate specific membrane antigen, mesothelin (MSLN), mucin-1, B7-H1, B7-H3, B7-H4, B7-H5, B7-H6, B7-H7, interleukin 6 receptor, NY-ESO-1, alpha fetoprotein (AFP), glypican-3 (GPC3), BAFF-R, BCMA, TACI, LeY, CD5, CD13, CD14, CD15 CD19, CD20, CD22, CD30, CD33, CD38, CD41, CD45, CD61, CD64, CD68, CD70, CD117, CD123, CD138, CD267, CD269, CD38, Flt3 receptor, and CS1. For example, the first tumor antigen may be EGFR. Alternatively, the first tumor antigen may be HER-2.

In other embodiments, the chimeric antigen receptor is a bispecific chimeric antigen receptor that binds to two different tumor antigens. For example, the first binding domain may bind to an epitope of a first tumor antigen and the second binding domain may bind to an epitope of a second tumor antigen. The first and second tumor antigens may be any suitable tumor antigens as described above. Suitable tumor antigens include, for example, EGFR, EGFRVIII, HER2, HER3, HER4, c-MET, CAIX, EpCAM, FOLR1, GD2, HGFR, VEGFR, PDGFR, ROR1, IL13RA2, insulin-like growth factor receptor, prostate specific membrane antigen, mesothelin (MSLN), mucin-1, B7-H1, B7-H3, B7-H4, B7-H5, B7-H6, B7-H7, interleukin 6 receptor, NY-ESO-1, alpha fetoprotein (AFP), glypican-3 (GPC3), BAFF-R, BCMA, TACI, LeY, CD5, CD13, CD14, CD15 CD19, CD20, CD22, CD30, CD33, CD38, CD41, CD45, CD61, CD64, CD68, CD70, CD117, CD123, CD138, CD267, CD269, CD38, Flt3 receptor, and CS1. For example, the first tumor antigen may be EGFR and the second tumor antigen may be HER-2.

The first and second binding domain comprise single domain antibody mimics. The single domain antibody mimic may bind to any desired epitope of any desired tumor antigen. Three single domain antibody mimics are of particular interest for developing CARs with multiple tumor-targeting features: 1) monobody, based on the type III domain of fibronectin (FN3); 2) affibody, based on a three-helix bundle Z domain; 3) DARPin, based on the designed ankyrin repeat protein. Significantly, these engineered proteins can have high specificity and affinity, despite their simple structures and relatively small size. The FN3 domain is a highly stable protein with a MW around 10 kDa. Structurally, it has a β-sandwich scaffold similar to that of the immunoglobulin VH domain, with putative ligand-binding sites composed of three solvent accessible surface loops that are structurally analogous to the CDR H1, H2, and H3 of the VH domain. The advantage of the FN3 domain is in their lack of disulfide bonds and post-translational modifications for biological functions. Affibodies (AFF) are based on the three-helix bundle Z domain derived from Staphylococcal protein A. Similar to the FN3 domain, AFF domains are also highly stable against both proteolysis and heat-induced denaturation and lack disulfide bonds. Finally, DARPins or leucine-rich repeats in lamprey antibodies contain consecutive copies of small structural repeats, which stack together to form a contiguous interacting surface.

The first and second binding domain may each comprise an entity that is independently selected from a monobody, an affibody, and a DARPin. For example, the first binding domain may comprise a monobody and the second binding domain may comprise an affibody. In some embodiments, the first binding domain may comprise a monobody that binds to a first epitope of EGFR and the second binding domain may comprise an affibody that binds to a second epitope of EGFR.

In other embodiments, the first binding domain may comprise a DARPin and the second binding domain may comprise an affibody. For example, the first binding domain may comprise a DARPin that binds to a first epitope of HER-2 and the second binding domain may comprise an affibody that binds to a second epitope of HER-2.

In some other embodiments, the first binding domain may comprise a monobody that binds to an epitope of a first tumor antigen and the second binding domain may comprise a DARPin that binds to an epitope of a second tumor antigen. For example, the first binding domain may comprise a monobody that binds to an epitope of EGFR and the second binding domain may comprise a DARPin that binds to an epitope of HER-2.

The first and second binding domains may be separated by a linker. The linker may be any suitable length. For example, the first and second binding domains may be separated by a linker of about 25 residues. For example, the linker may be 20 residues to 30 residues. For example, the linker may be 21 residues, 22 residues, 23 residues, 24 residues, 25 residues, 26 residues, 27 residues, 28 residues, 29 residues, or 30 residues. In some embodiments, the linker may be a PQPQ linker. For example, the linker may be a 25-residue PQPQ linker.

In some embodiments, the extracellular tumor antigen binding moiety comprises the amino acid sequence of SEQ ID NO: 1. In other embodiments, the extracellular tumor antigen binding moiety comprises the amino acid sequence of SEQ ID NO: 2. In other embodiments, the extracellular tumor antigen binding moiety comprises the amino acid sequence of SEQ ID NO: 3. In some embodiments, the extracellular tumor antigen binding moiety comprises an amino acid sequence having at least 80% sequence identity (e.g. 80%, 85%, 90%, 91%, 92%, 93%, 94%, 95%, 96%, 97%, 98%, 99%, or 100%) to SEQ ID NO: 1, SEQ ID NO: 2, or SEQ ID NO: 3.

The chimeric antigen receptors disclosed herein further comprise a transmembrane domain. The transmembrane domain may be from any suitable protein. For example, the transmembrane domain may be a CD8a transmembrane domain.

The extracellular tumor antigen binding moiety is connected to the transmembrane domain by a hinge. The hinge may be from any suitable protein. For example, the hinge may be from a human protein. For example, the hinge may be a CD8a hinge. The hinge may be any suitable number of residues. For example, the hinge may be a 45 residue CD8a hinge.

The chimeric antigen receptor further comprises an intracellular cytoplasmic domain. The intracellular signaling domain comprises a functional signaling domain derived from a stimulatory molecule. For example, the intracellular signaling domain may comprise CD3 zeta signaling domain. The intracellular signaling domain may further comprise a co-stimulatory domain. For example, the intracellular signaling domain may comprise a co-stimulatory domain from CD28.

The chimeric antigen receptor may comprise a polypeptide having at least 90% sequence identity to SEQ ID NO:4, SEQ ID NO: 5, or SEQ ID NO:6. For example, the chimeric antigen receptor may comprise a polypeptide having at least 90%, at least 91%, at least 92%, at least 93%, at least 94%, at least 95%, at least 96%, at least 97%, at least 98%, or at least 99% sequence identity to SEQ ID NO: 4, SEQ ID NO: 5, SEQ ID NO: 6.

Further disclosed herein are engineered immune cells expressing the chimeric antigen receptors disclosed herein. The disclosed chimeric antigen receptors may be introduced into any desired immune cell. For example, the chimeric antigen receptor may be introduced into a T-cell for use in T-cell directed therapy.

Further disclosed herein are methods for treating cancer. The methods comprise administering to a patient in need thereof a therapeutically effective amount of a composition comprising an engineered immune cell comprising a chimeric antigen receptor as disclosed herein. The cancer may be any suitable cancer. For example, the cancer may be bladder cancer, breast cancer, cervical cancer, extrahepatic cancer, intrahepatic cancer, colorectal cancer, esophageal cancer, esophagogastric junction cancer, gallbladder cancer, gastric adenocarcimona, gastrointestinal stromal cancer, glioblastoma, glioma, head and heck carcinoma, hepatocellular carcinoma, intestinal cancer, kidney cancer, lung cancer (non-small cell lung cancer, small cell lung cancer), lymphoma, melanoma, neuroendocrine cancer, oligodendroglioma, ovarian cancer (epithelial or non-epithelial), pancreatic adenocarcinoma, penile cancer, pituitary cancer, prostate cancer, sarcoma, solitary fibrous tumors, testicular cancer, thymic cancer, thyroid cancer, or uterine cancer. The cancer may be a HER-2 positive cancer and/or an EGFR-positive cancer.

3. EXAMPLES

It will be readily apparent to those skilled in the art that other suitable modifications and adaptations of the methods of the present disclosure described herein are readily applicable and appreciable and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Materials and Methods

Construction of biepitopic and bispecific CAR vectors: To construct biepitopic or bispecific CAR vectors, the codon-optimized (for expression in human cells) coding regions for a monomeric or heterodimeric EGFR- or/and HER2-binding ligand were fused through an optimized flexible linker. The final coding region was cloned into the SFG vector, resulting in a fusion protein that is composed of the signaling peptide from human IgG heavy chain, EGFR- or HER2-binding domain(s), a FLAG tag, a 45-residue hinge region from human CD8a extracellular domain, the transmembrane domain of human CD8 a, the CD28-costimulatory endodomain, and the & chain of the TCR/CD3 complex. The CD8a hinge and transmembrane domains contain the native cysteine residues. Single domain antibody mimics (AFF, DARPin and FN3) were PCR amplified and cloned into the SFG vector. The scFv derived from the Cetuximab mAb was PCR amplified and cloned into the SFG vector. EGFR WT (Addgene plasmid #110110) and pBABE-puro-ErbB2 (Addgene plasmid #40978) were gifts from Matthew Meyerson. Full-length EGFR and HER2 were amplified by PCR and cloned into the SFG retroviral vector. A truncated form of HER2 lacking an intracellular domain was amplified by PCR and also cloned into the SFG retroviral vector.

Expression and purification of recombinant EGFR and HER2 binding protein domains: Coding sequences codon-optimized for expression in E. coli with a C-terminal His tag were cloned into the pET28b vector. To express the ligands, vectors were transformed into E. coli BL21 (DE3) Rosetta cells and positive clones were selected on LB plates containing 50 µg/mL kanamycin and 34 µg/mL chloramphenicol. Single colonies were picked and grown overnight at 37° C. Overnight cell cultures were added to 1 L of LB media and grown at 37° C. When the OD 600 was between 0.6-0.8, 1 mM IPTG was added to induce expression for 4 h at 37° C. To purify the binding ligands, the cell pellet was resuspended in buffer A (25 mM HEPES pH 7.4 and 300 mM NaCl) supplemented with 1 mM phenylmethylsulfonyl fluoride (PMSF) and sonicated on ice for 10 min on a Sonifier 450 sonicator (Branson). After cell lysis, the soluble fraction was recovered by centrifugation at 4° C. The resulting soluble fraction was loaded onto an IMAC Ni-charged affinity column (Bio-Rad) pre-equilibrated with buffer A. The column was washed with Buffer A containing 20 mM imidazole (Buffer B) and then 50 mM imidazole (Buffer C) and the proteins were eluted with buffer D (buffer A and 200 mM imidazole). Following dialysis against 1×PBS, the quality of the purified proteins was verified by SDS-PAGE.

Characterization of target-binding features: BLI analyses of the monomeric and heterodimeric EGFR and HER2-binding domains were performed on a Octet QK system (FortéBio LLC., Menlo Park, CA) against recombinant EGFR-Fc and HER2-Fc (AcroBiosystems, Newark, NJ) using 96-well microplates (Greiner Bio-One) at 30° C. Streptavidin biosensors (FortéBio) were used to immobilize concentrations of biotinylated ErbB binding domains and samples resuspended in an assay buffer (1×PBS, 1% BSA, 0.05% Tween 20, pH 7.4) were applied to the 96-well microplate. Assays run in triplicate were acquired and analyzed on the FortéBio Data Acquisition 6.4 software. Savitzky-Golay filtering was applied to the averaged reference biosensors and then globally fitted at a 1:1 model.

Cell lines: Tumor cell lines Panc-1, BxPC-3, HPAF-II and AsPC-1 (pancreatic cancer), MCF-7 (breast cancer), BV173 (B cell lymphoma) were purchased from American Type Culture Collection (ATCC). BxPC-3 and BV173 were cultured in RPMI1640 (Gibco). AsPC-1 was cultured in RPMI1640 supplemented with 1 mM sodium pyruvate (Gibco). HPAF-II and MCF-7 were cultured in MEM (Gibco). Panc-1 was cultured in DMEM (Gibco). All media were supplemented with 10% FBS (Sigma), 2 mM GlutaMax (Gibco) and penicillin (100 units/mL) and streptomycin (100 mg/mL) (Gibco). All cells were maintained at 37° C. with 5% CO2. Panc-1 cells were transduced with a retroviral vector encoding the eGFP-Firefly-Luciferase (eGFP-FFluc) gene. BV173 cells were transduced with a retroviral construct encoding full-length human EGFR to generate BV173-EGFR cells or a truncated form of HER2 to generate BV173-HER2 cells. Panc-1 cells were transduced with a retroviral vector encoding HER2 to make Panc-1 HER2. All cell lines were regularly tested for *mycoplasma* and the identity of the cell lines were validated by flow cytometry for relevant cell surface markers.

Generation of redirected T cells: T cells expressing CAR and amRs were generated in accordance to standard operating procedures currently used to manufacture CAR-Ts for clinical use at the University of North Carolina. Peripheral blood mononuclear cells (PBMCs) were isolated from discharged buffy coats (Gulf Coast Regional Blood Center, Houston, TX) using Lymphoprep medium (Accurate Chemical and Scientific Corporation) and activated on plates coated with 1 µg/mL CD3 (Miltenyi Biotec, Bergisch Gladback, Germany) and CD28 (BD Biosciences, San Jose, CA) mAbs. Activated T cells were transduced with retroviral supernatants on retronectin coated 24-well plates (Takara Bio Inc., Shiga, Japan) 2-3 days post-activation. Transduced T cells were expanded in 50% Click's Medium (Irvine Scientific, Santa Ana, CA) and 50% RPMI 1640 supplemented with 10% Hyclone FBS (GE Healthcare, Chicago, IL), 2 mM GlutaMax (Gibco) and penicillin (100 units/mL) and streptomycin (100 mg/mL) (Gibco) with 10 ng/mL IL-7 and 5 ng/mL of IL-15 (Peprotech, Rocky Tech, NJ) for 10-14 days of culture before being used for functional assays.

Flow cytometry: mAbs specific for human CD3 (APC-H7; SK7; 560176), CD45 (BV510; HI30; 563204), CD4 (BV711; SK3; 563028), CD8 (APC; SK1; 340584), CD19 (FITC; SJ25C1; 340409), CD45RA (PE; HI100; 555489), CD45RO (BV786; UCHL1; 564290), CD69 (FITC; L78; 347823), HER2 (PE; Neu24.7; 340879) from BD Biosciences (San Jose, CA), CCR7 (FITC; 150503; FAB197F-100) from R&D (Minneapolis, MN) and EGFR (PE; AY13; 352904) from BioLegend (San Diego, CA) were used. Expression of the EGFR.CAR or amRs was detected using α-FLAG mAb (APC; L5; 637308). An anti-idiotype mAb was used to detect the expression of the CD19.CAR. All samples were acquired on a BD LSRFortessa and a minimum of 10,000 events was acquired per sample. Samples were analyzed on FlowJo 9 (FlowJo LLC, Ashland, OR).

Western Blot analysis. T cell lysates were resuspended in 2× Laemelli Buffer (Bio-Rad) in reducing or non-reducing conditions. To assess signaling through the CAR or amR, T cells on ice were incubated with 1 µg of α-FLAG Ab (clone M2) for 15 minutes and then 1 µg of goat α-mouse secondary Ab (BD Biosciences, San Jose, CA) for an additional 15 minutes. Cells were then transferred to a 37° C. water bath for the indicated time points and lysed with 4× Laemelli buffer. All lysates were separated in 4-15% sodium dodecyl sulfate polyacrylamide (SDS-PAGE) gels and transferred to polyvinylidene diflouride membranes (all Bio-Rad). Blots were probed for human CD3ξ (Santa Cruz Biotechnology, Dallas, TX), p-Y142 CD3ξ (Abcam, Cambridge, MA), pan-ERK (BD Biosciences) and pan-Akt, p-S473 Akt and p-T202/Y204 MAPK (all Cell Signaling, Danvers, MA) diluted 1:1000 in TBS-Tween/5% skim milk. Membranes were then incubated with HRP-conjugated goat α-mouse or goat α-rabbit IgG (both Santa Cruz) at a dilution of 1:3000 and imaged using the ECL Substrate Kit on a ChemiDoc MP System (both Bio-Rad) according to manufacturer's instructions.

In vitro activation. Biotinylated recombinant EGFR and EGFRvIII protein (AcroBiosystems) were added to 96-well plates coated with 1 µg of avidin (Thermo Fisher Scientific) at a 3:1 ratio. Recombinant EGFR-Fc and HER2-Fc (R&D Systems) were coated on 96-well plates overnight at a concentration of 1 µg/well. T cells were seeded in duplicate or triplicate for 6 hours and supernatant was collected for IFNγ and T cells were assessed for CD69 by flow cytometry.

Proliferation assay. T cells were labeled with 1.5 mM carboxyfluorescein diacetate succinimidyl ester (CFSE) (Invitrogen) and plated with irradiated AsPC-1 at 4:1 E: T in the absence of exogenous cytokines. CFSE dilution of CAR+ or amR+ T cells was analyzed on day 5 using flow cytometry. The proliferation index was quantified using FlowJo 9.

Long-term in vitro cytotoxicity. Tumor cells were seeded at $2.5 \times 10^5$ per well in 24-well plates. Donor-matched T cells normalized for transduction efficiency were added at 1:5 effector to target (E: T) ratio. On day 5 of co-culture, cells were collected, and the frequency of T cells and residual tumors cells was measured by flow cytometry. Tumor cells were identified as CD19+ for BV173 tumor cells or CD4-CD8- in the case of all adherent tumor cell lines.

Repetitive co-culture assay. For multiple rounds of co-culture, tumor cells were seeded at $5 \times 10^5$ per well in 24-well plates. Donor-matched T cells normalized for transduction efficiency were added at 1:2 effector to target (E: T) ratio. On day 3 of co-culture, a fraction of the cells were collected and the frequency of T cells and residual tumors cells were measured by flow cytometry. Between co-cultures, T cells were washed and resuspended in fresh medium, without the addition of exogenous cytokines, and left to rest for 3 days.

Cytokine analysis. Supernatant was collected from $5 \times 10^4$ CAR-Ts or amR-Ts plated in in vitro cytotoxicity assays at 1:5 E:T ratio after 24 hours. IFN-γ and IL-2 levels were measured by ELISA per manufacturer's instructions (R&D) in duplicate.

Xenograft murine models. Six to eight-week-old male or female non-obese diabetic severe combined immunodeficiency/yc/-(NSG) mice were injected with the Panc-1 tumor cell line ($1 \times 10^6$ cells/mouse) transduced with the GFP-FFLuc reporter intravenously by tail vein (iv.) injection. In other experiments HPAF-II GFP-FFLuc tagged cells were suspended in Matrigel and inoculated intraperitoneally (ip.) ($1 \times 10^6$ cells/mouse). In re-challenge experiments Panc-1 GFP-FFLuc cells ($1 \times 10^6$ cells/mouse) were injected 10 days prior to T cell injection. Upon clearance of the Panc-1 tumor cells, mice were then infused with BV173-HER2 cells ($2 \times 10^6$ cells/mouse). Mice were matched based on the bioluminescence intensity and injected with $5 \times 10^6$ or $1 \times 10^7$ T cells iv 12-14 days post tumor cell engraftment. The IVIS-Kinetic Optical System (Perkin Elmer, Waltham, MA) was used to monitor tumor burden. Mice were monitored and euthanized according to UNC-IACUC Standards.

Statistical Analysis. Data are reported as the mean and standard deviation, unless otherwise reported. To compare significant differences between 2 samples a two-tailed Student's t-test was applied. An ANOVA with Bonferroni's post-hoc analysis was applied when a comparison between multiple groups was required. A p value of less than 0.05 was considered statistically significant. All figures were generated using GraphPad Prism (GraphPad Software, La Jolla, CA).

Example 2

Experimental Results

Generation and characterization of soluble single domain antibody mimics targeting EGFR in a biepitopic manner. To develop a single domain-based tumor antigen binding moiety that targets two different epitopes of EGFR, the previously identified Z domain-based EGFR-binding affibody ZEGFR: 1907 and an FN3-based EGFR-binding monobody were assembled. To retain the target-binding affinity, specificity, and independent folding of each EGFR-binding domain, the length and flexibility of the linker between the two EGFR-binding domains were carefully tuned and optimized. It was observed that when the linker is too short, the target binding of both domains was abolished. Similarly, the use of a longer linker resulted in the loss of the bivalent effect, as well as instability of the ligands. In this study, the two antigen-binding moieties were separated by a 25-residue flexible linker. The resulting biepitopic affinity molecule, referred to as Bi-EGFR, binds to the extracellular domain of human EGFR at two non-overlapping epitopes with an affinity (Kd) around 0.38+0.07 nM (FIG. 1A), which is approximately 10-time higher than that of the monomeric EGFR-binding FN3 domain (FN3.EGFR: 3.1+0.9 nM, FIG. 1B) or Z domain (AFF.EGFR: 3.2+0.3 nM, FIG. 1C).

Figure 1F:
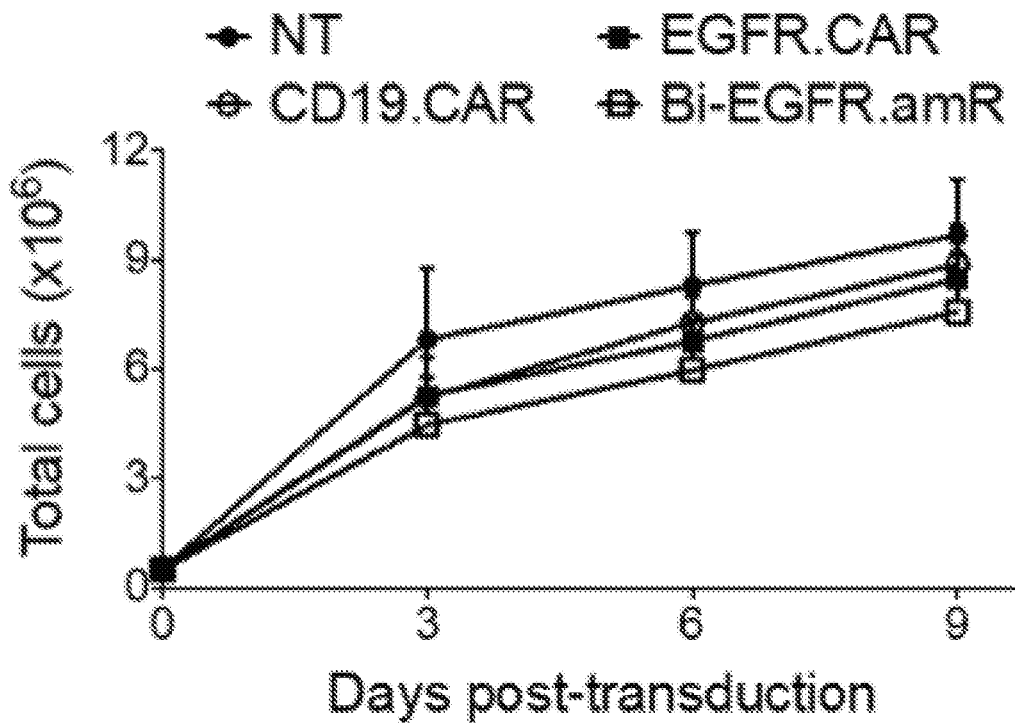
Figure 1G:
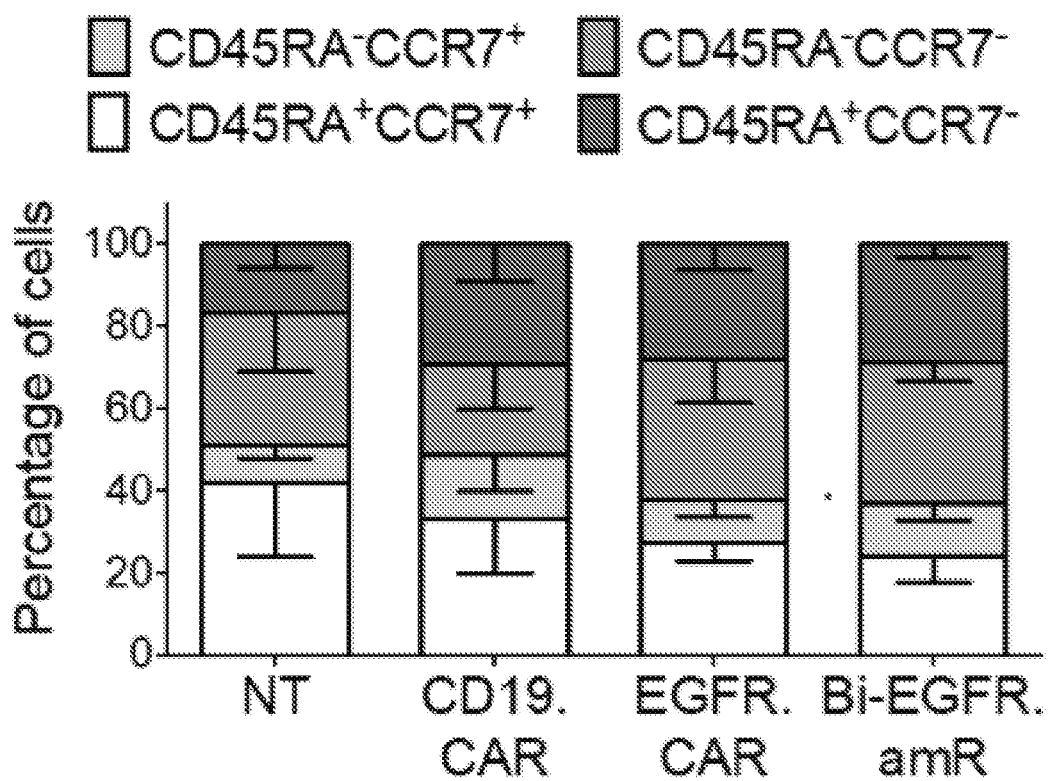
Figures 1H, 1I:
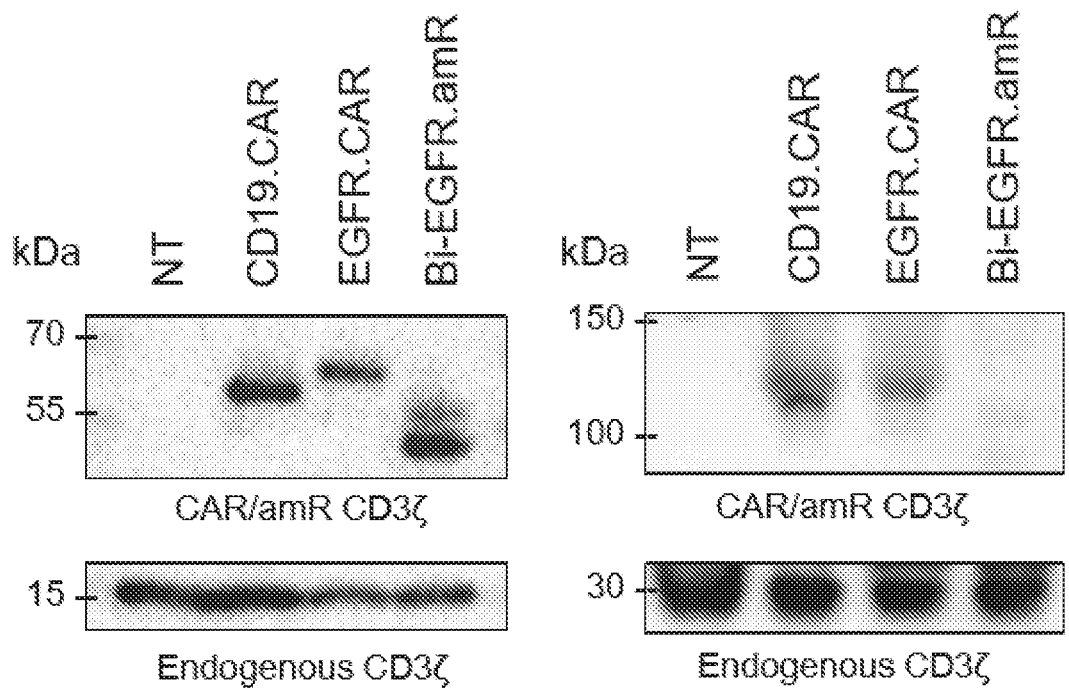
Figure 1J:
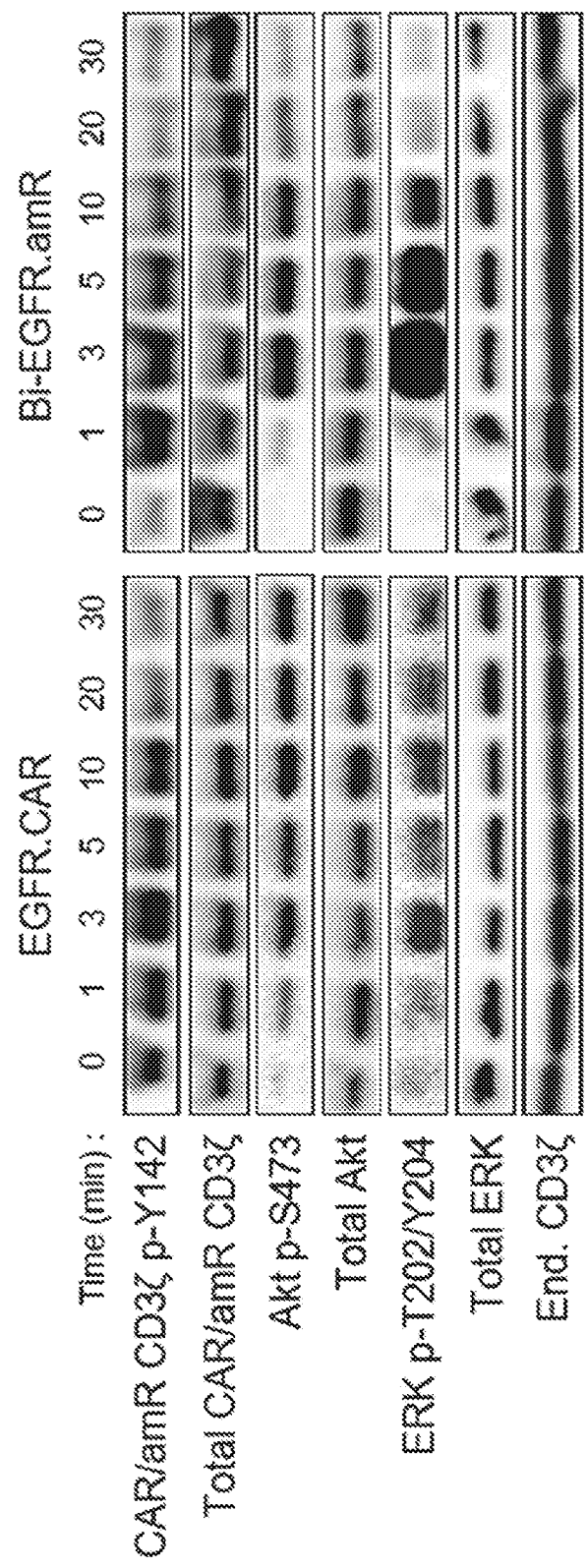
Figure 2:
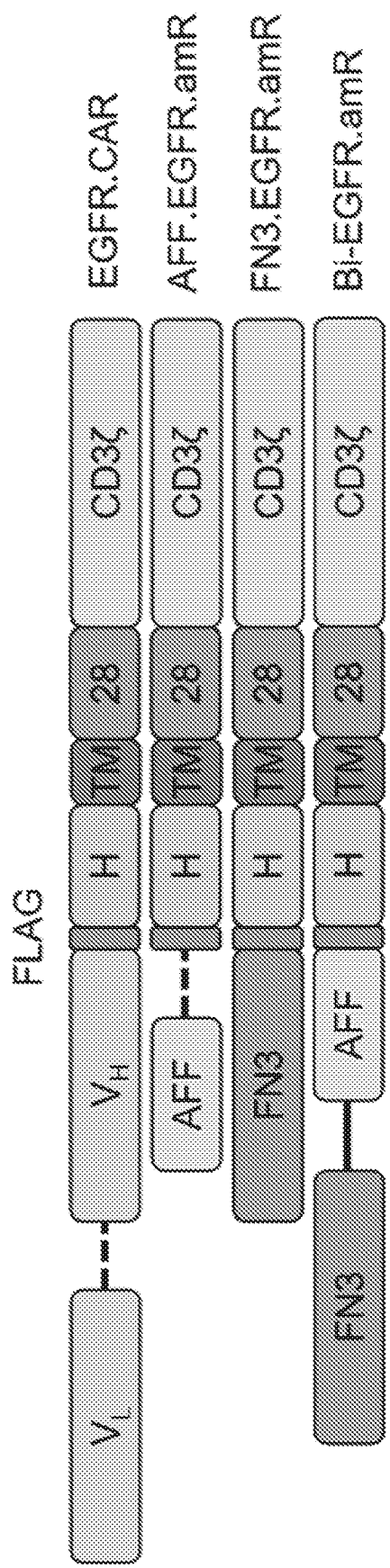
FIG. 2 shows a schematic diagram of antibody mimics receptors (amRs) targeting EGFR. Single domain antibody mimics (AFF and FN3) identified to bind to EGFR were adapted to generate amRs. All amRs were constructed with the CD8a hinge (H) and transmembrane domain (TM), the CD28 endodomain (28) and CD35 chain and cloned into the SFG retroviral vector. A 25-residue PQPQ linker (solid line) was included to separate the antigen-binding domains of the bi-epitopic amR (Bi-EGFR.amR). A FLAG-tag was included after the 25-residue GGGGS linker (dashed line) to detect the expression of the amR on the cell surface of T cells by flow cytometry. A conventional EGFR-specific chimeric antigen receptor (EGFR.CAR) was generatedusing thescFvfromtheCetuximab mAb.

T cells expressing the Bi-EGFR.amR are comparable to T cells expressing a conventional EGFR-specific CAR. To construct the CAR vector, the sequence of biochemically optimized Bi-EGFR was fused to the CD28 and CD3 ξ-chain signaling domains via the CD8a hinge and transmembrane domains. To detect the expression of the Bi-EGFR.amR in T cells (Bi-EGFR.amR-Ts) following transduction, a FLAG-tag was included in the Bi-EGFR.amR cassette (FIG. 2). A conventional EGFR-specific CAR (EGFR.CAR) generated using the scFv derived from Cetuximab (FIG. 2), and the CD19-specific CAR (CD19.CAR) were used as controls. AmRs composed of either the EGFR-A binding moiety (FN3.EGFR.amR) or the EGFR-B binding moiety (AFF.EGFR.amR) alone were also constructed (FIG. 2). Upon retroviral gene transfer, T cells stably expressed the Bi-EGFR.amR (FIG. 1D,E), expanded in vitro in response to exogenous cytokines (FIG. 1F), and maintained T cell composition comparable to EGFR.CAR-Ts and CD19.CAR-Ts (FIG. 1G). Western blot (WB) analysis of lysates from Bi-EGFR.amR-Ts detecting the CD3 ξ chain under reducing conditions showed the native &-chain (17 kDa) and a band at the expected size of 55 kDa, indicating the integrity of the assembled Bi-EGFR.amR (FIG. 1H). Under non-reducing WB conditions formation of dimers and multimers in both CD19.CAR-Ts and EGFR.CAR-Ts occurred, demonstrating the potential self-aggregation of CAR molecules in CAR-Ts in the absence of antigen binding (FIG. 1I). In contrast, Bi-EGFR.amRs multimers were less evident, suggesting that the relatively simple and rigid structure of antibody mimics may reduce the possibility of self-aggregation even when these molecules are assembled with T cell signaling moieties (FIG. 1I). Proximal and distal signaling in EGFR.CAR-Ts and Bi-EGFR.amR-Ts upon receptor cross-linking was then analyzed. As shown in FIG. 1J, receptor cross-linking in both Bi-EGFR.amR-Ts and EGFR.CAR-Ts triggered similar phosphorylation of proximal (CD3° C.) and distal (Akt and ERK) signaling molecules.

Figure 3A:
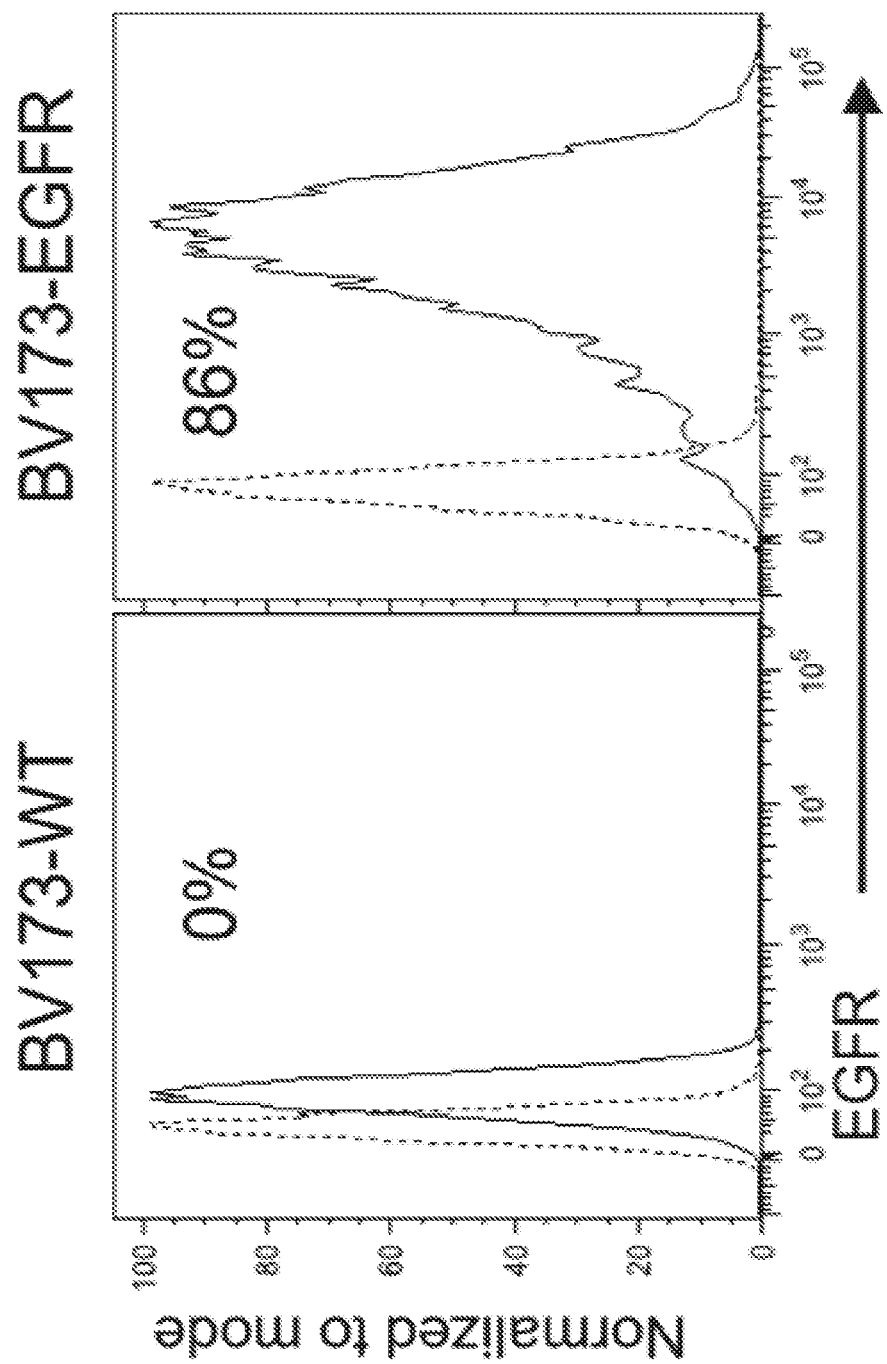
FIGS. 3A-3D show Bi-EGFR-amR-Ts show specificity for EGFR.
Figure 3B:
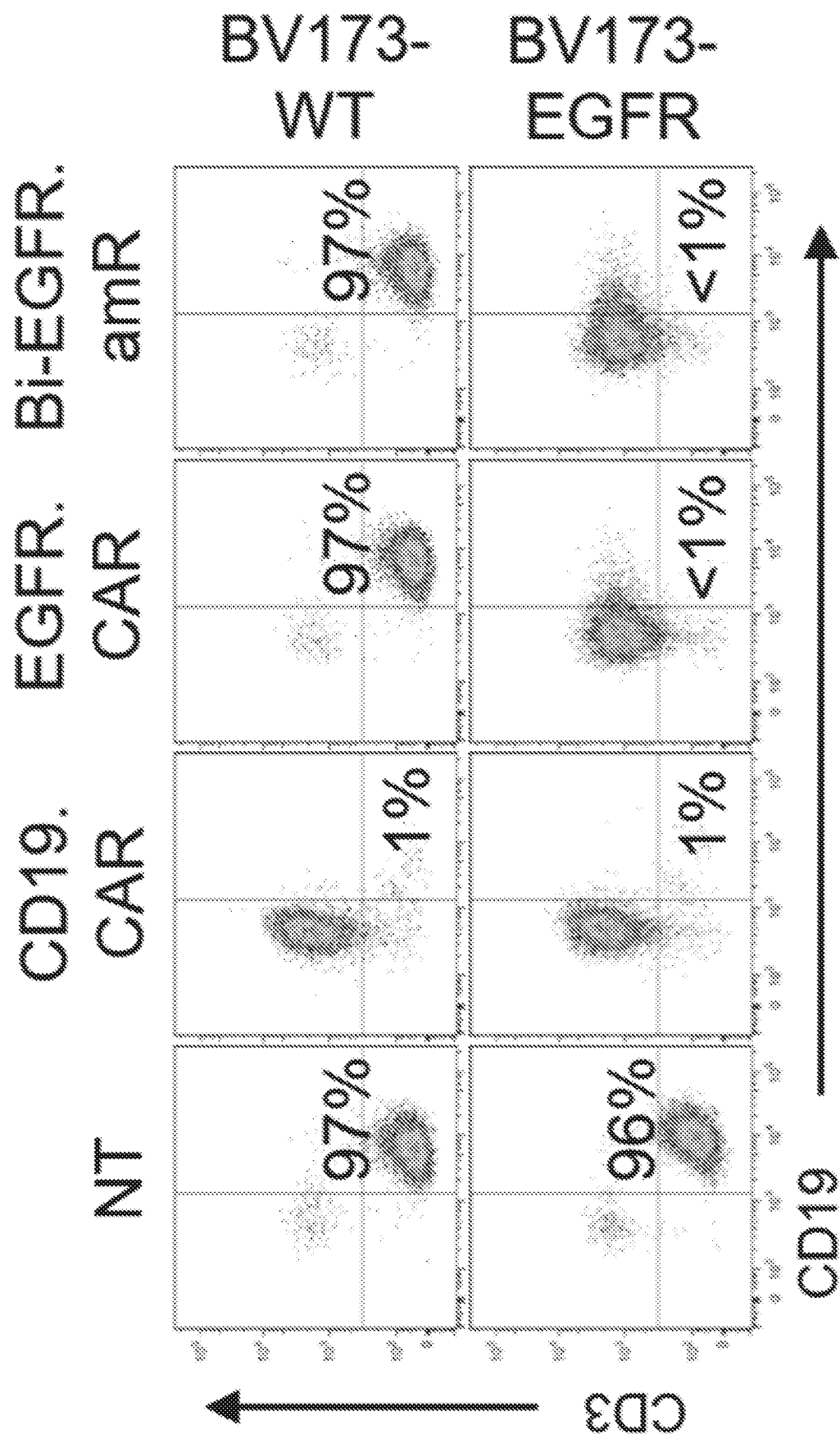
Figure 3C:
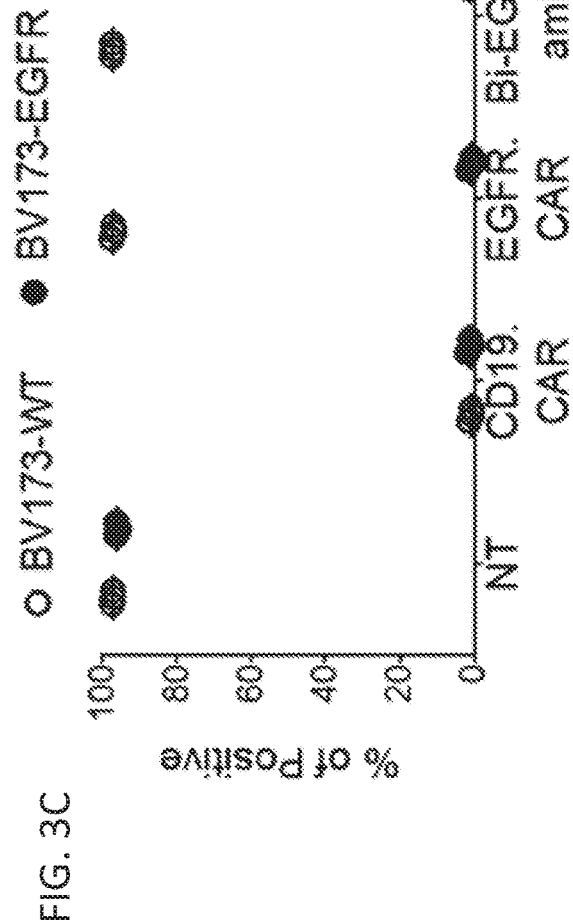
Figure 3D:
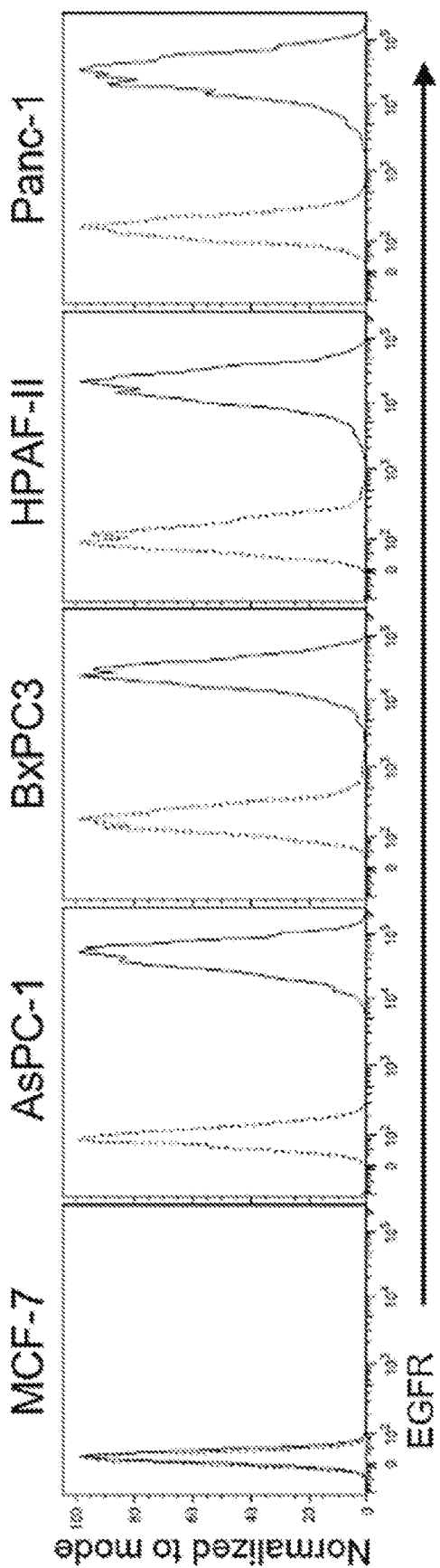
Figure 4A:
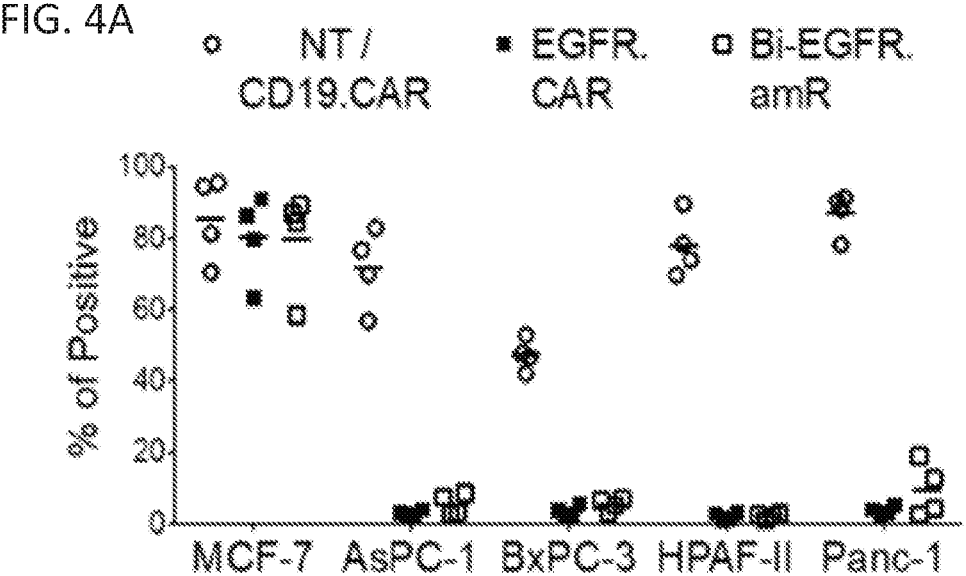
Figure 4B:
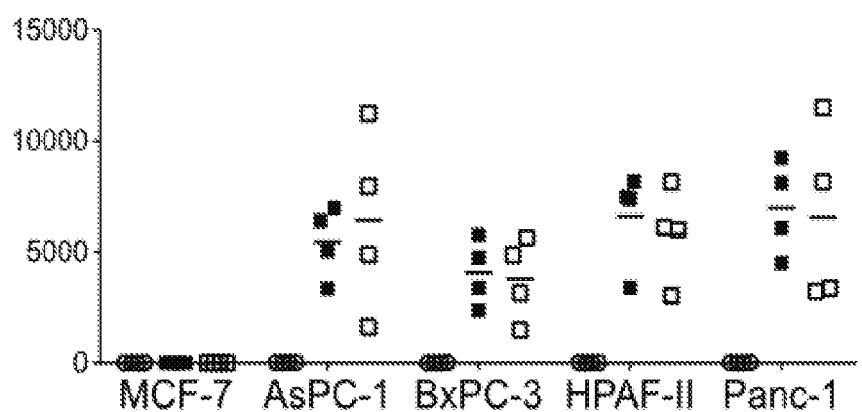
Figure 4C:
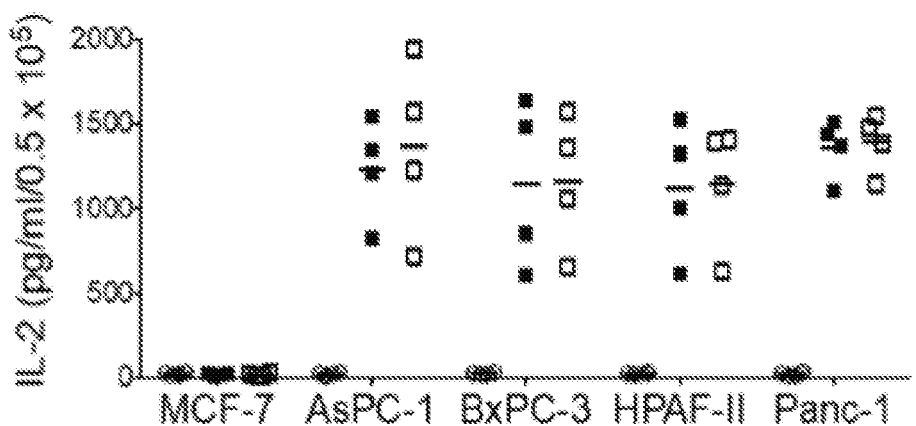
Figure 4E:
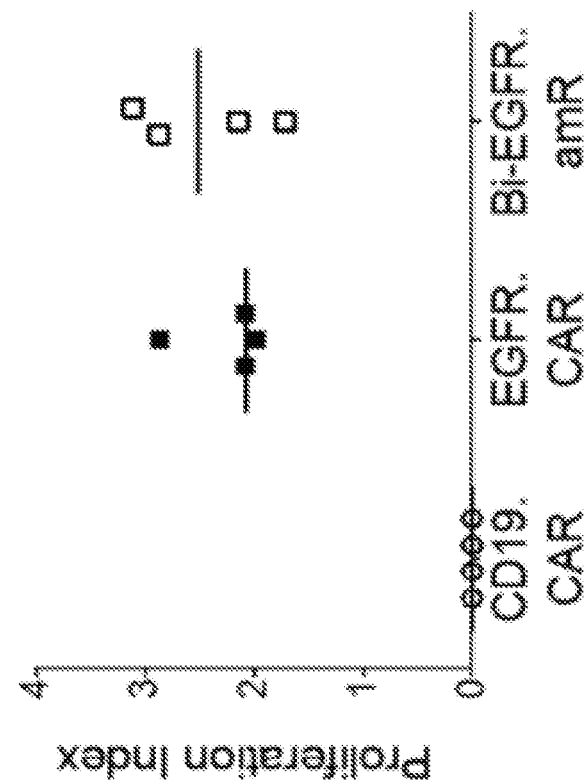
Figure 4D:
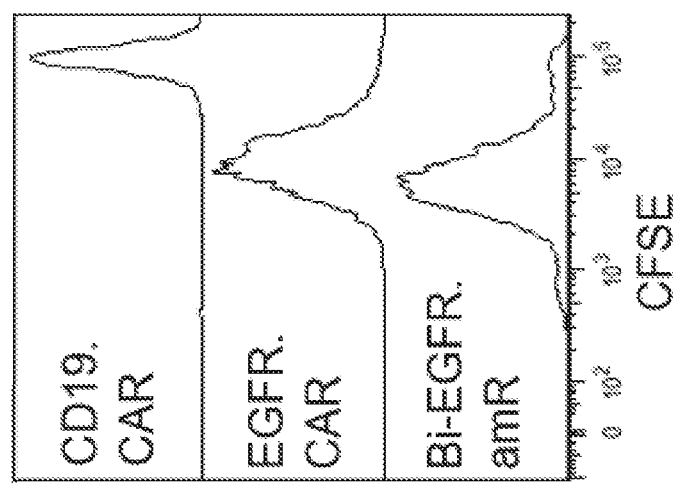
Figure 4H:
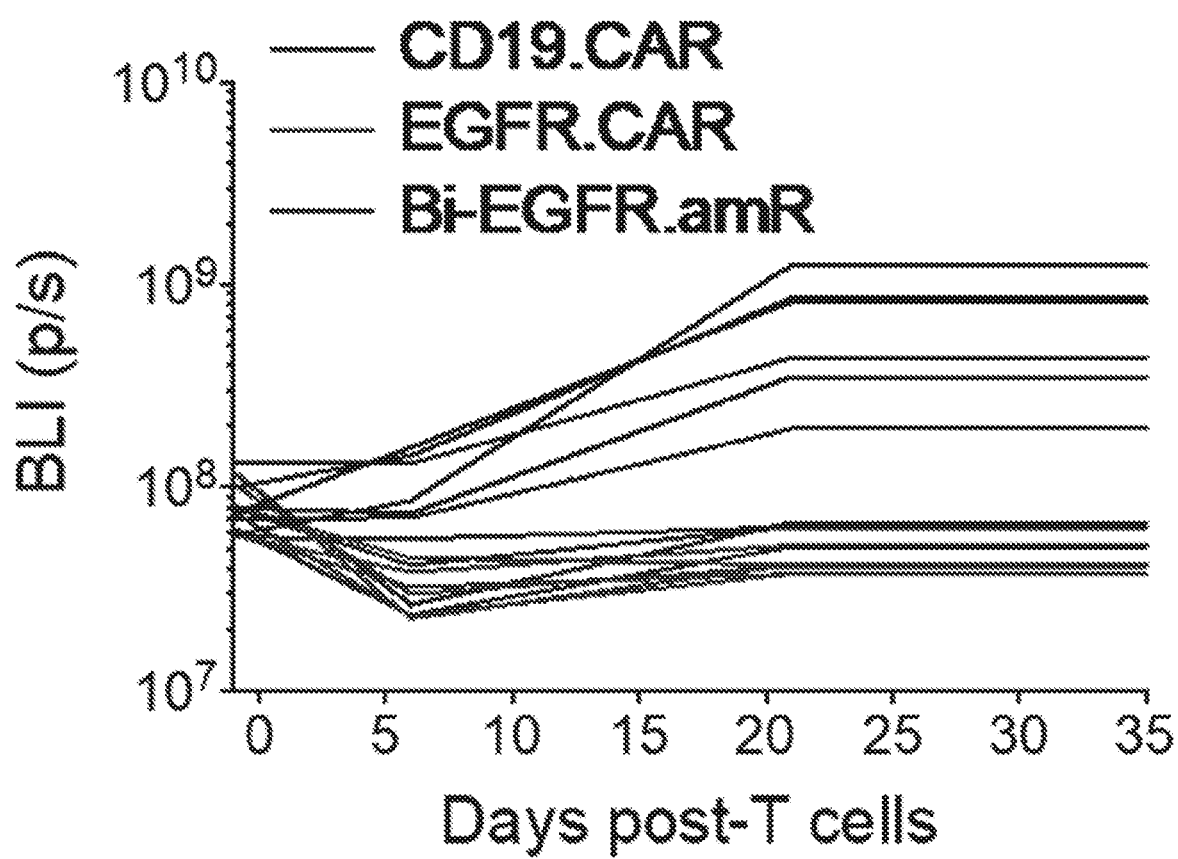

T cells expressing the Bi-EGFR.amR demonstrate activity against EGFR+ tumor cells in vitro and in vivo. To demonstrate that Bi-EGFR.amR-Ts specifically target EGFR, the EGFR-tumor cell line BV173 (BV173-WT) wslas transduced to express EGFR (BV173-EGFR) with a retroviral vector encoding the full-length human EGFR (FIG. 3A). BV173-WT or BV173-EGFR cells were then co-cultured with control non-transduced T cells (NTs), CD19.CAR-Ts, EGFR.CAR-Ts and Bi-EGFR.amR-Ts. NTs did not eliminate neither BV173-WT nor BV173 EGFR cells, CD19.CAR-Ts eliminated both cell types (FIG. 3B,C), whereas Bi-EGFR.amR-Ts and EGFR.CAR-Ts only eliminated BV173-EGFR cells (FIG. 3B,C), indicating the antigen specificity of the redirected T cells. Anti-tumor activity was then tested against tumor cell lines that physiologically express EGFR (FIG. 3D). In co-culture experiments, Bi-EGFR.amR-Ts and EGFR.CAR-Ts demonstrated similar anti-tumor activity in vitro (FIG. 4A) and released comparable amounts of IFNγ (FIG. 4B) and IL-2 (FIG. 4C). Using a CFSE dilution assay, the proliferation of Bi-EGFR.amR-Ts in response to EGFR-expressing targets was demonstrated (FIG. 4D,E). Finally, the anti-tumor activity of Bi-EGFR.amR-Ts was evaluated in a metastatic model of EGFR-expressing pancreatic cancer in NSG mice (FIG. 4F). Bi-EGFR.amR-Ts and EGFR.CAR-Ts equally controlled human Panc-1 tumor cell growth as assessed by measurement of tumor bioluminescence intensity (FIG. 4G,H).

Figure 5A:
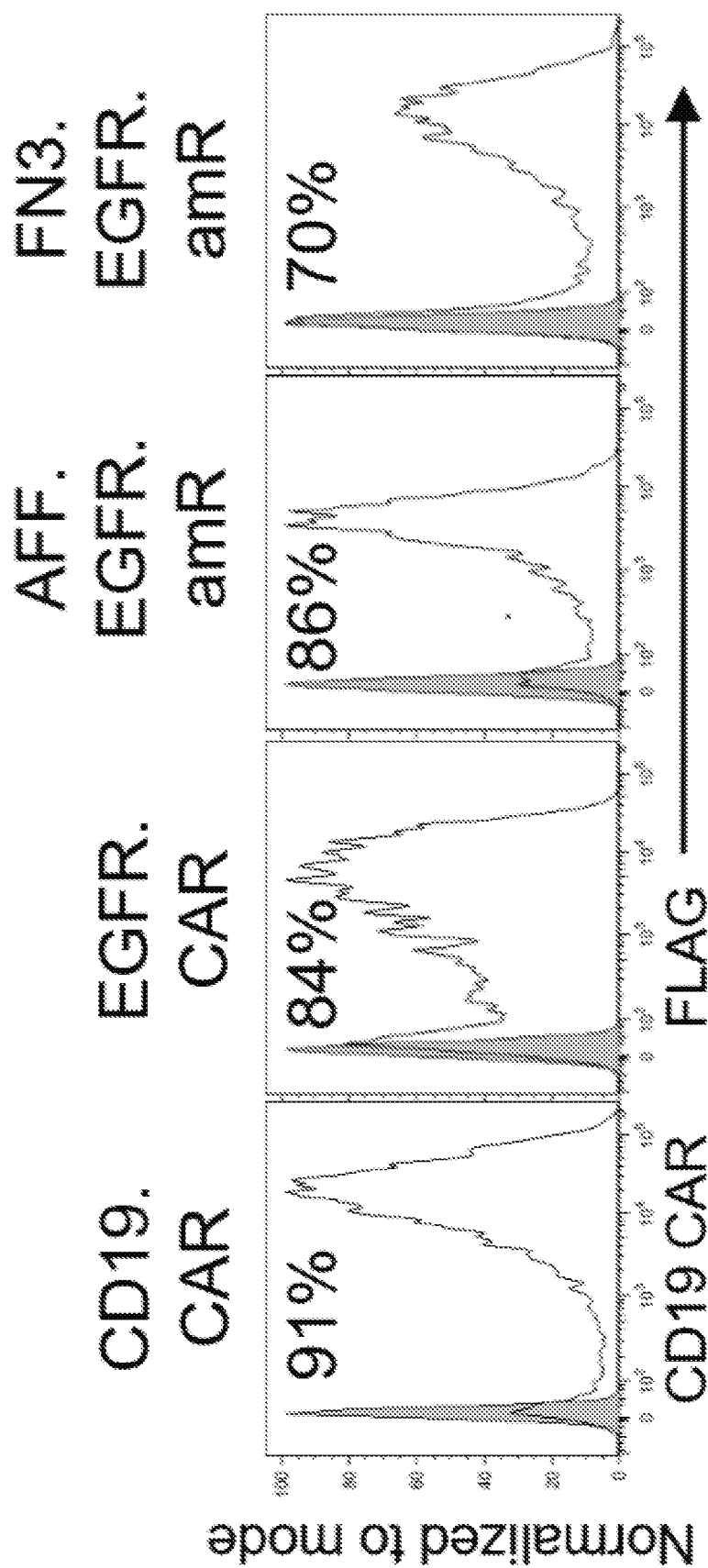
FIGS. 5A-5H show that the AFF.EGFR and FN3.EGFR binding moieties individually have antitumor activity against EGFR+ tumors in vitro when generated into an amR. Activated T cells were transduced with retroviral vectors encoding AFF.EGFR.amR, FN3.EGFR.amR, EGFR.CAR or CD19.CAR.
Figure 5B:
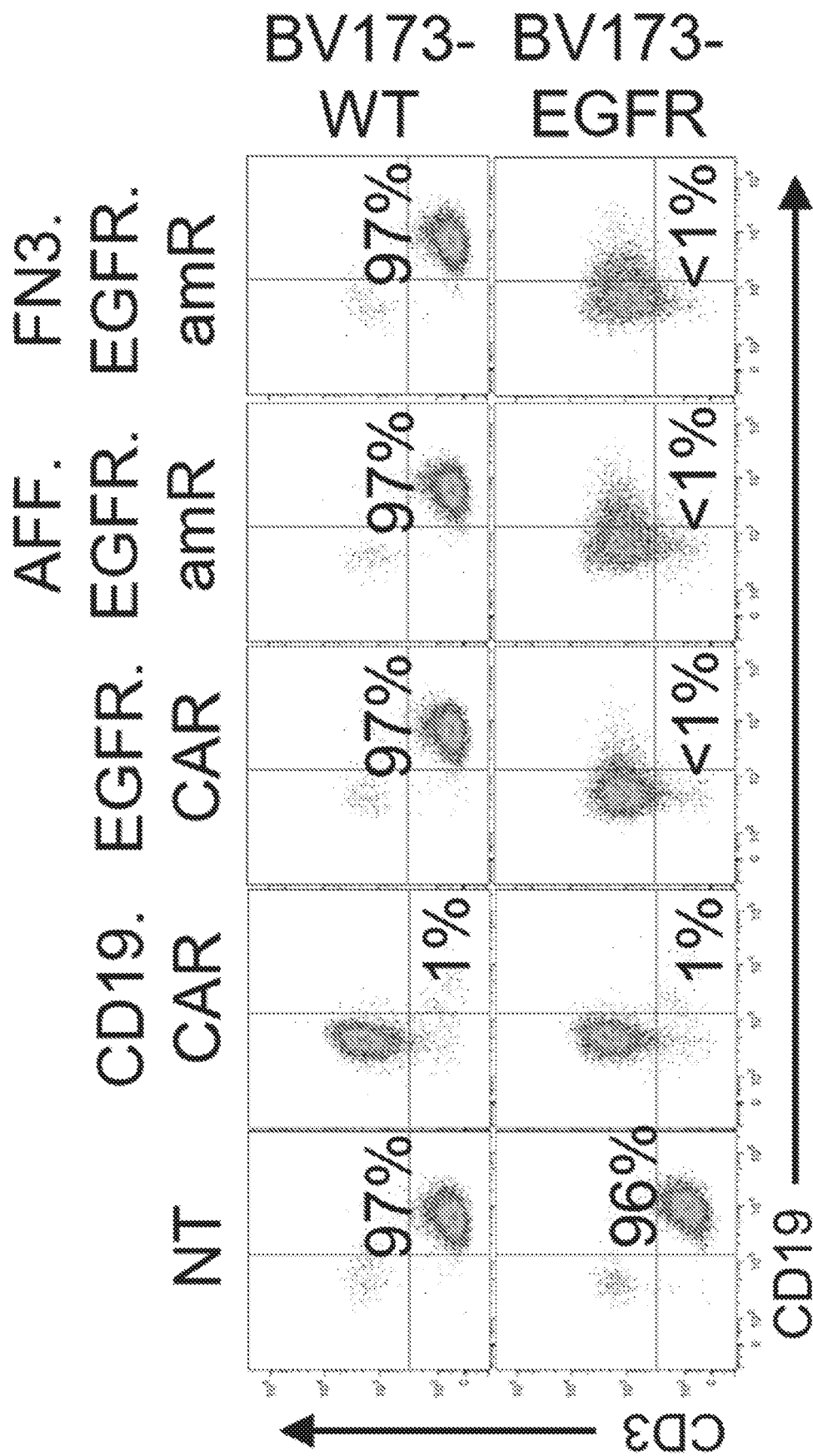
Figure 5C:
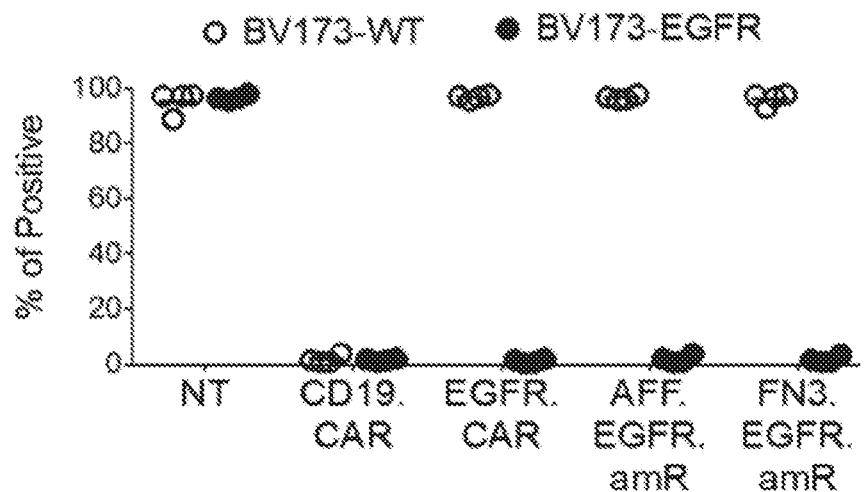
Figure 5D:
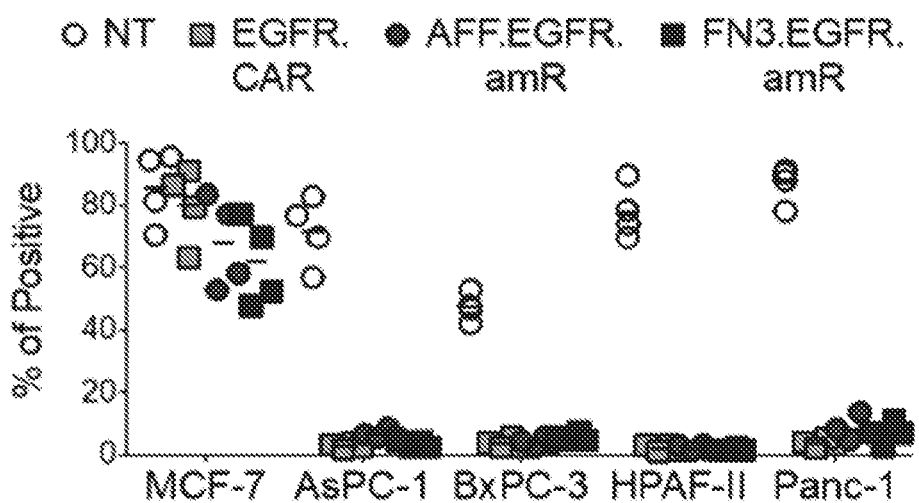
Figure 5E:
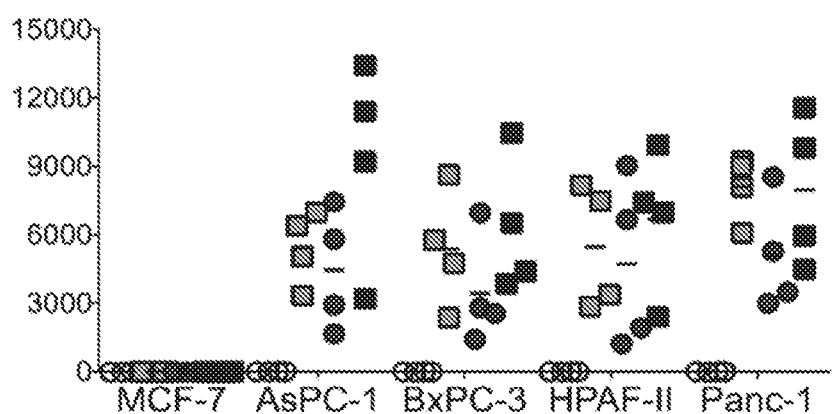
Figure 5F:
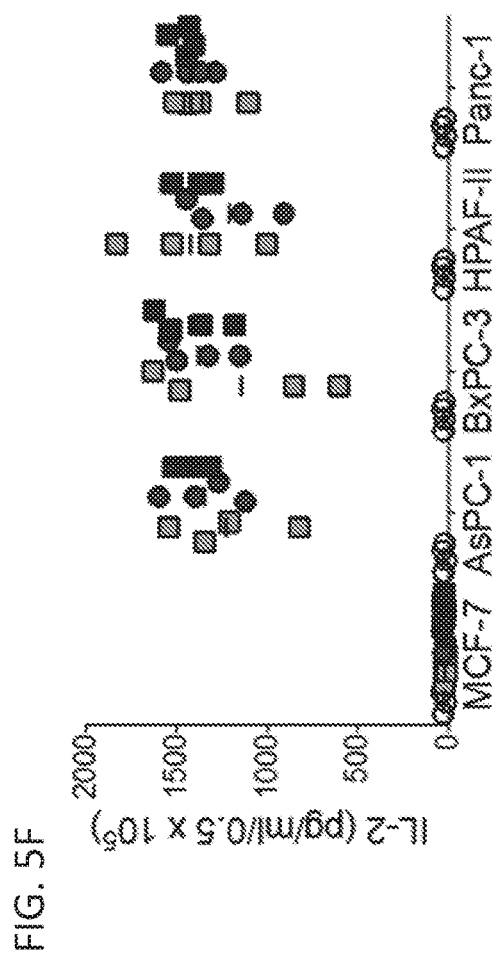
Figure 5H:
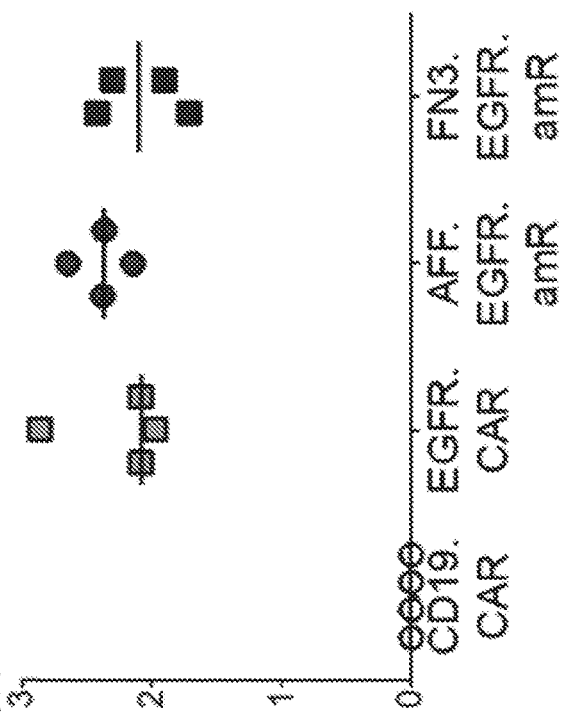
Figure 5G:
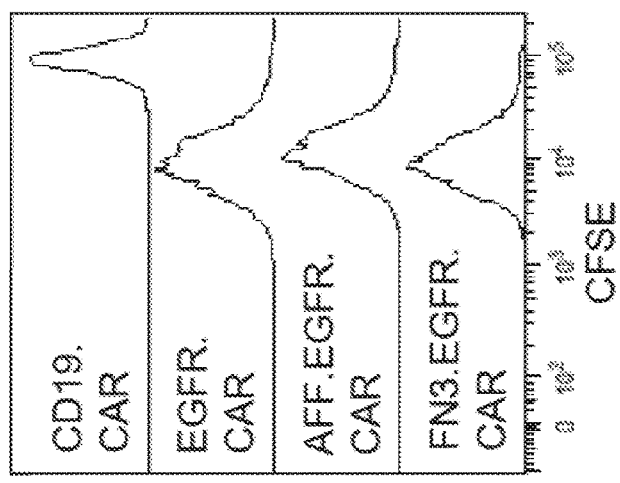
Figure 6A:
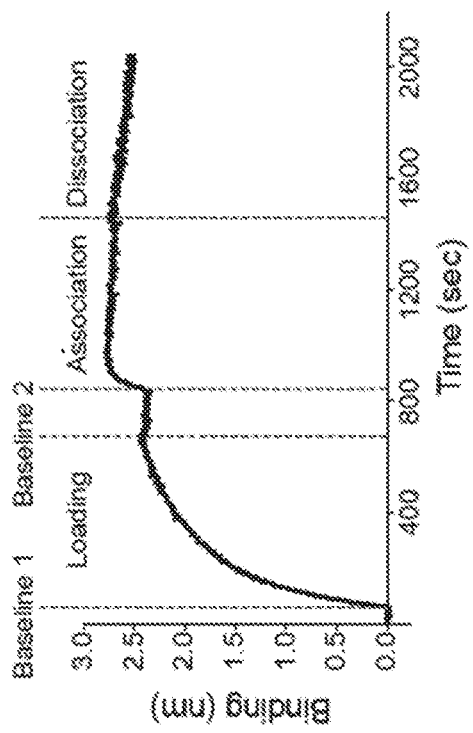
FIGS. 6A-6D shows Alanine substitutionsto-theAFF.EGFR binding moietyabrogatesbindingto EGFR.
Figure 6B:
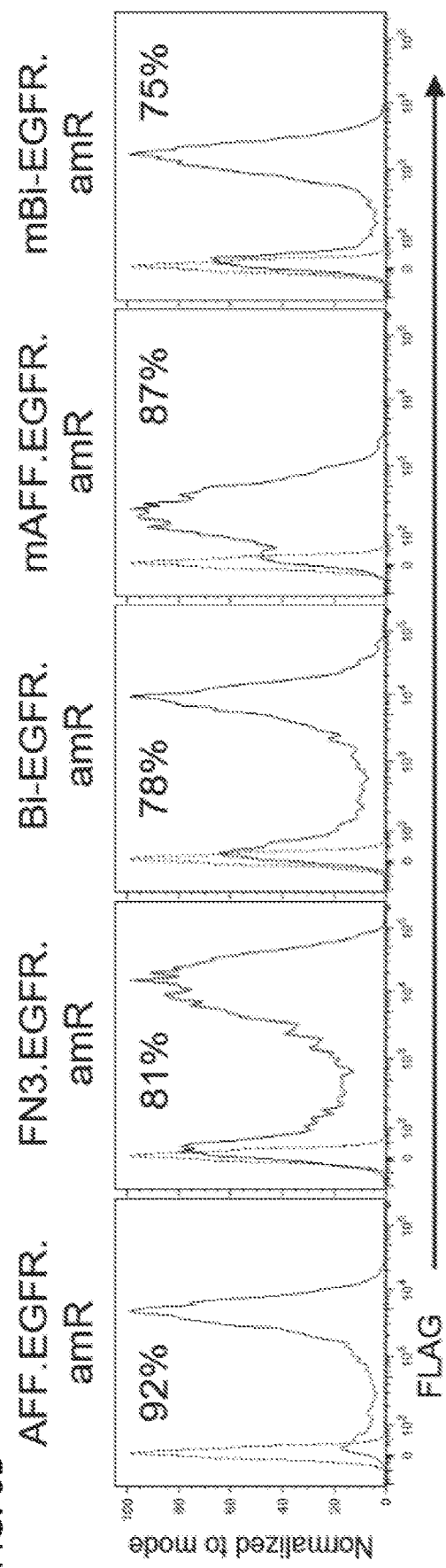
Figure 6C:
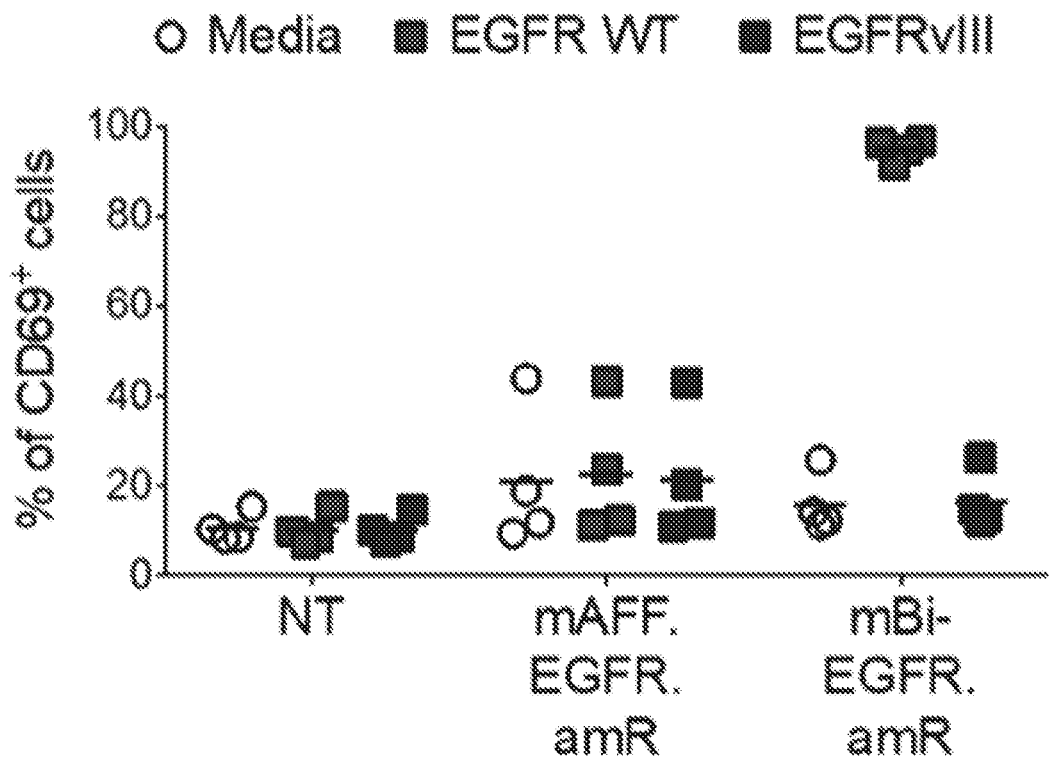
Figure 6D:
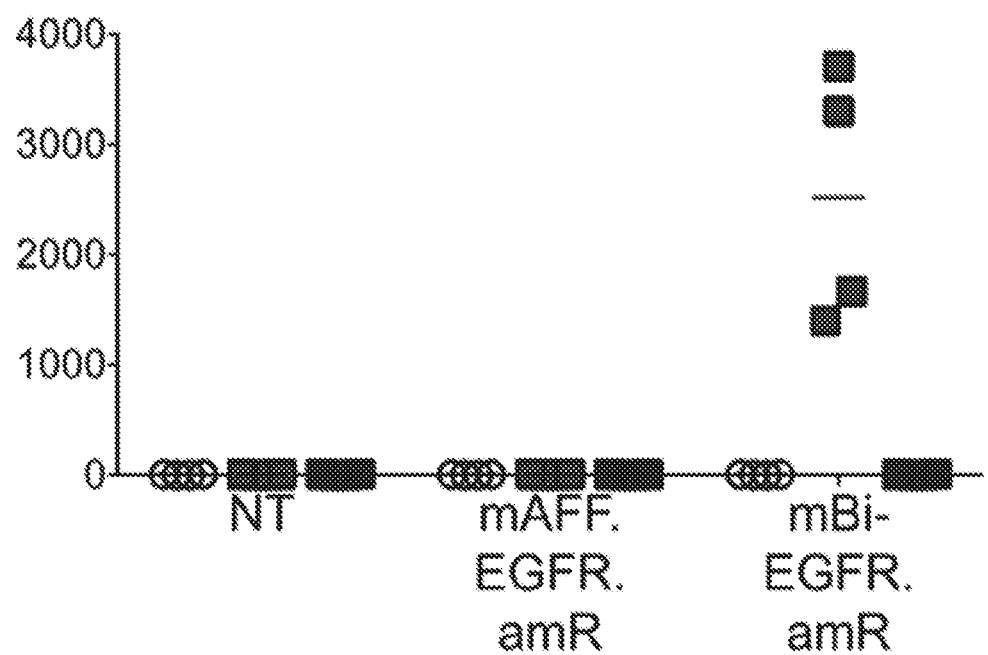
Figure 7A:
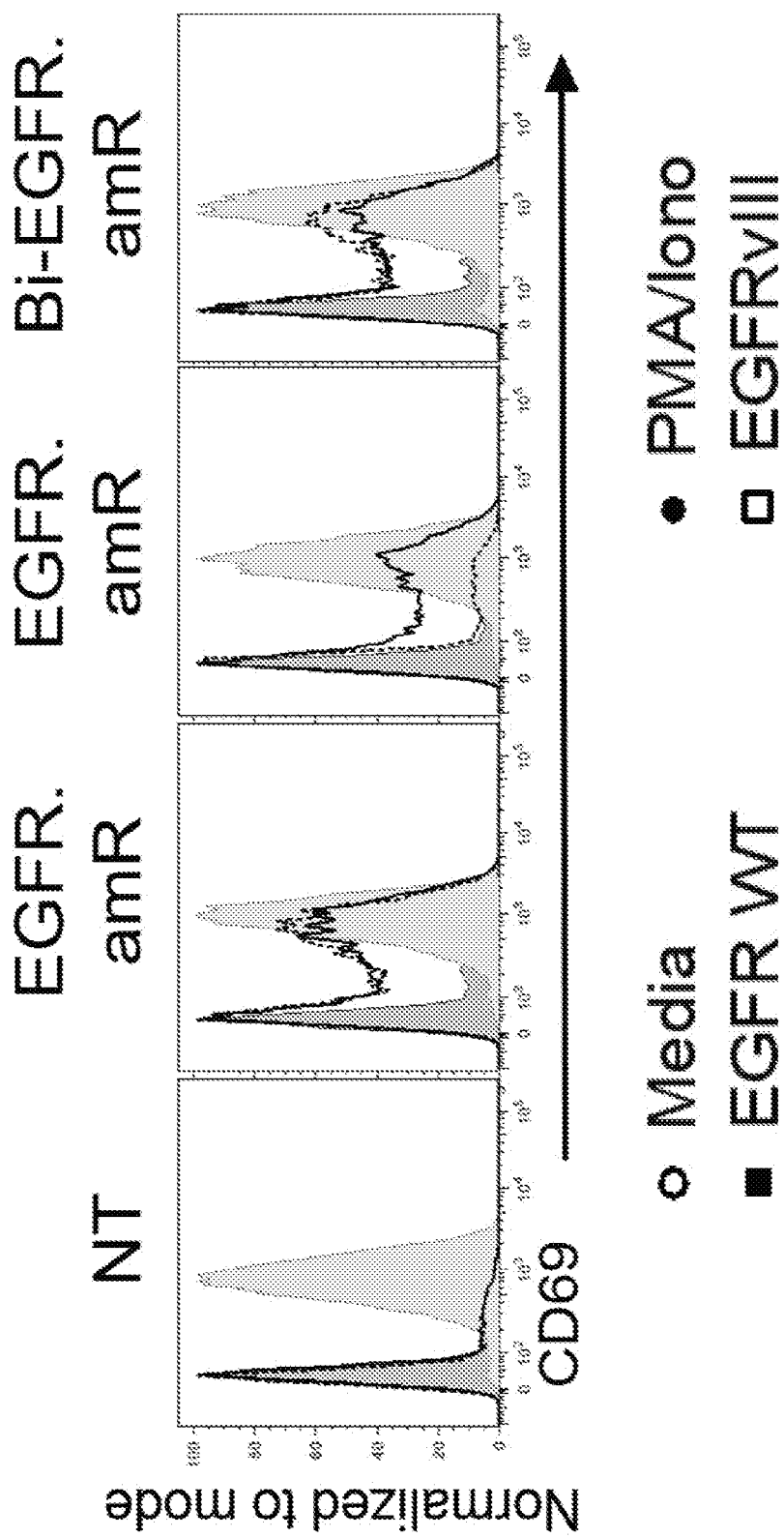
FIGS. 7A-7F show that bi-EGFR.amR-Ts are activated by recognition of two non-overlapping epitopes on EGFR. Control (NTs), AFF.EGFR.amR-Ts, FN3.EGFR.amR-Ts and Bi-EGFR.amR-Ts were seeded in tissue culture plates coated with either recombinant human EGFR WT protein (rEGFR) or the truncated mutant EGFRvIII recombinant protein (rEGFRvIII).
Figure 7B:
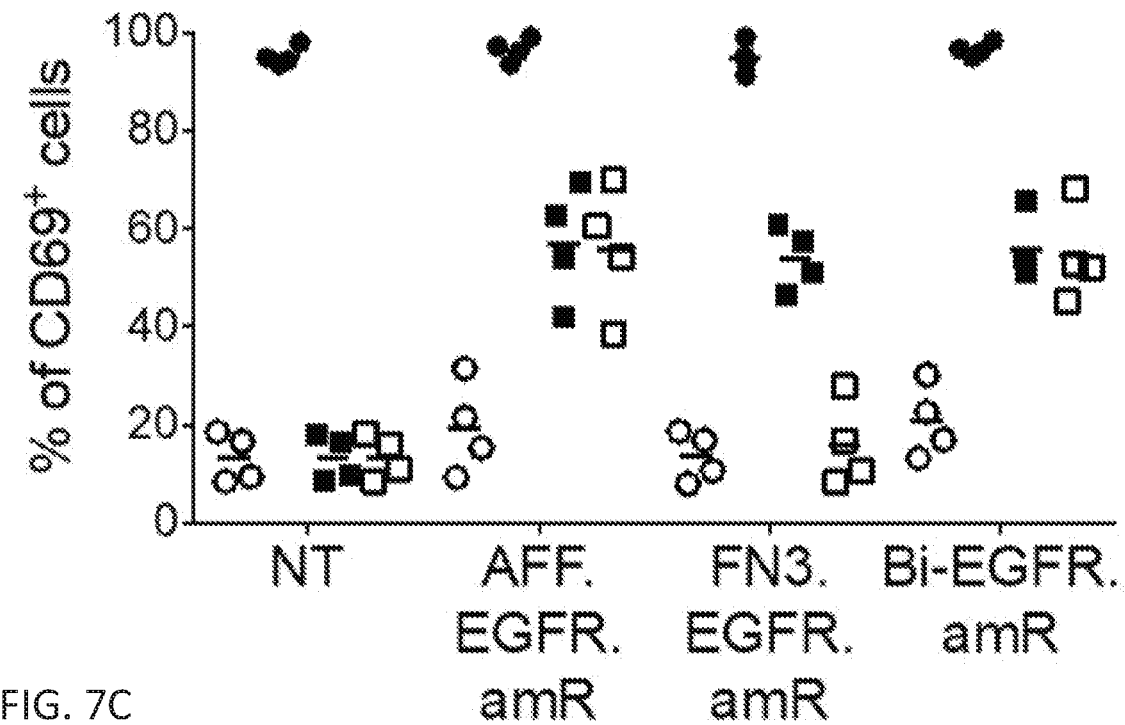
Figure 7C:
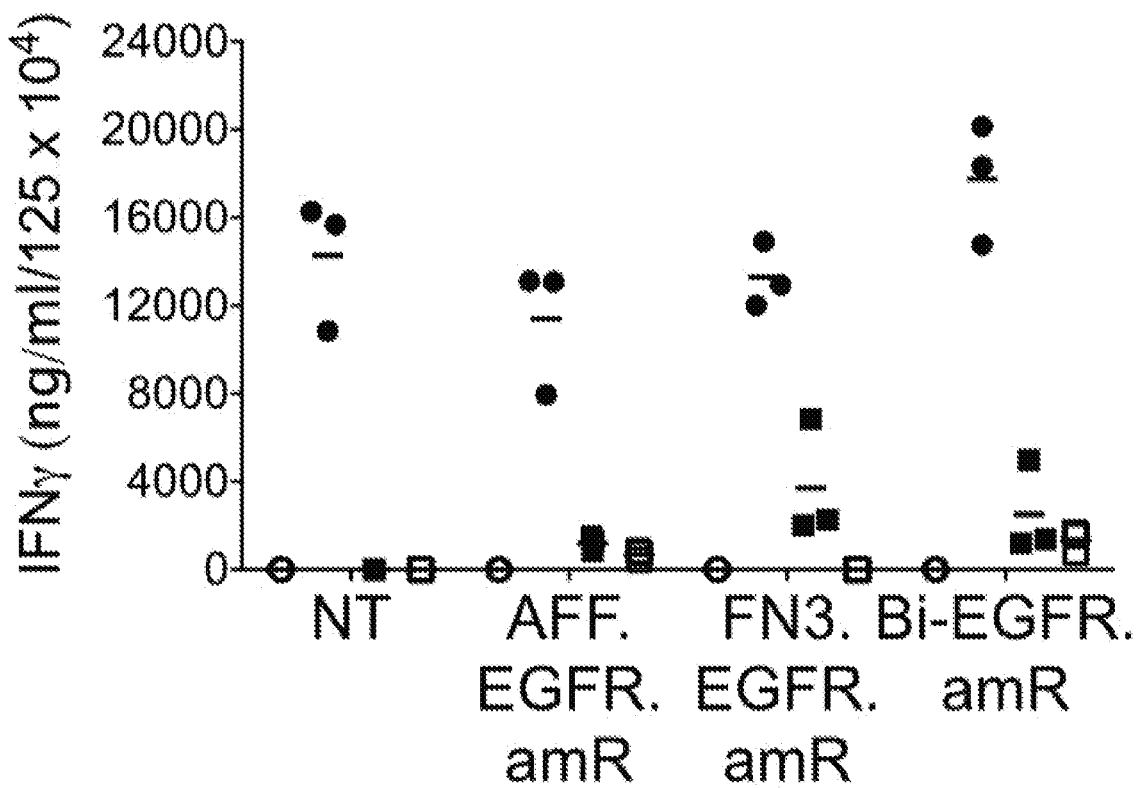
Figure 7D:
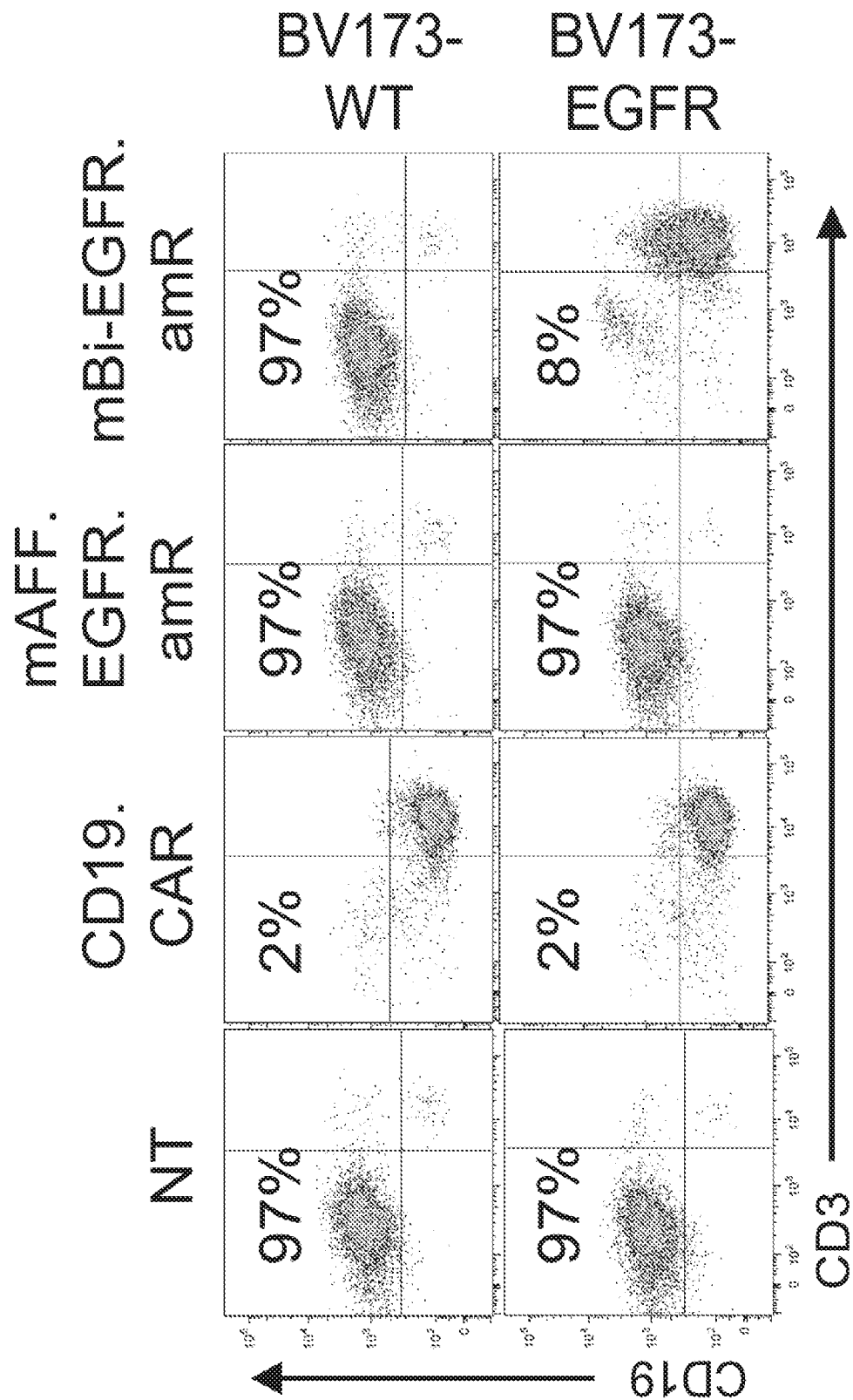
Figure 7E:
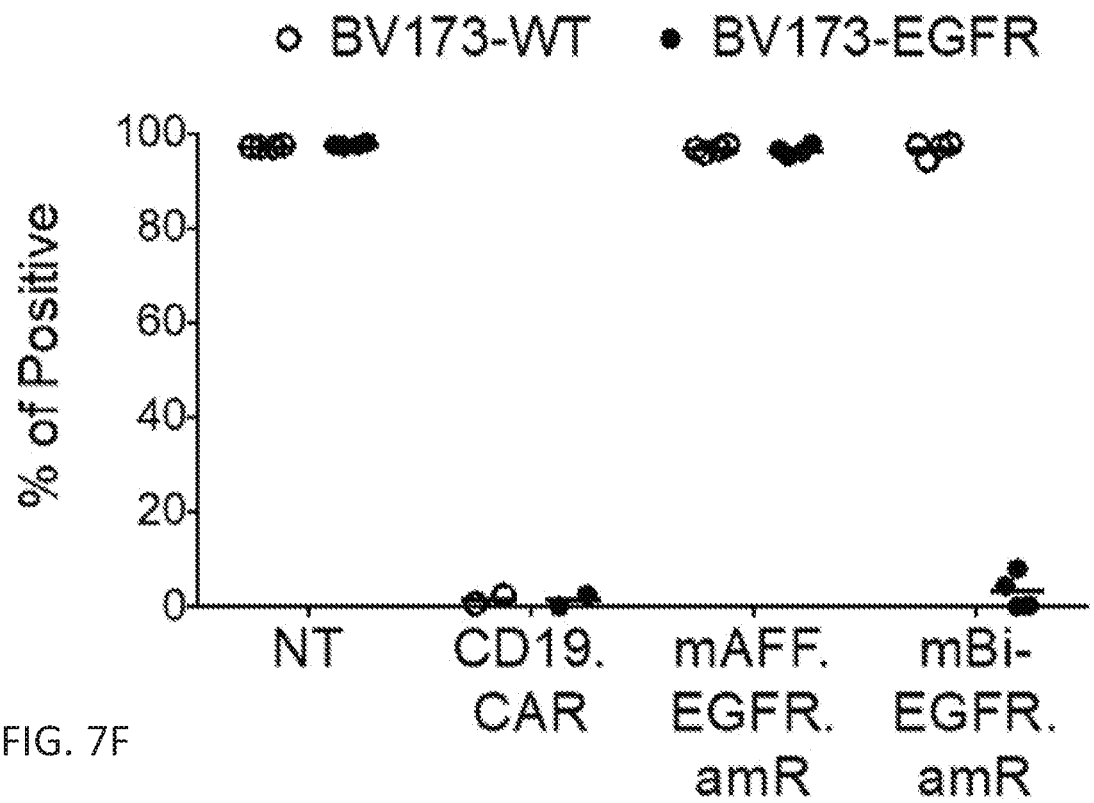
Figure 7F:
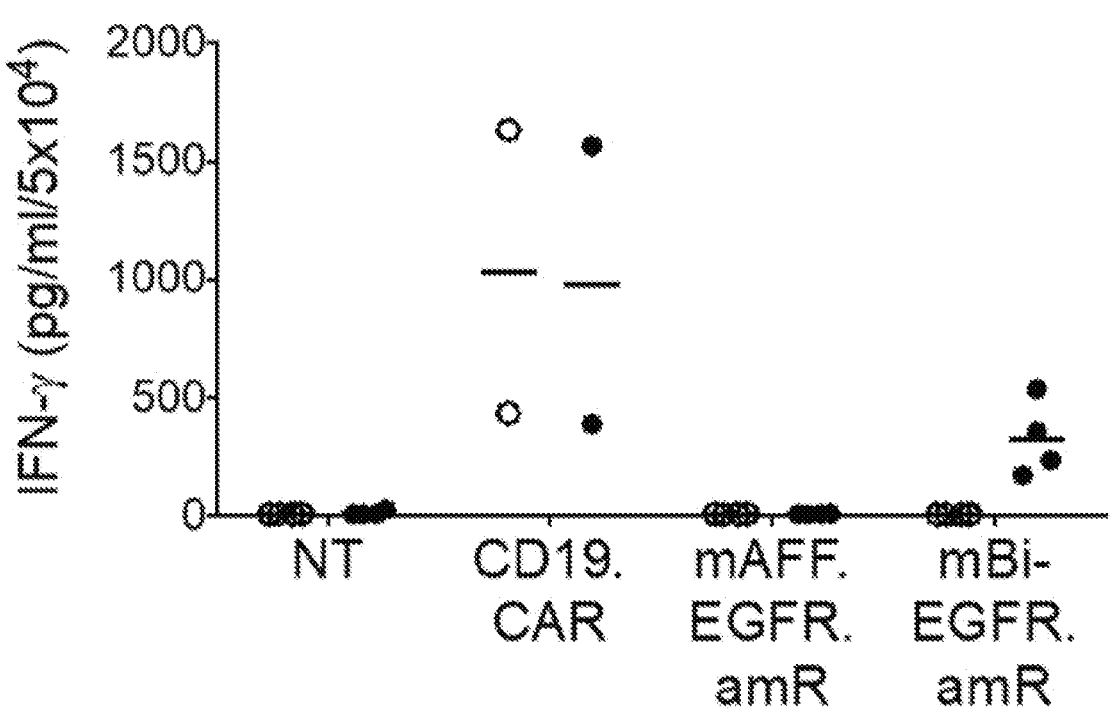

Bi-EGFR.amR-Ts recognize two non-overlapping epitopes of EGFR. AmRs composed of either the FN3.EGFR.amR or the AFF.EGFR.amR alone were transduced in T cells (FIG. 5A). Both AFF.EGFR.amR-Ts and FN3.EGFR.amR-Ts showed comparable activity in vitro against tumor cells expressing the full length EGFR (FIG. 5B-F) and proliferated in response to EGFR expressing targets (FIG. 5G,H). To demonstrate the biepitopic feature of the Bi-EGFR, the binding of Bi-EGFR and each of its monomeric domains was analyzed using the recombinant extracellular domain of the wild-type EGFR (wtEGFR) and the EGFRVIII (EGFRvIII) mutant, a constitutively active and ligand-independent variant of EGFR with deletions in exons 2-7. Bi-EGFR and Z domain-based AFF.EGFR bound both wtEGFR and EGFRvIII. However, FN3 domain-based FN3.EGFR bound to wtEGFR but not EGFRvIII (FIG. 6A), suggesting that it recognizes an antigen encoded in the 267 AA that are absent in EGFRVIII. To assess recognition of two different EGFR epitopes, the extracellular domain of wtEGFR and EGFRvIII mutant recombinant proteins was used. Control, AFF.EGFR.amR-Ts, FN3.EGFR.amR-Ts and Bi-EGFR.amR-Ts were seeded in tissue culture plates coated with either wtEGFR or EGFRVIII, and the CD69 expression and IFN-γ release by T cells were measured. Both wtEGFR and EGFRvIII recombinant proteins activated AFF.EGFR.amR-Ts and BiEGFR.amR-Ts, while only the wtEGFR protein activated FN3.EGFR.amR-Ts (FIG. 3A-C), indicating that the epitope recognized by the FN3.EGFR binding moiety is either located in the 267 AA region deleted in EGFRvIII, or the mutation has altered the epitope accessibility due to the deletion-induced conformational changes. In contrast, the AFF.EGFR binding moiety recognizes an epitope that is conserved between EGFR and EGFRVIII (FIG. 7A-C). To ensure that both AFF.EGFR and FN3.EGFR binding moieties can induce the activation of T cells when assembled into the Bi-EGFR.amR, an AFF.EGFR.amR mutant-binding moiety was generated (mAFF.EGFR.amR) in which critical residues at the EGFR-binding alpha helices were mutated to alanine to reduce binding to EGFR. As shown in FIG. 6B, mAFF.EGFR.amR was expressed in T cells, but mAFF.EGFR.amR-Ts did not eliminate BV173-EGFR cells (FIG. 6C,D), indicating that the mutations had abrogated binding to EGFR. However, T cells expressing a Bi-EGFR.amR constructed with the FN3.EGFR and mAFF.EGFR binding moieties (mBi-EGFR.amR) upregulated CD69 and released IFN-γ when seeded in wells coated with wtEGFR recombinant protein, but not in response to EGFRvIII protein, indicating that the FN3.EGFR binding moiety alone can induce T cell activation when the function of the other EGFR-binding moiety (AFF.EGFR) is abolished in the mBi-EGFR.amR (FIG. 7D-F).

Figures 8A, 8B, 8C:
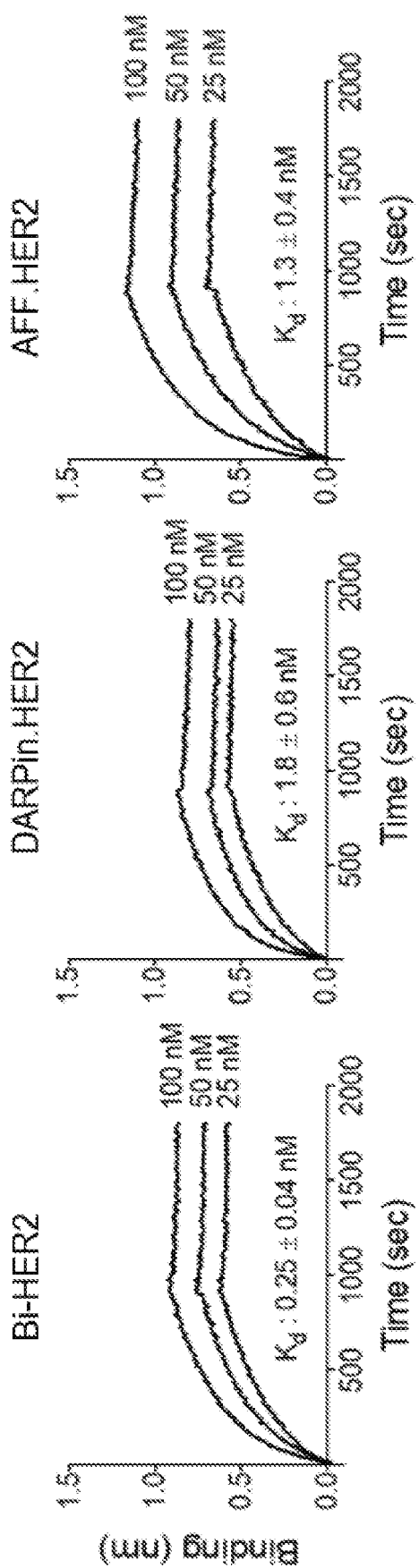
FIGS. 8A-8I show that bi-HER2.amR-Ts have anti-tumor activity against HER2-expressing primary cells in vitro and in vivo.

Biepitopic amR against HER2 demonstrates anti-tumor activity in vitro and in vivo. An amR receptor was constructed against another member of the ErbB family of receptor tyrosine kinase, HER2, to demonstrate the applicability of this technology to other TAAs. Using a similar approach to the construction of Bi-EGFR, a tumor antigen binding moiety that targets two different epitopes of HER2 (Bi-HER2) was generated, which showed a HER2-binding affinity (Kd) around 0.25+0.04 nM (FIG. 8A), compared to 1.8+0.6 nM (FIG. 8B) of a HER2 binding DARPin and 1.3+0.4 nM of a HER2-binding Z domain (FIG. 8C), respectively.

Figure 8D:
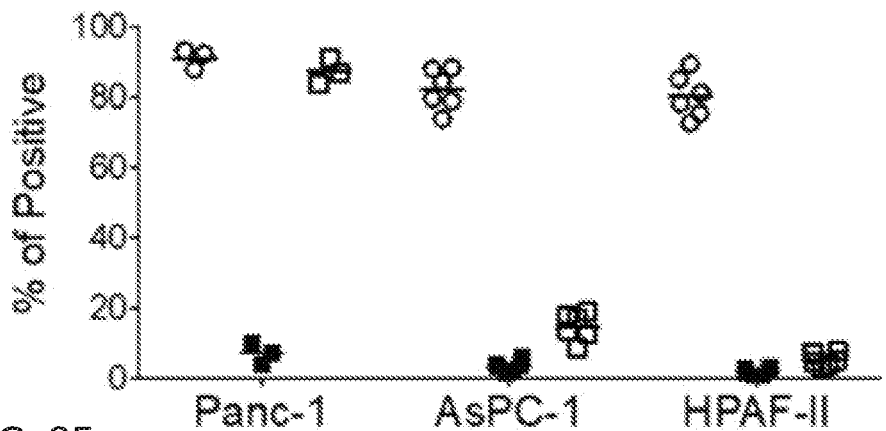
Figure 8E:
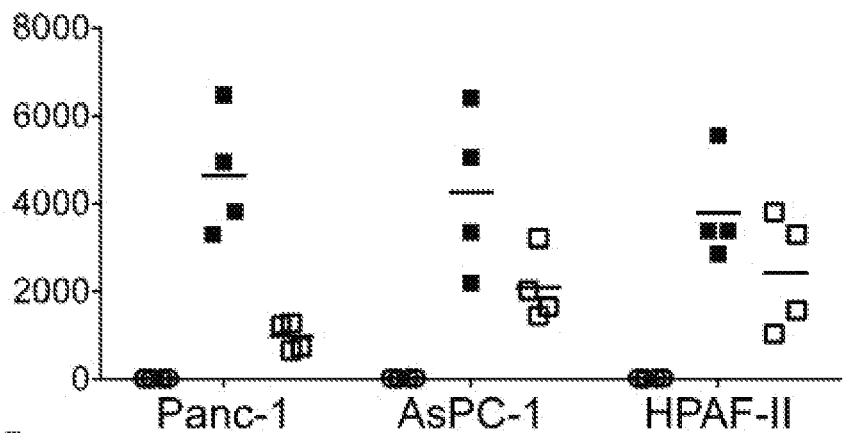
Figure 8F:
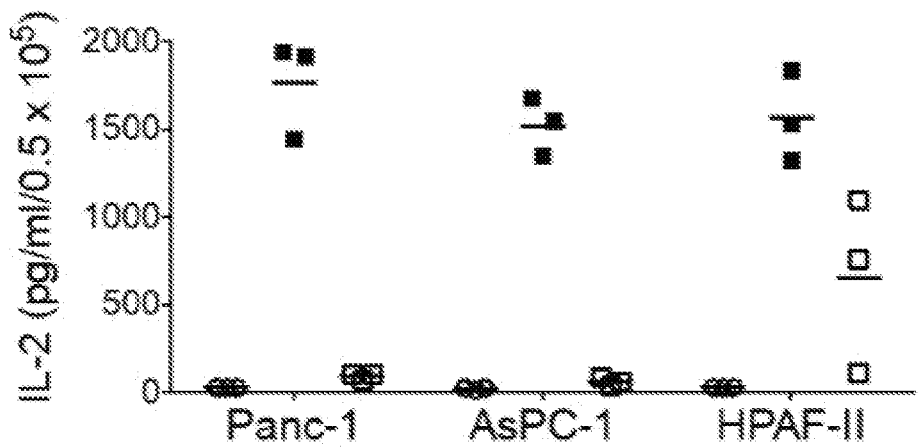
Figure 8G:
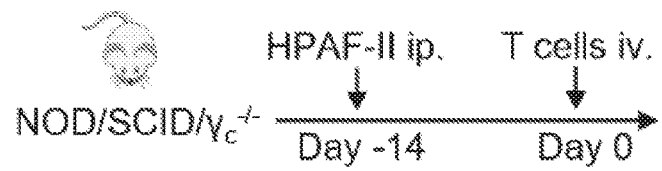
Figure 8H:
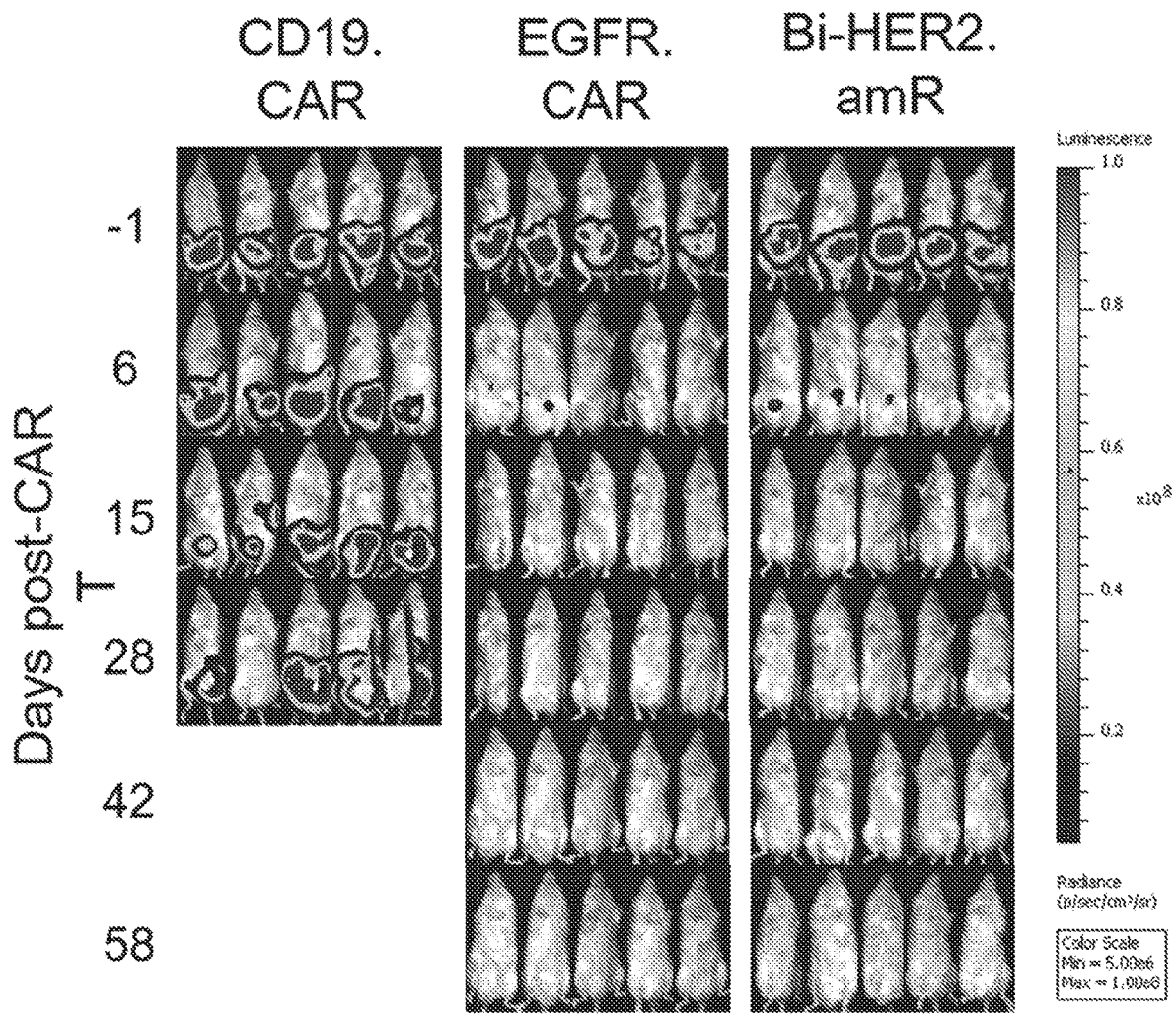
Figure 8I:
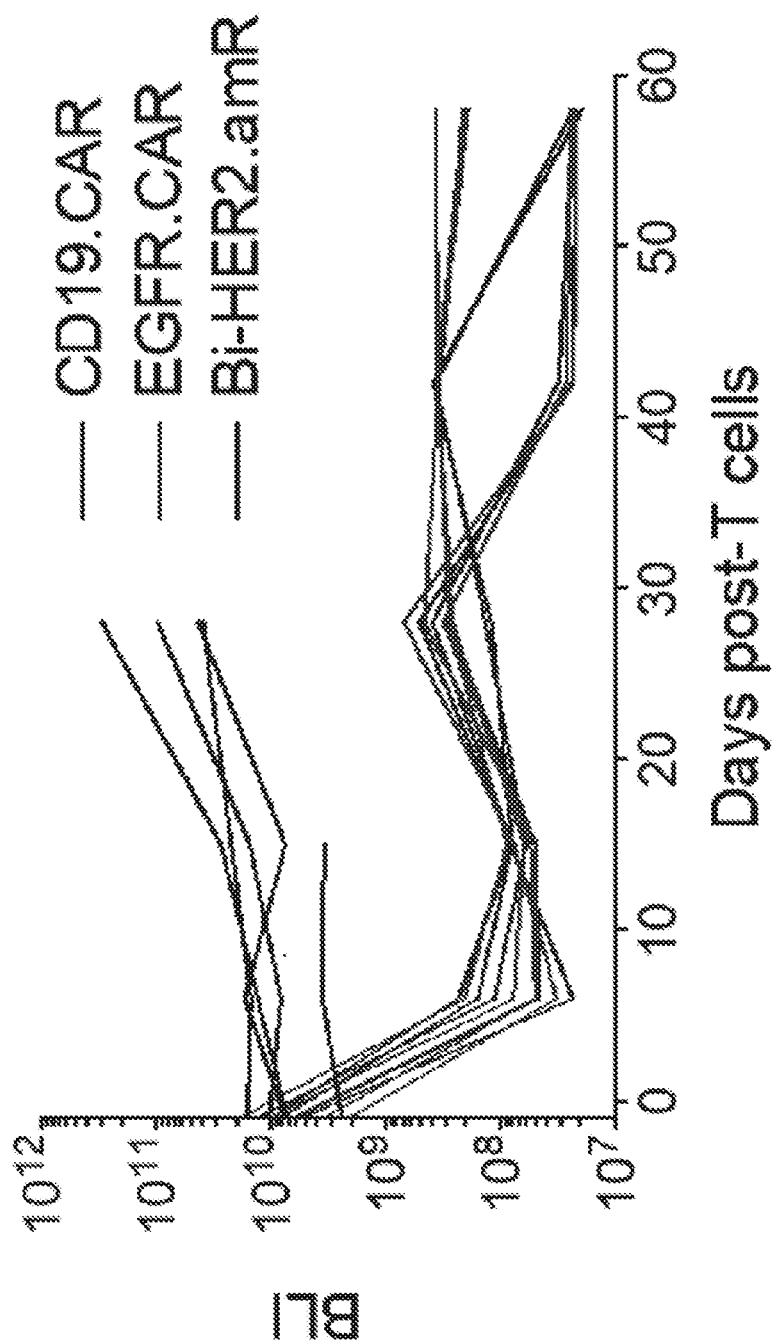
Figure 9A:
FIG. 9A-E show that expression of the Bi-HER2.amR redirects the specificity of T cells.
Figure 9B:
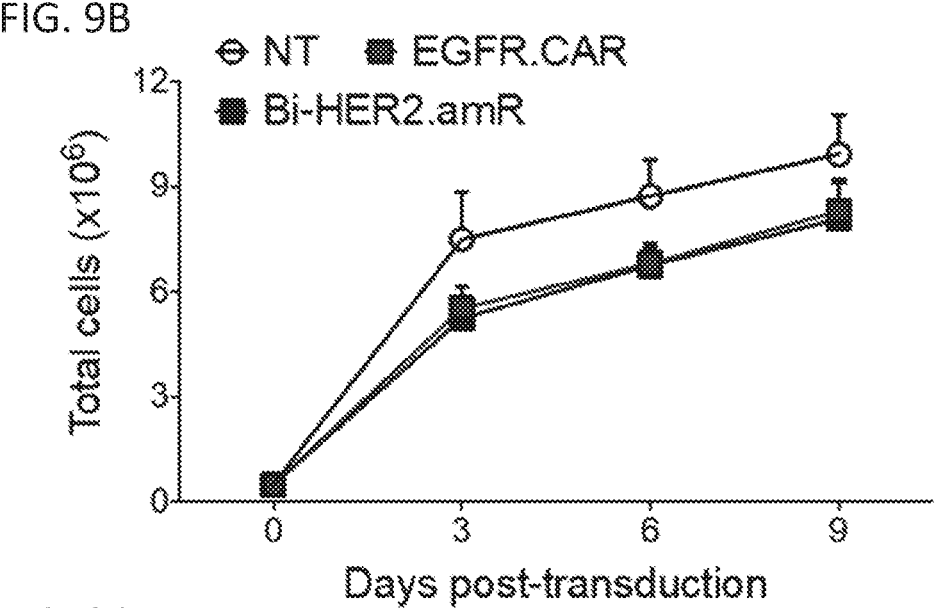
Figure 9C:
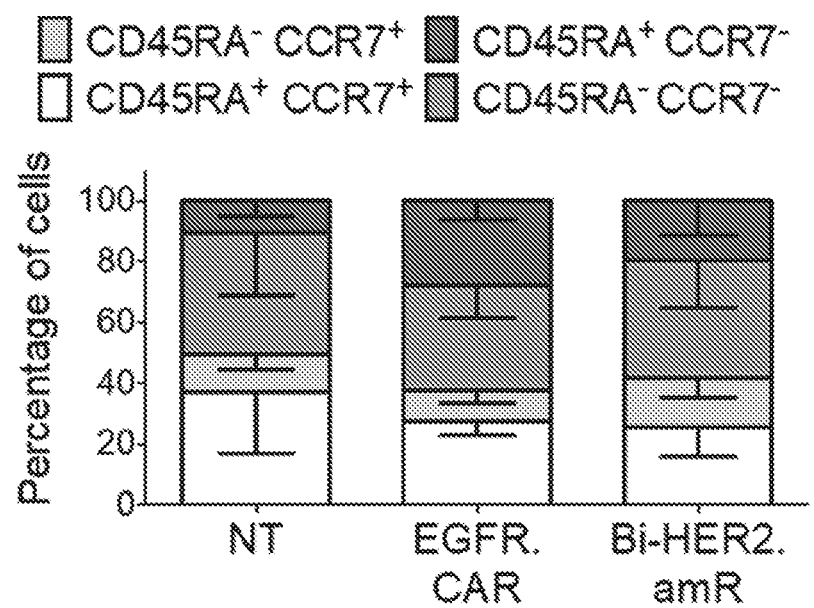
Figure 9D:
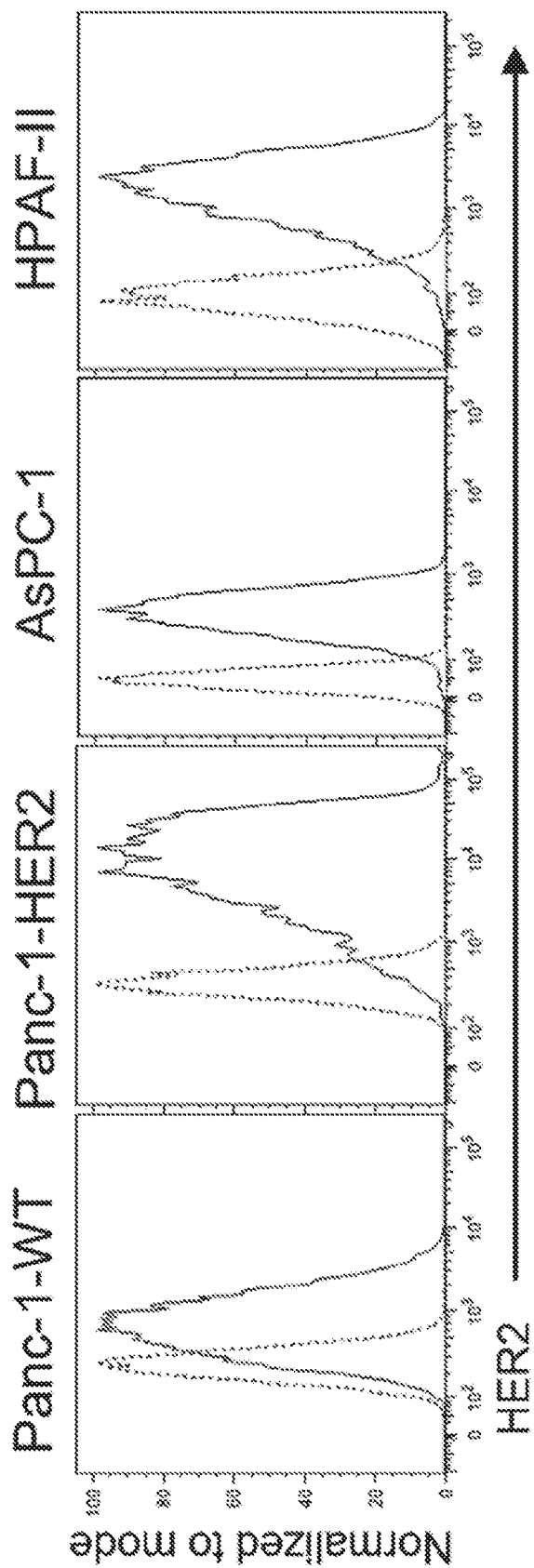
Figure 9E:
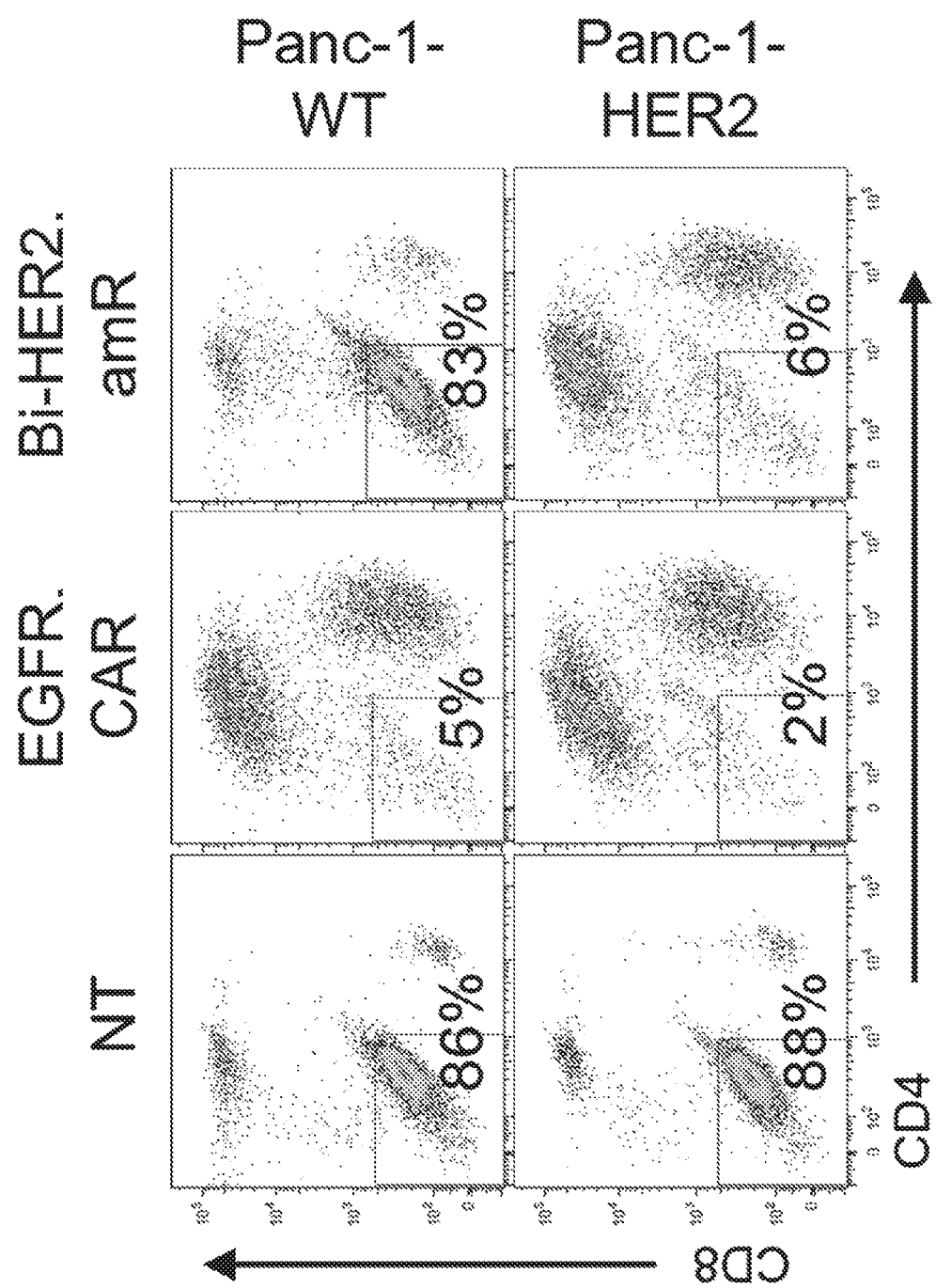
Figure 9F:
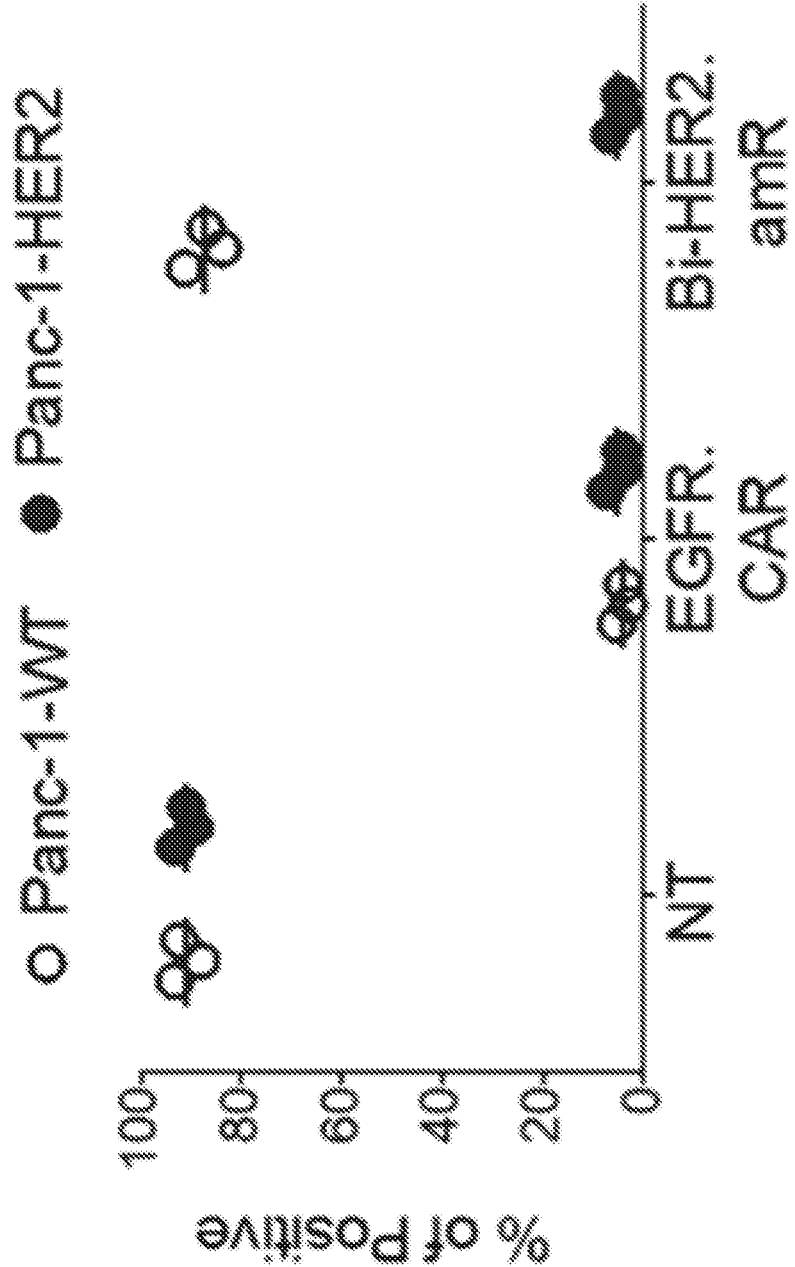
(FIG. 9F) Quantification of remaining Panc-1 cells after 5 days of co-culture (n=3), p<0.01 when the frequency of Panc-1-WTorPanc-1-HER2cells is compared in Bi-HER2.amR-Ts.

Based on this novel HER2-binding ligand, a biepitopic Bi-HER2.amR was constructed (FIG. 9A). T cells stably expressed the Bi-HER2.amR (Bi-HER2.amR-Ts) upon retroviral transfer, expanded in vitro in response to exogenous cytokines (FIG. 9B) and maintained T cell composition comparable to control T cells (FIG. 9C). Bi-HER2.amR-Ts demonstrated specific targeting of HER2-expressing cells (FIG. 9D-F). Furthermore, Bi-HER2.amR-Ts exhibited anti-tumor activity (FIG. 8D) and released IFN Y (FIG. 8E) and IL-2 (FIG. 8F) in a HER2-dependent manner when co-cultured with tumor cell lines expressing HER2, but not with HER2-negative cells lines (FIG. 9D). We also evaluated the efficacy of Bi-HER2.amR-Ts in a metastatic tumor model of HER2-expressing human HPAF-II pancreatic cancer in NSG mice (FIG. 8G). Bi-HER2.amR-Ts and EGFR.CAR-Ts equally controlled tumor cell growth as assessed by measurement of tumor bioluminescence intensity (FIG. 8H,I).

Figure 10A:
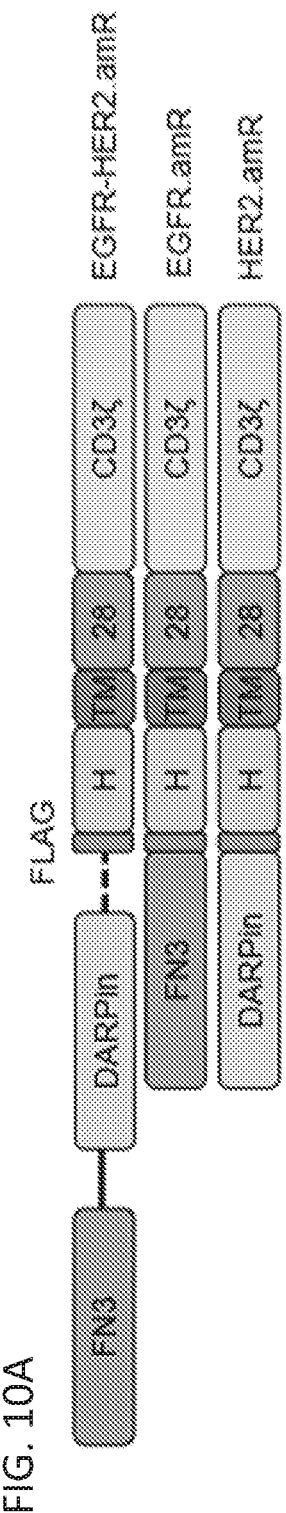
FIG. 10A-H shows characteristics of EGFR-HER2.amR expressing T cells.
Figure 10B:
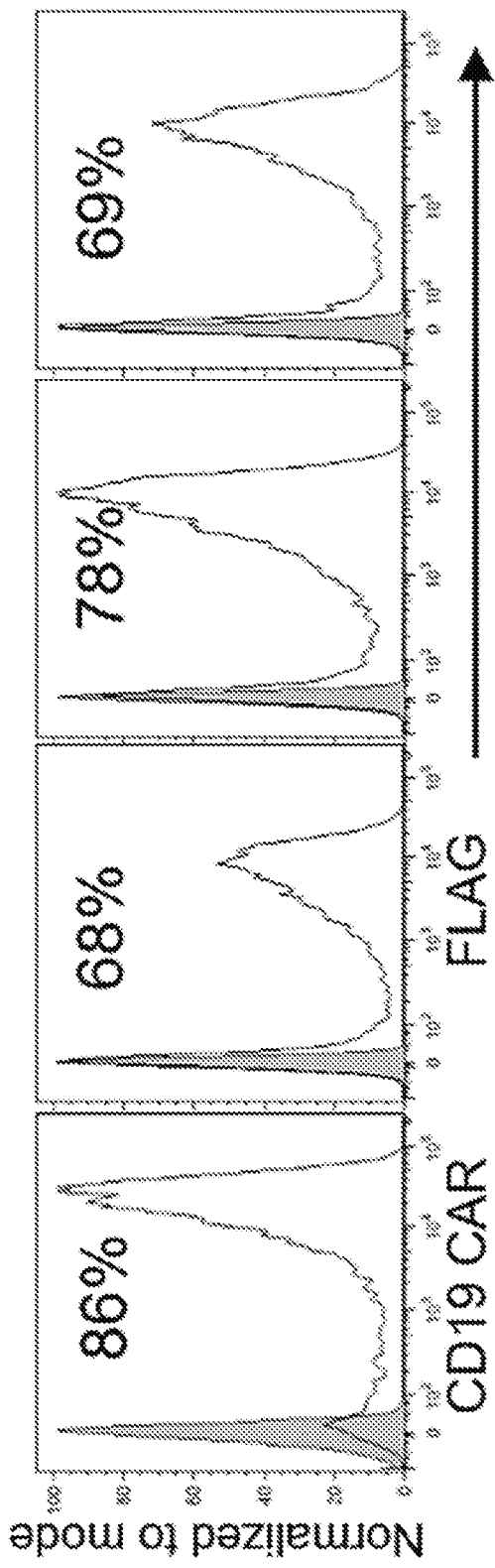
Figure 10C:
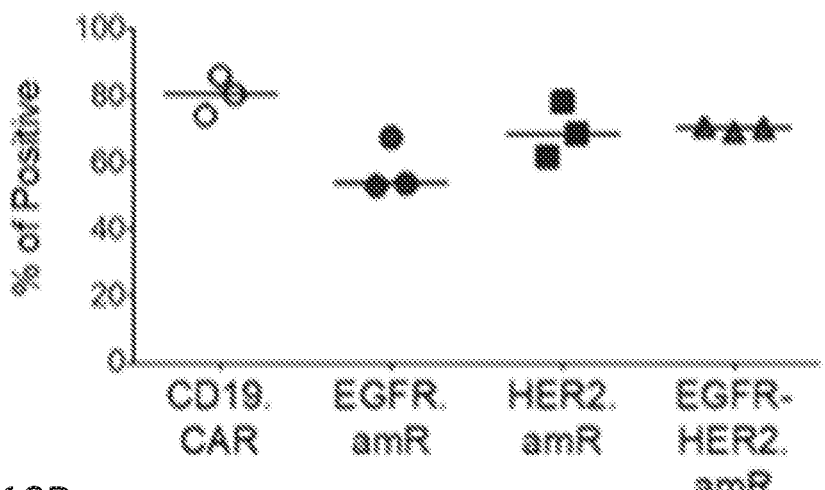
Figure 10D:
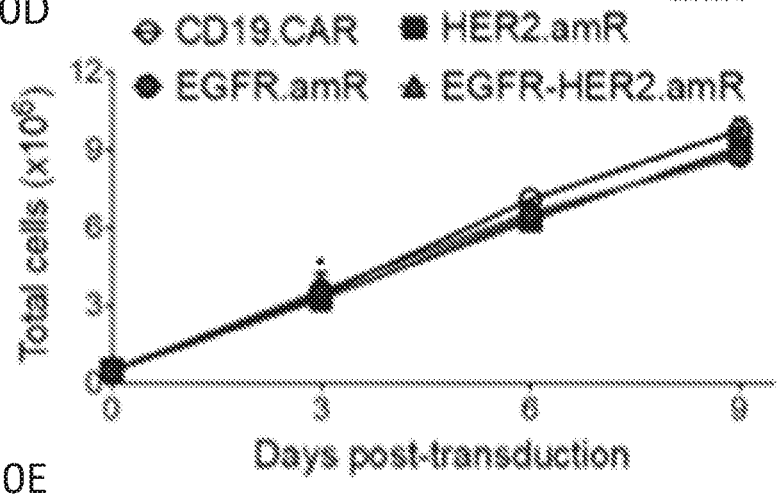
Figure 10E:
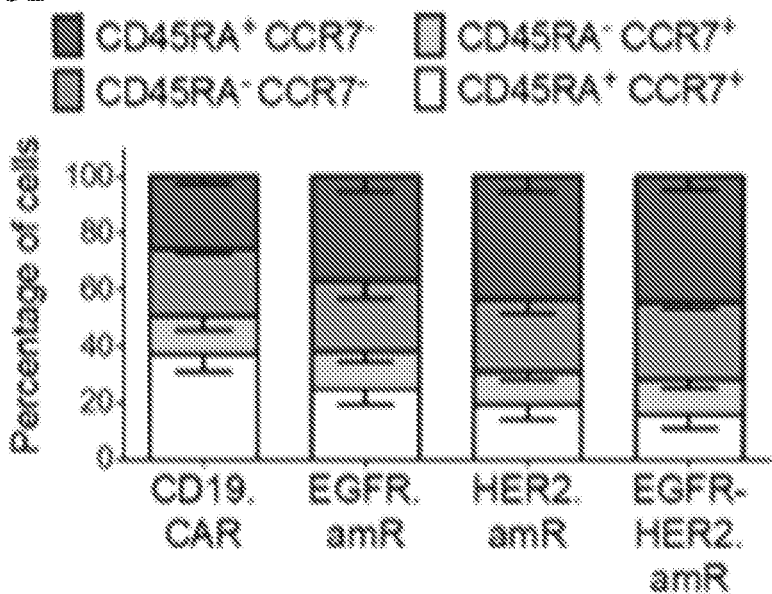
Figure 10F:
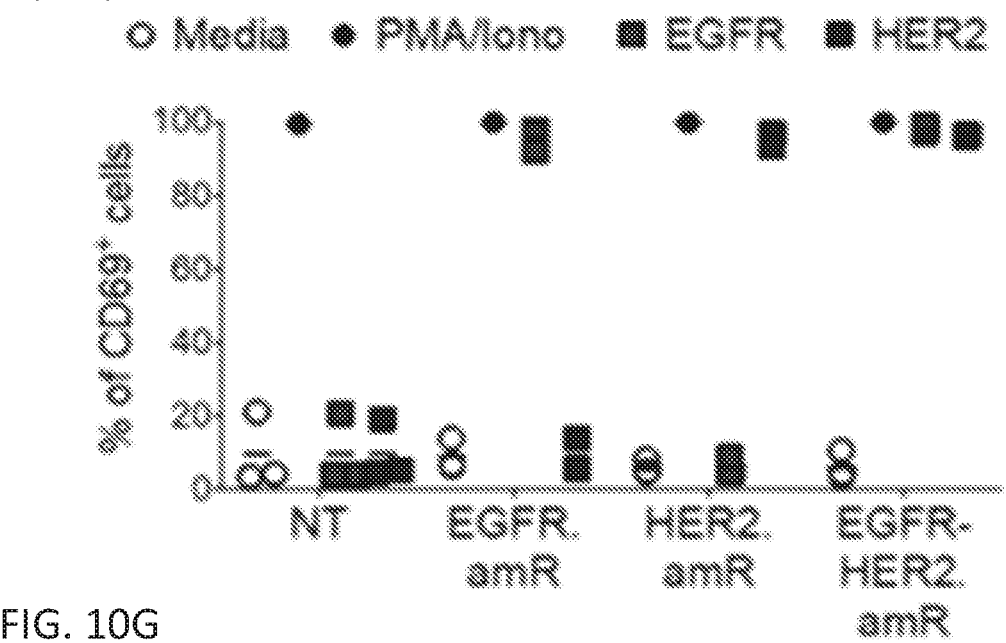
Figure 10G:
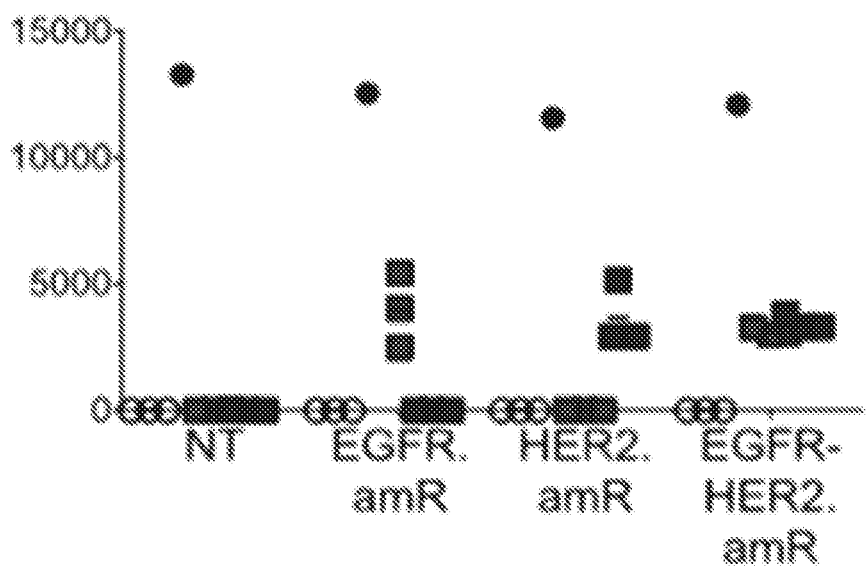
Figure 10H:
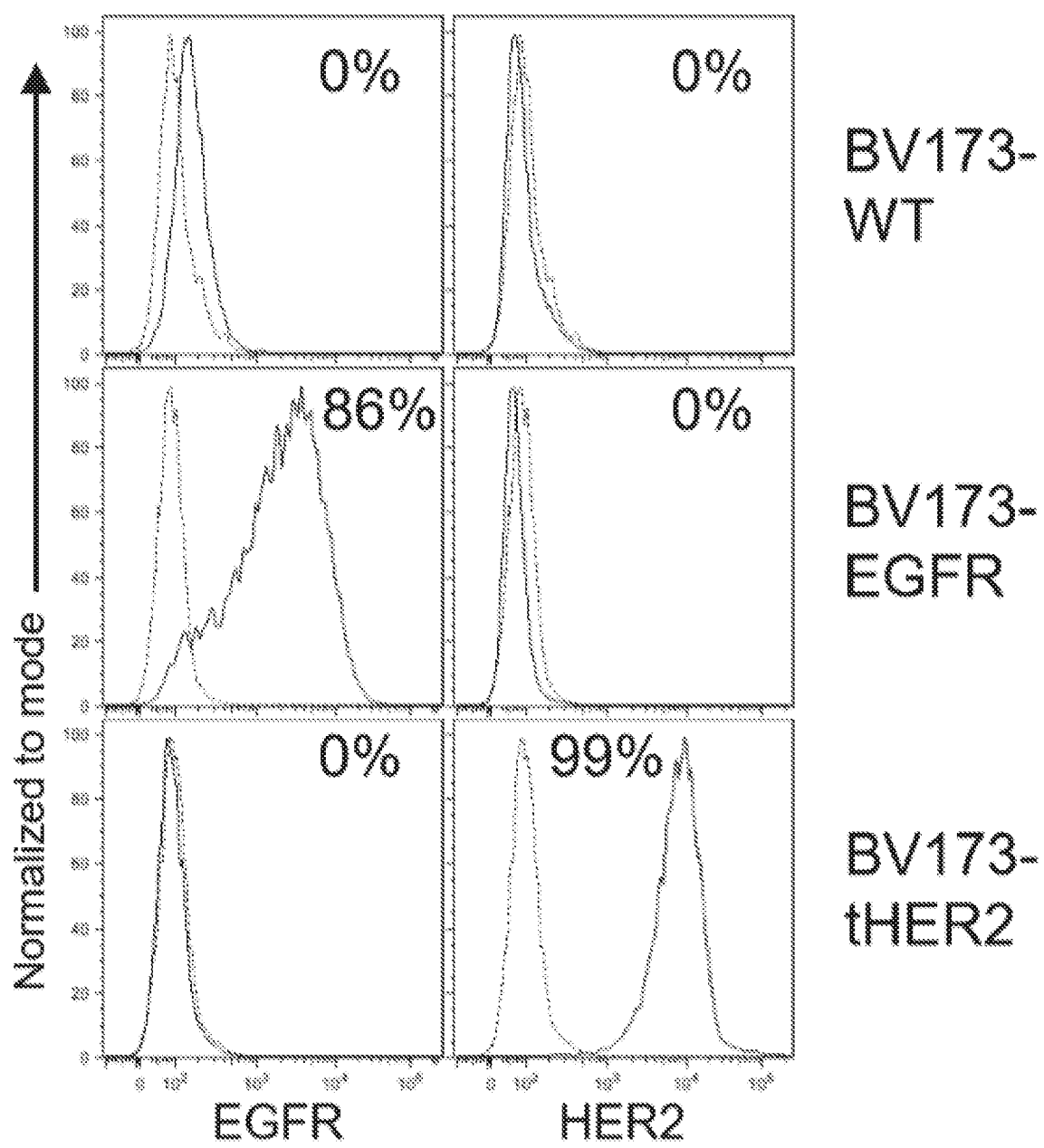
Figure 11A:
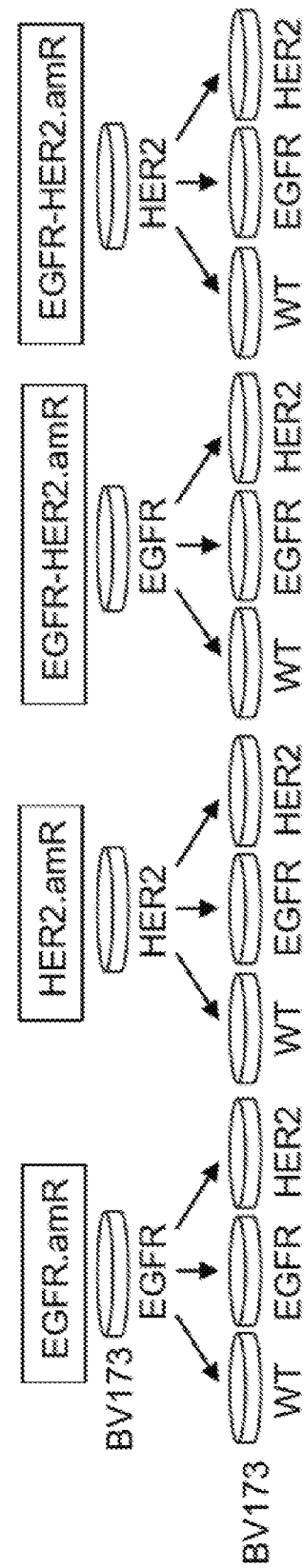
Figure 11B:
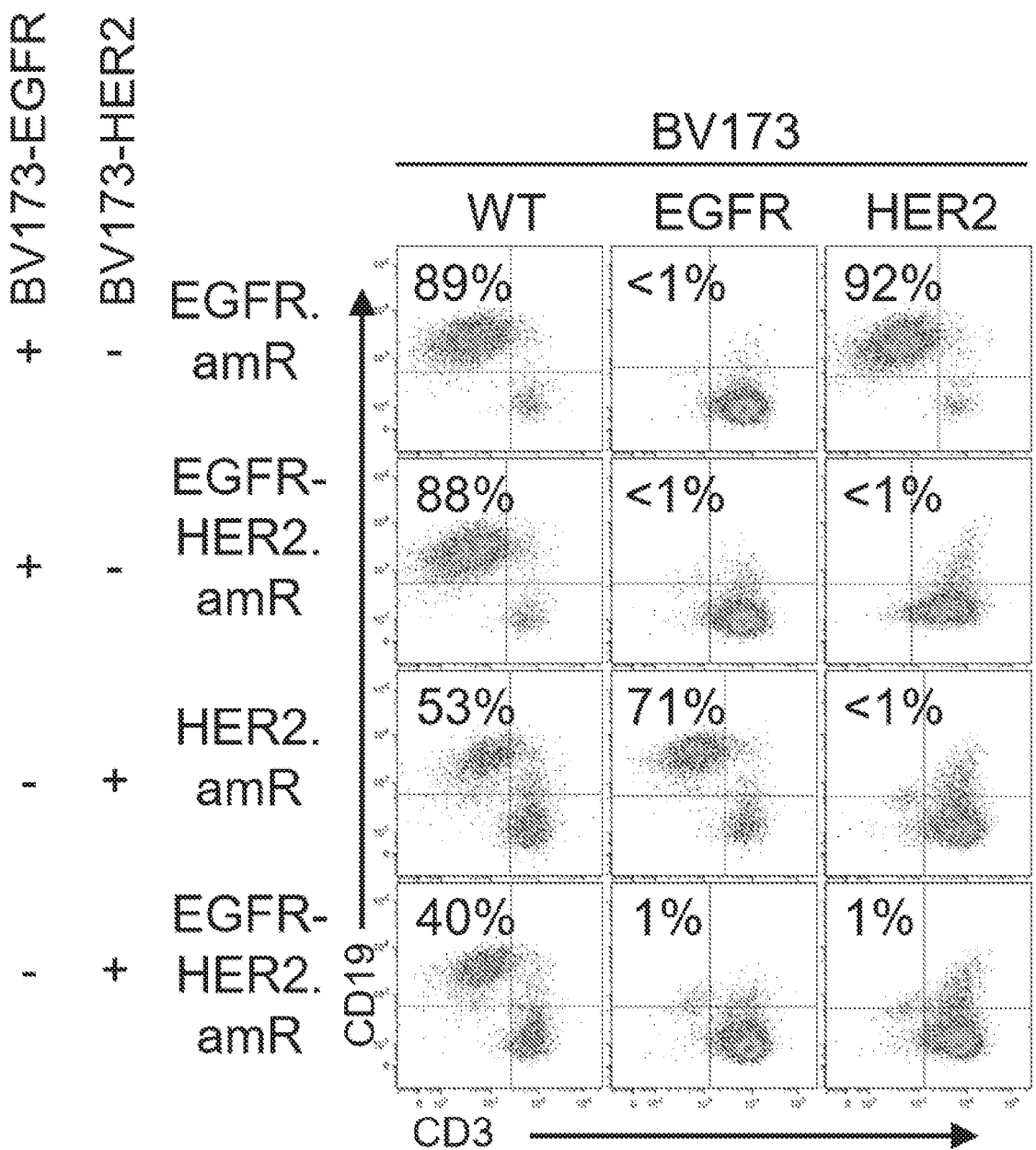
Figure 11C:
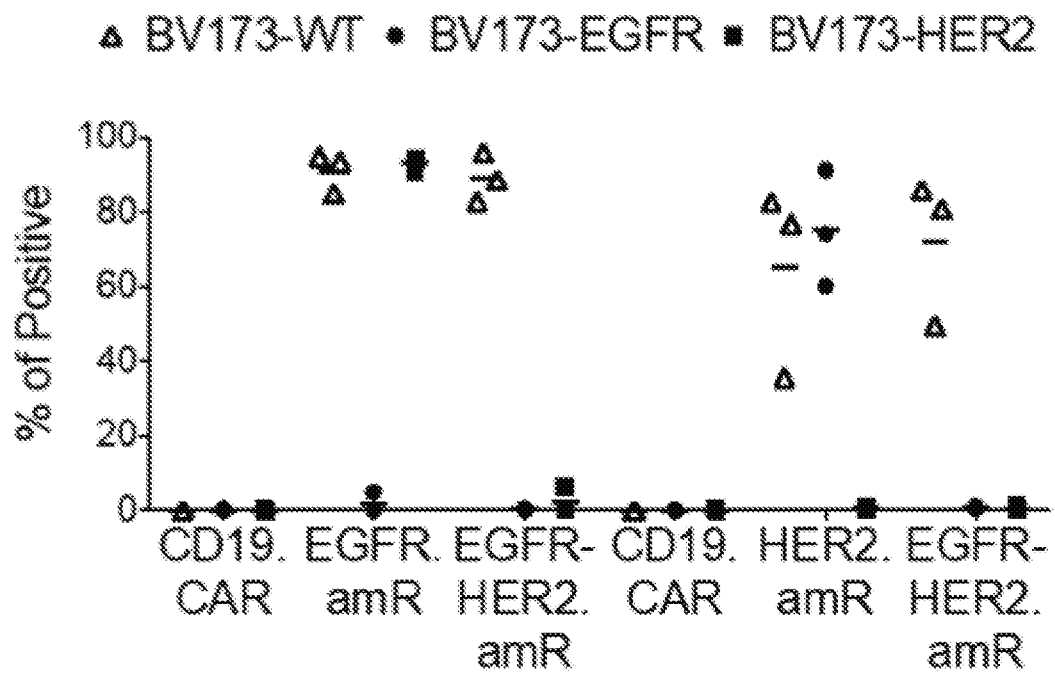
Figure 11D:
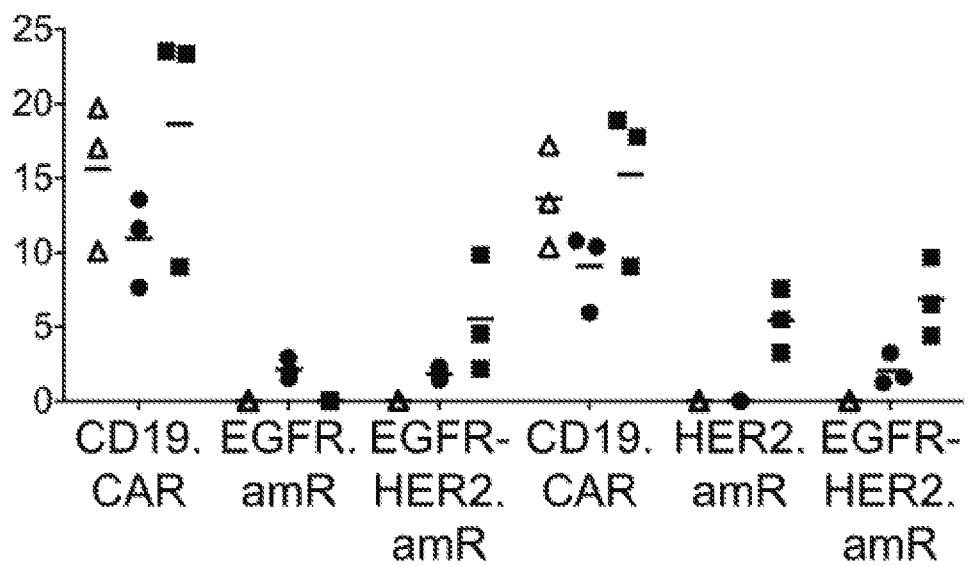
Figure 11E:
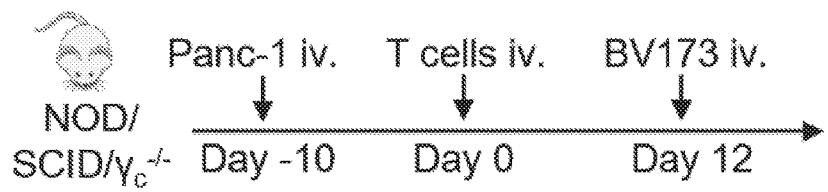
Figure 11F:
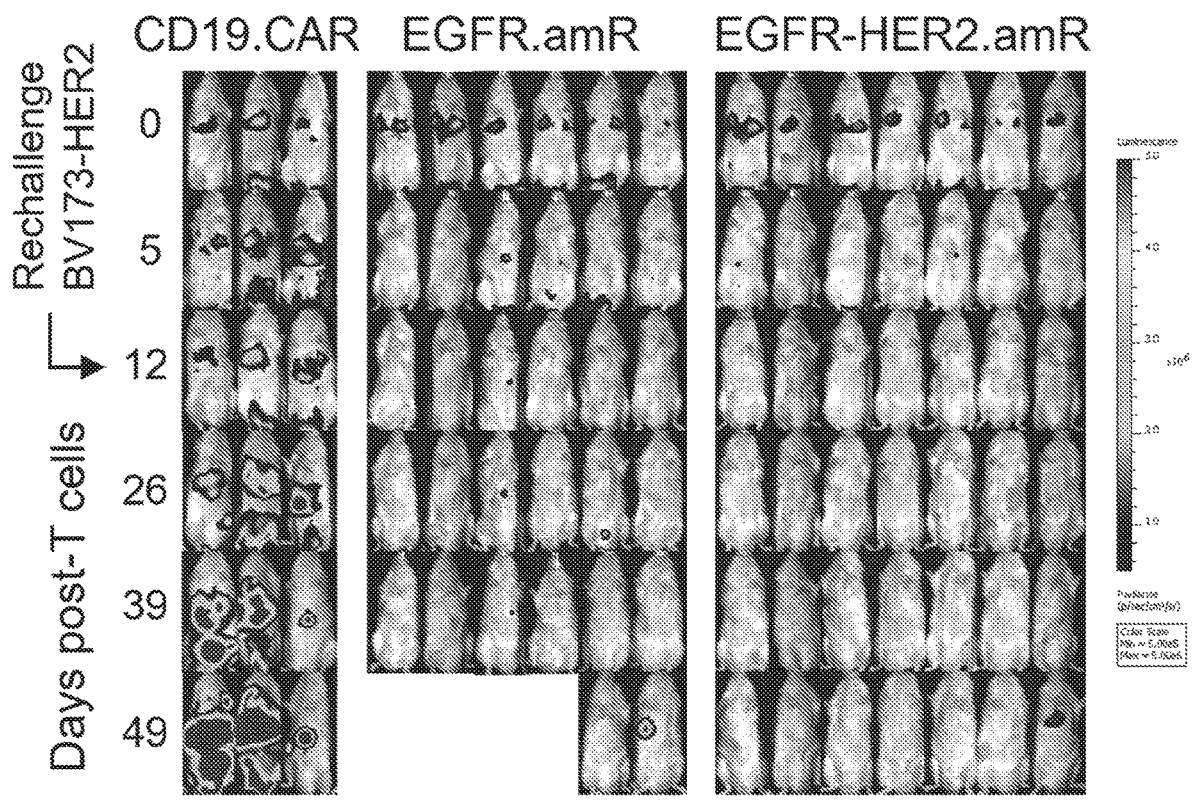
Figure 11G:
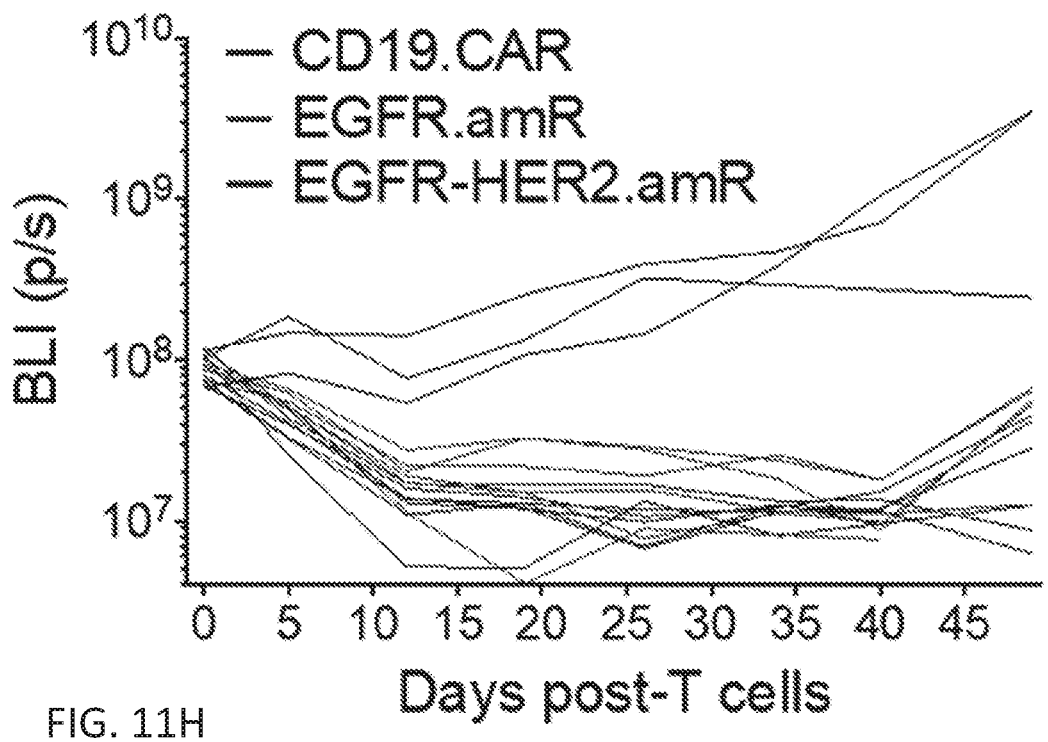
Figure 11H:
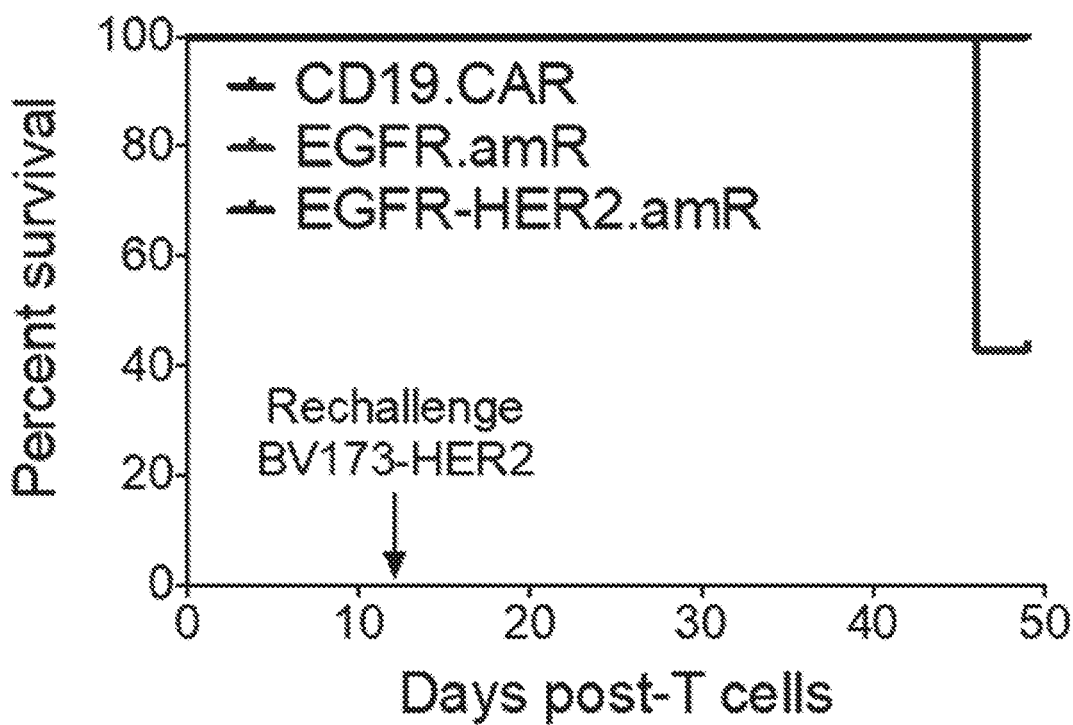

Bispecific EGFR-HER2.amR-Ts have anti-tumor activity against EGFR+ HER2+ tumor cells. To generate amRs targeting two different TAAs, the EGFR specific FN3 binding moiety and the HER2 specific DARPin binding moiety were integrated and created the EGFR-HER2.amR with a 27-residue flexible linker between the two antigen-binding moieties (FIG. 10A). T cells stably expressed the EGFR-HER2.amR (FIG. 10B,C), expanded in vitro in response to exogenous cytokines (FIG. 10D) and maintained T cell composition comparable to monospecific FN3.EGFR.amR-Ts and DARPin.HER2.amR-Ts (FIG. 10E). To establish the bispecificity of EGFR-HER2.amR-Ts, control, FN3.EGFR.amR-Ts, DARPin.HER2.amR-Ts and EGFR-HER2.amR-Ts were seeded in tissue cultures plates coated with either the extracellular domain of rhEGFR or rhHER2 recombinant proteins and CD69 expression and IFN-γ release by T cells was assessed. EGFR-HER2.amR-Ts expressed CD69 (FIG. 10F) and secreted IFN-Y (FIG. 10G) when seeded in wells coated with either rhEGFR or rhHER2 proteins, while FN3.EGFR.amR-Ts and DARPin.HER2.amR-Ts were only activated by rhEGFR and rhHER2, respectively. Next, the functionality of EGFR-HER2.amR-Ts was evaluated against BV173-WT, BV173-EGFR and BV173-HER2 cells (FIG. 10H). A series of co-cultures were performed in which T cells were plated with its respective BV173 target cells, and 3 days later T cells were collected and re-plated with the same BV173 tumor cell line or BV173 cells expressing a non-specific target (FIG. 11A). As shown in FIG. 11B-D, FN3.EGFR.amR-Ts and DARPin.HER2.amR continued to eliminate only BV173-EGFR and BV173-HER2, respectively, while EGFR-HER2.amR-Ts eliminated both BV173-EGFR and BV173-HER2 targets in both the primary and secondary co-cultures. In order to demonstrate the bispecificity of the EGFR-HER2.amR-Ts in vivo, mice were engrafted with the EGFR+ HER2-human Panc-1 cell line labeled with FF-Luc, and infused either with EGFR.amR-Ts or EGFR-HER2.amR-Ts. Tumor growth was equally controlled by both EGFR.amR-Ts and EGFR-HER2.amR-Ts (FIG. 11E-G). However, when these mice were re-challenged with the EGFR-HER2+BV173 tumor cell line, EGFR.amR-T treated mice developed limb paresis due to growth of the BV173 tumor within the spinal cord, while EGFR-HER2.amR Ts treated mice remained healthy (FIG. 11H).

The generation of multi-redirected CAR-Ts may be necessary to effectively eradicate tumors in which TAAs of interest can be lost or are heterogeneously expressed in tumor cells. Herein it is demonstrated that highly modular single domain antibody mimics are a practical alternative to the conventional scFvs to generate T cells with engineered multiple antigen targeting features. Antibody mimics were constructed that can be assembled with signaling molecules of the T cell receptor and costimulatory endodomains. The functionality in vitro and in vivo of T cells expressing antibody mimics is also demonstrated herein, showing their ability to recognize simultaneously two epitopes of the same antigens or two distinct antigens.

As described herein, single domain antibody mimics can be used to redirect the specificity of human T lymphocytes. Single domain antibody mimics binding to the non-overlapping regions of EGFR were generated to create a novel EGFR-binding ligand with biepitopicity. T cells expressing the single domain AFF.EGFR.amR or FN3.EGFR.amR have comparable activity in vitro and in vivo to the conventional scFv-based Cetuximab EGFR.CAR. Though no difference was found in the phenotype and anti-tumor activities of Bi-EGFR.amR-Ts and EGFR.CAR-Ts, it was discovered that Bi-EGFR.amR-Ts have decreased tendency to form oligomers as compared to the conventional EGFR.CAR-Ts. These results suggest that T cells redirected with amRs may receive less tonic signaling than T cells redirected with a conventional scFv-based CAR. To further demonstrate the broad applicability of redirecting T cell specificity by using antibody mimics the approach was also validated by targeting HER2 expressing tumors using a Bi-HER2 targeting ligand. Targeting two epitopes of the same molecule may help prevent tumor escape when the targeted antigen can be expressed by alternative mRNA splicing, which may cause loss of the targeted epitope. When the AFF.EGFR and FN3.EGFR were combined in one single amR cassette, two epitopes of EGFR can be targeted without causing detrimental effects in T cells.

Targeting two distinct antigens expressed by tumor cells remains challenging. Herein it is demonstrated that single domain antibody mimics can be assembled in one single cassette to efficiently target two different antigens. The results presented herein demonstrate that both EGFR and HER2 can be effectively targeted by dual-specific amRs neither with impairing targeting of each single antigen nor with detrimental effects of engineered T cells. In summary, the disclosure demonstrates that antibody mimics can be used to generate combinatorial targeting of engineered T cells. Taking in consideration that antibody mimics are generated synthetically, the disclosed approach can be adapted to a systematic screening of combinatorial antigens to be tested in human malignancies.

What is claimed is:

1. A chimeric antigen receptor (CAR) comprising:
   (a) an extracellular tumor antigen binding moiety comprises the sequence of SEQ ID NO: 1;
   (b) a CD8a hinge;
   (c) a CD8a transmembrane domain;
   (d) an intracellular cytoplasmic domain comprising a CD3 zeta signaling domain and a co-stimulatory domain from CD28.

2. The chimeric antigen receptor of claim 1, wherein the chimeric antigen receptor comprises a polypeptide sequence having at least 90% sequence identity to SEQ ID NO: 4.

3. An engineered immune cell expressing the chimeric antigen receptor of claim 1.

4. A method of treating cancer in a patient, the method comprising administering to the patient a therapeutically effective amount of a composition comprising the engineered immune cell of claim 3.

* * * * *

SEQUENCE LISTING

```
<160> NUMBER OF SEQ ID NOS: 6

<210> SEQ ID NO 1
<211> LENGTH: 226
<212> TYPE: PRT
<213> ORGANISM: Artificial Sequence
<220> FEATURE:
<223> OTHER INFORMATION: Synthetic

<400> SEQUENCE: 1

Met Glu Phe Gly Leu Ser Trp Leu Phe Leu Val Ala Ile Leu Lys Gly
1               5                   10                  15

Val Gln Cys Ser Arg Ser Val Ser Asp Val Pro Arg Asp Leu Glu Val
            20                  25                  30

Val Ala Ala Thr Pro Thr Ser Leu Leu Ile Ser Trp Asp Ser Gly Arg
        35                  40                  45
```

```
Gly Ser Tyr Gln Tyr Tyr Arg Ile Thr Tyr Gly Glu Thr Gly Gly Asn
            50                  55                  60

Ser Pro Val Gln Glu Phe Thr Val Pro Gly Pro Val His Thr Ala Thr
 65                  70                  75                  80

Ile Ser Gly Leu Lys Pro Gly Val Asp Tyr Thr Ile Thr Val Tyr Ala
                 85                  90                  95

Val Thr Asp His Lys Pro His Ala Asp Gly Pro His Thr Tyr His Glu
            100                 105                 110

Ser Pro Ile Ser Ile Asn Tyr Arg Thr Glu Ile Asp Lys Pro Ser Gln
            115                 120                 125

Gly Lys Lys Gly Lys Gly Pro Gln Pro Gln Pro Lys Pro Gln Pro Gln
            130                 135                 140

Pro Gln Pro Gln Pro Lys Pro Gln Pro Lys Pro Glu Pro Glu Gly Gly
145                 150                 155                 160

Val Asp Asn Lys Phe Asn Lys Glu Met Trp Ala Ala Trp Glu Glu Ile
                165                 170                 175

Arg Asn Leu Pro Asn Leu Asn Gly Trp Gln Met Thr Ala Phe Ile Ala
            180                 185                 190

Ser Leu Val Asp Asp Pro Ser Gln Ser Ala Asn Leu Leu Ala Glu Ala
            195                 200                 205

Lys Lys Leu Asn Asp Ala Gln Ala Pro Lys Gly Ser Gly Lys Lys
            210                 215                 220

Gly Lys
225

<210> SEQ ID NO 2
<211> LENGTH: 249
<212> TYPE: PRT
<213> ORGANISM: Artificial Sequence
<220> FEATURE:
<223> OTHER INFORMATION: Synthetic

<400> SEQUENCE: 2

Met Glu Phe Gly Leu Ser Trp Leu Phe Leu Val Ala Ile Leu Lys Gly
 1               5                  10                  15

Val Gln Cys Ser Ala Ala Ala Gly Gly Ser Asp Leu Gly Lys Lys Leu
                 20                  25                  30

Leu Glu Ala Ala Arg Ala Gly Gln Asp Asp Glu Val Arg Ile Leu Met
             35                  40                  45

Ala Asn Gly Ala Asp Val Asn Ala Lys Asp Glu Tyr Gly Leu Thr Pro
 50                  55                  60

Leu Tyr Leu Ala Thr His Gly His Leu Glu Ile Val Glu Val Leu
 65                  70                  75                  80

Leu Lys Asn Gly Ala Asp Val Asn Ala Val Asp Ala Ile Gly Phe Thr
                 85                  90                  95

Pro Leu His Leu Ala Ala Phe Ile Gly His Leu Glu Ile Ala Glu Val
            100                 105                 110

Leu Leu Lys His Gly Ala Asp Val Asn Ala Gln Asp Lys Phe Gly Lys
            115                 120                 125

Thr Ala Phe Asp Ile Ser Ile Gly Asn Gly Asn Glu Asp Leu Ala Glu
            130                 135                 140

Ile Leu Gln Lys Leu Asn Gly Ser Gly Lys Lys Gly Lys Pro Gln Pro
145                 150                 155                 160

Gln Pro Lys Pro Gln Pro Gln Pro Gln Pro Lys Pro Gln Pro
                165                 170                 175
```

```
Lys Pro Glu Pro Glu Gly Gly Val Asp Asn Lys Phe Asn Lys Glu Met
            180                 185                 190

Arg Asn Ala Tyr Trp Glu Ile Ala Leu Leu Pro Asn Leu Asn Asn Gln
            195                 200                 205

Gln Lys Arg Ala Phe Ile Arg Ser Leu Tyr Asp Asp Pro Ser Gln Ser
    210                 215                 220

Ala Asn Leu Leu Ala Glu Ala Lys Lys Leu Asn Asp Ala Gln Ala Pro
225                 230                 235                 240

Lys Gly Ser Gly Gly Lys Lys Gly Lys
                245

<210> SEQ ID NO 3
<211> LENGTH: 294
<212> TYPE: PRT
<213> ORGANISM: Artificial Sequence
<220> FEATURE:
<223> OTHER INFORMATION: Synthetic

<400> SEQUENCE: 3

Met Glu Phe Gly Leu Ser Trp Leu Phe Leu Val Ala Ile Leu Lys Gly
1               5                   10                  15

Val Gln Cys Ser Arg Ser Val Ser Asp Val Pro Arg Asp Leu Glu Val
            20                  25                  30

Val Ala Ala Thr Pro Thr Ser Leu Leu Ile Ser Trp Asp Ser Gly Arg
            35                  40                  45

Gly Ser Tyr Gln Tyr Tyr Arg Ile Thr Tyr Gly Glu Thr Gly Gly Asn
        50                  55                  60

Ser Pro Val Gln Glu Phe Thr Val Pro Gly Pro Val His Thr Ala Thr
65                  70                  75                  80

Ile Ser Gly Leu Lys Pro Gly Val Asp Tyr Thr Ile Thr Val Tyr Ala
                85                  90                  95

Val Thr Asp His Lys Pro His Ala Asp Gly Pro His Thr Tyr His Glu
            100                 105                 110

Ser Pro Ile Ser Ile Asn Tyr Arg Thr Glu Ile Asp Lys Pro Ser Gln
        115                 120                 125

Gly Lys Lys Gly Lys Gly Pro Gln Pro Gln Pro Lys Pro Gln Pro Gln
    130                 135                 140

Pro Gln Pro Gln Pro Lys Pro Gln Pro Lys Pro Glu Pro Glu Gly Ser
145                 150                 155                 160

Gly Ser Asp Leu Gly Lys Lys Leu Leu Glu Ala Ala Arg Ala Gly Gln
                165                 170                 175

Asp Asp Glu Val Arg Ile Leu Met Ala Asn Gly Ala Asp Val Asn Ala
            180                 185                 190

Lys Asp Glu Tyr Gly Leu Thr Pro Leu Tyr Leu Ala Thr Ala His Gly
        195                 200                 205

His Leu Glu Ile Val Glu Val Leu Leu Lys Asn Gly Ala Asp Val Asn
    210                 215                 220

Ala Val Asp Ala Ile Gly Phe Thr Pro Leu His Leu Ala Ala Phe Ile
225                 230                 235                 240

Gly His Leu Glu Ile Ala Glu Val Leu Leu Lys His Gly Ala Asp Val
                245                 250                 255

Asn Ala Gln Asp Lys Phe Gly Lys Thr Ala Phe Asp Ile Ser Ile Gly
            260                 265                 270

Asn Gly Asn Glu Asp Leu Ala Glu Ile Leu Gln Lys Leu Asn Gly Ala
        275                 280                 285
```

Pro Gly Lys Lys Gly Lys
            290

<210> SEQ ID NO 4
<211> LENGTH: 477
<212> TYPE: PRT
<213> ORGANISM: Artificial Sequence
<220> FEATURE:
<223> OTHER INFORMATION: Synthetic

<400> SEQUENCE: 4

Met Glu Phe Gly Leu Ser Trp Leu Phe Leu Val Ala Ile Leu Lys Gly
1               5                   10                  15

Val Gln Cys Ser Arg Ser Val Ser Asp Val Pro Arg Asp Leu Glu Val
            20                  25                  30

Val Ala Ala Thr Pro Thr Ser Leu Leu Ile Ser Trp Asp Ser Gly Arg
        35                  40                  45

Gly Ser Tyr Gln Tyr Tyr Arg Ile Thr Tyr Gly Glu Thr Gly Gly Asn
    50                  55                  60

Ser Pro Val Gln Glu Phe Thr Val Pro Gly Pro Val His Thr Ala Thr
65                  70                  75                  80

Ile Ser Gly Leu Lys Pro Gly Val Asp Tyr Thr Ile Thr Val Tyr Ala
                85                  90                  95

Val Thr Asp His Lys Pro His Ala Asp Gly Pro His Thr Tyr His Glu
            100                 105                 110

Ser Pro Ile Ser Ile Asn Tyr Arg Thr Glu Ile Asp Lys Pro Ser Gln
        115                 120                 125

Gly Lys Lys Gly Lys Gly Pro Gln Pro Gln Pro Lys Pro Gln Pro Gln
    130                 135                 140

Pro Gln Pro Gln Pro Lys Pro Gln Pro Lys Pro Glu Pro Glu Gly Gly
145                 150                 155                 160

Val Asp Asn Lys Phe Asn Lys Glu Met Trp Ala Ala Trp Glu Glu Ile
                165                 170                 175

Arg Asn Leu Pro Asn Leu Asn Gly Trp Gln Met Thr Ala Phe Ile Ala
            180                 185                 190

Ser Leu Val Asp Asp Pro Ser Gln Ser Ala Asn Leu Leu Ala Glu Ala
        195                 200                 205

Lys Lys Leu Asn Asp Ala Gln Ala Pro Lys Gly Gly Gly Gly Ser Gly
    210                 215                 220

Gly Gly Gly Ser Gly Gly Gly Gly Ser Gly Gly Gly Gly Ser Ala Ala
225                 230                 235                 240

Ala Gly Ser Asp Tyr Lys Asp Asp Asp Lys Gly Gly Thr Arg Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
        275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Arg Ser Lys Arg Ser Arg Leu Leu His Ser Asp Tyr
                325                 330                 335

Met Asn Met Thr Pro Arg Arg Pro Gly Pro Thr Arg Lys His Tyr Gln
            340                 345                 350

```
Pro Tyr Ala Pro Pro Arg Asp Phe Ala Ala Tyr Arg Ser Arg Val Lys
            355                 360                 365

Phe Ser Arg Ser Ala Asp Ala Pro Ala Tyr Gln Gln Gly Gln Asn Gln
370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
            435                 440                 445

Lys Gly His Asp Gly Leu Tyr Gln Gly Leu Ser Thr Ala Thr Lys Asp
            450                 455                 460

Thr Tyr Asp Ala Leu His Met Gln Ala Leu Pro Pro Arg
465                 470                 475

<210> SEQ ID NO 5
<211> LENGTH: 497
<212> TYPE: PRT
<213> ORGANISM: Artificial Sequence
<220> FEATURE:
<223> OTHER INFORMATION: Synthetic

<400> SEQUENCE: 5

Met Glu Phe Gly Leu Ser Trp Leu Phe Leu Val Ala Ile Leu Lys Gly
1               5                   10                  15

Val Gln Cys Ser Ala Ala Ala Gly Gly Ser Asp Leu Gly Lys Lys Leu
            20                  25                  30

Leu Glu Ala Ala Arg Ala Gly Gln Asp Asp Glu Val Arg Ile Leu Met
            35                  40                  45

Ala Asn Gly Ala Asp Val Asn Ala Lys Asp Glu Tyr Gly Leu Thr Pro
        50                  55                  60

Leu Tyr Leu Ala Thr Ala His Gly His Leu Glu Ile Val Glu Val Leu
65                  70                  75                  80

Leu Lys Asn Gly Ala Asp Val Asn Ala Val Asp Ala Ile Gly Phe Thr
                85                  90                  95

Pro Leu His Leu Ala Ala Phe Ile Gly His Leu Glu Ile Ala Glu Val
            100                 105                 110

Leu Leu Lys His Gly Ala Asp Val Asn Ala Gln Asp Lys Phe Gly Lys
            115                 120                 125

Thr Ala Phe Asp Ile Ser Ile Gly Asn Gly Asn Glu Asp Leu Ala Glu
        130                 135                 140

Ile Leu Gln Lys Leu Asn Gly Ser Gly Lys Lys Gly Lys Pro Gln Pro
145                 150                 155                 160

Gln Pro Lys Pro Gln Pro Gln Pro Gln Pro Lys Pro Gln Pro
                165                 170                 175

Lys Pro Glu Pro Glu Gly Gly Val Asp Asn Lys Phe Asn Lys Glu Met
            180                 185                 190

Arg Asn Ala Tyr Trp Glu Ile Ala Leu Leu Pro Asn Leu Asn Asn Gln
            195                 200                 205

Gln Lys Arg Ala Phe Ile Arg Ser Leu Tyr Asp Asp Pro Ser Gln Ser
        210                 215                 220

Ala Asn Leu Leu Ala Glu Ala Lys Lys Leu Asn Asp Ala Gln Ala Pro
225                 230                 235                 240
```

```
Lys Gly Ser Gly Gly Lys Gly Lys Gly Gly Ser Gly Ser Ser Gly
                245                 250                 255

Gly Gly Gly Gly Ser Gly Ser Asp Tyr Lys Asp Asp Asp Lys Gly
            260                 265                 270

Gly Thr Arg Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Arg Ser Lys Arg Ser Arg Leu Leu
                340                 345                 350

His Ser Asp Tyr Met Asn Met Thr Pro Arg Arg Pro Gly Pro Thr Arg
                355                 360                 365

Lys His Tyr Gln Pro Tyr Ala Pro Pro Arg Asp Phe Ala Ala Tyr Arg
        370                 375                 380

Ser Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
                420                 425                 430

Lys Pro Arg Arg Lys Asn Pro Gln Glu Gly Leu Tyr Asn Glu Leu Gln
                435                 440                 445

Lys Asp Lys Met Ala Glu Ala Tyr Ser Glu Ile Gly Met Lys Gly Glu
                450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 6
<211> LENGTH: 543
<212> TYPE: PRT
<213> ORGANISM: Artificial Sequence
<220> FEATURE:
<223> OTHER INFORMATION: Synthetic

<400> SEQUENCE: 6

Met Glu Phe Gly Leu Ser Trp Leu Phe Leu Val Ala Ile Leu Lys Gly
1               5                   10                  15

Val Gln Cys Ser Arg Ser Val Ser Asp Val Pro Arg Asp Leu Glu Val
            20                  25                  30

Val Ala Ala Thr Pro Thr Ser Leu Leu Ile Ser Trp Asp Ser Gly Arg
        35                  40                  45

Gly Ser Tyr Gln Tyr Tyr Arg Ile Thr Tyr Gly Glu Thr Gly Gly Asn
    50                  55                  60

Ser Pro Val Gln Glu Phe Thr Val Pro Gly Pro Val His Thr Ala Thr
65                  70                  75                  80

Ile Ser Gly Leu Lys Pro Gly Val Asp Tyr Thr Ile Thr Val Tyr Ala
                85                  90                  95
```

-continued

Val Thr Asp His Lys Pro His Ala Asp Gly Pro His Thr Tyr His Glu
            100                 105                 110

Ser Pro Ile Ser Ile Asn Tyr Arg Thr Glu Ile Asp Lys Pro Ser Gln
            115                 120                 125

Gly Lys Lys Gly Lys Gly Pro Gln Pro Gln Pro Lys Pro Gln Pro Gln
130                 135                 140

Pro Gln Pro Gln Pro Lys Pro Gln Pro Lys Pro Glu Pro Glu Gly Ser
145                 150                 155                 160

Gly Ser Asp Leu Gly Lys Lys Leu Leu Glu Ala Ala Arg Ala Gly Gln
            165                 170                 175

Asp Asp Glu Val Arg Ile Leu Met Ala Asn Gly Ala Asp Val Asn Ala
            180                 185                 190

Lys Asp Glu Tyr Gly Leu Thr Pro Leu Tyr Leu Ala Thr Ala His Gly
            195                 200                 205

His Leu Glu Ile Val Glu Val Leu Leu Lys Asn Gly Ala Asp Val Asn
            210                 215                 220

Ala Val Asp Ala Ile Gly Phe Thr Pro Leu His Leu Ala Ala Phe Ile
225                 230                 235                 240

Gly His Leu Glu Ile Ala Glu Val Leu Leu Lys His Gly Ala Asp Val
            245                 250                 255

Asn Ala Gln Asp Lys Phe Gly Lys Thr Ala Phe Asp Ile Ser Ile Gly
            260                 265                 270

Asn Gly Asn Glu Asp Leu Ala Glu Ile Leu Gln Lys Leu Asn Gly Ala
            275                 280                 285

Pro Gly Lys Lys Gly Lys Ala Ala Gly Gly Gly Ser Gly Gly
            290                 295                 300

Gly Gly Ser Gly Gly Asp Tyr Lys Asp Asp Asp Lys Gly Gly Thr
305                 310                 315                 320

Arg Thr Thr Thr Pro Ala Pro Arg Pro Pro Thr Pro Ala Pro Thr Ile
            325                 330                 335

Ala Ser Gln Pro Leu Ser Leu Arg Pro Glu Ala Cys Arg Pro Ala Ala
            340                 345                 350

Gly Gly Ala Val His Thr Arg Gly Leu Asp Phe Ala Cys Asp Ile Tyr
            355                 360                 365

Ile Trp Ala Pro Leu Ala Gly Thr Cys Gly Val Leu Leu Leu Ser Leu
            370                 375                 380

Val Ile Thr Leu Tyr Cys Arg Ser Lys Arg Ser Arg Leu Leu His Ser
385                 390                 395                 400

Asp Tyr Met Asn Met Thr Pro Arg Arg Pro Gly Pro Thr Arg Lys His
            405                 410                 415

Tyr Gln Pro Tyr Ala Pro Pro Arg Asp Phe Ala Ala Tyr Arg Ser Arg
            420                 425                 430

Val Lys Phe Ser Arg Ser Ala Asp Ala Pro Ala Tyr Gln Gln Gly Gln
            435                 440                 445

Asn Gln Leu Tyr Asn Glu Leu Asn Leu Gly Arg Arg Glu Glu Tyr Asp
            450                 455                 460

Val Leu Asp Lys Arg Arg Gly Arg Asp Pro Glu Met Gly Gly Lys Pro
465                 470                 475                 480

Arg Arg Lys Asn Pro Gln Glu Gly Leu Tyr Asn Glu Leu Gln Lys Asp
            485                 490                 495

Lys Met Ala Glu Ala Tyr Ser Glu Ile Gly Met Lys Gly Glu Arg Arg
            500                 505                 510

Arg Gly Lys Gly His Asp Gly Leu Tyr Gln Gly Leu Ser Thr Ala Thr

-continued

```
            515                 520                 525
Lys Asp Thr Tyr Asp Ala Leu His Met Gln Ala Leu Pro Pro Arg
        530                 535                 540
```